(12) United States Patent
Melman et al.

(10) Patent No.: US 11,213,259 B2
(45) Date of Patent: Jan. 4, 2022

(54) X-RAY REDUCTION SYSTEM

(71) Applicant: CONTROLRAD SYSTEMS INC., Radnor, PA (US)

(72) Inventors: Haim Zvi Melman, Kfar Saba (IL); Liron Melman, Tel Aviv (IL); Gilad Nave-Frost, Rosh-HaAyin (IL); Allon Guez, Penn Valley, PA (US)

(73) Assignee: CONTROLRAD, INC., Peachtree Corners, GA (US)

( * ) Notice: Subject to any disclaimer, the term of this patent is extended or adjusted under 35 U.S.C. 154(b) by 0 days.

(21) Appl. No.: 16/885,373

(22) Filed: May 28, 2020

(65) Prior Publication Data

US 2020/0315552 A1    Oct. 8, 2020

Related U.S. Application Data

(63) Continuation-in-part of application No. 16/158,347, filed on Oct. 12, 2018, now Pat. No. 10,695,012, which is a continuation of application No. 15/103,668, filed as application No. PCT/IB2014/075661 on Oct. 28, 2014, now Pat. No. 10,149,654.

(60) Provisional application No. 61/927,504, filed on Jan. 15, 2014, provisional application No. 61/914,405, filed on Dec. 11, 2013.

(51) Int. Cl.
*A61B 6/00* (2006.01)
*A61B 6/06* (2006.01)
*A61B 6/10* (2006.01)

(52) U.S. Cl.
CPC ............ *A61B 6/06* (2013.01); *A61B 6/107* (2013.01); *A61B 6/4405* (2013.01); *A61B 6/4441* (2013.01); *A61B 6/4458* (2013.01); *A61B 6/461* (2013.01); *A61B 6/469* (2013.01); *A61B 6/486* (2013.01); *A61B 6/5205* (2013.01); *A61B 6/548* (2013.01); *A61B 6/487* (2013.01); *A61B 6/504* (2013.01)

(58) Field of Classification Search
CPC ......... A61B 6/06; A61B 6/107; A61B 6/4405; A61B 6/4441; A61B 6/548; A61B 6/504; A61B 6/461; A61B 6/469; A61B 6/486; A61B 6/5205; A61B 6/4458
See application file for complete search history.

(56) References Cited

U.S. PATENT DOCUMENTS

2013/0336445 A1\* 12/2013 Sehnert .................. A61B 6/487
378/42
2015/0223767 A1\* 8/2015 Sehnert ................ A61B 6/4411
378/42

\* cited by examiner

*Primary Examiner* — Don K Wong
(74) *Attorney, Agent, or Firm* — Manelli Selter PLLC; Edward Stemberger

(57) ABSTRACT

An imaging system comprising a radiation source and radiation thereby; a detector having an input surface; a monitor configured to display images detected by the detector; a Graphical User Interface (GUI) for determining at least one Region of Interest (ROI) on a displayed image; and a collimator comprising means for modulating intensity of the radiation according to the at least one ROI; wherein the GUI comprises means for displaying detected images and means for determining shape and location of the at least one ROI.

31 Claims, 39 Drawing Sheets

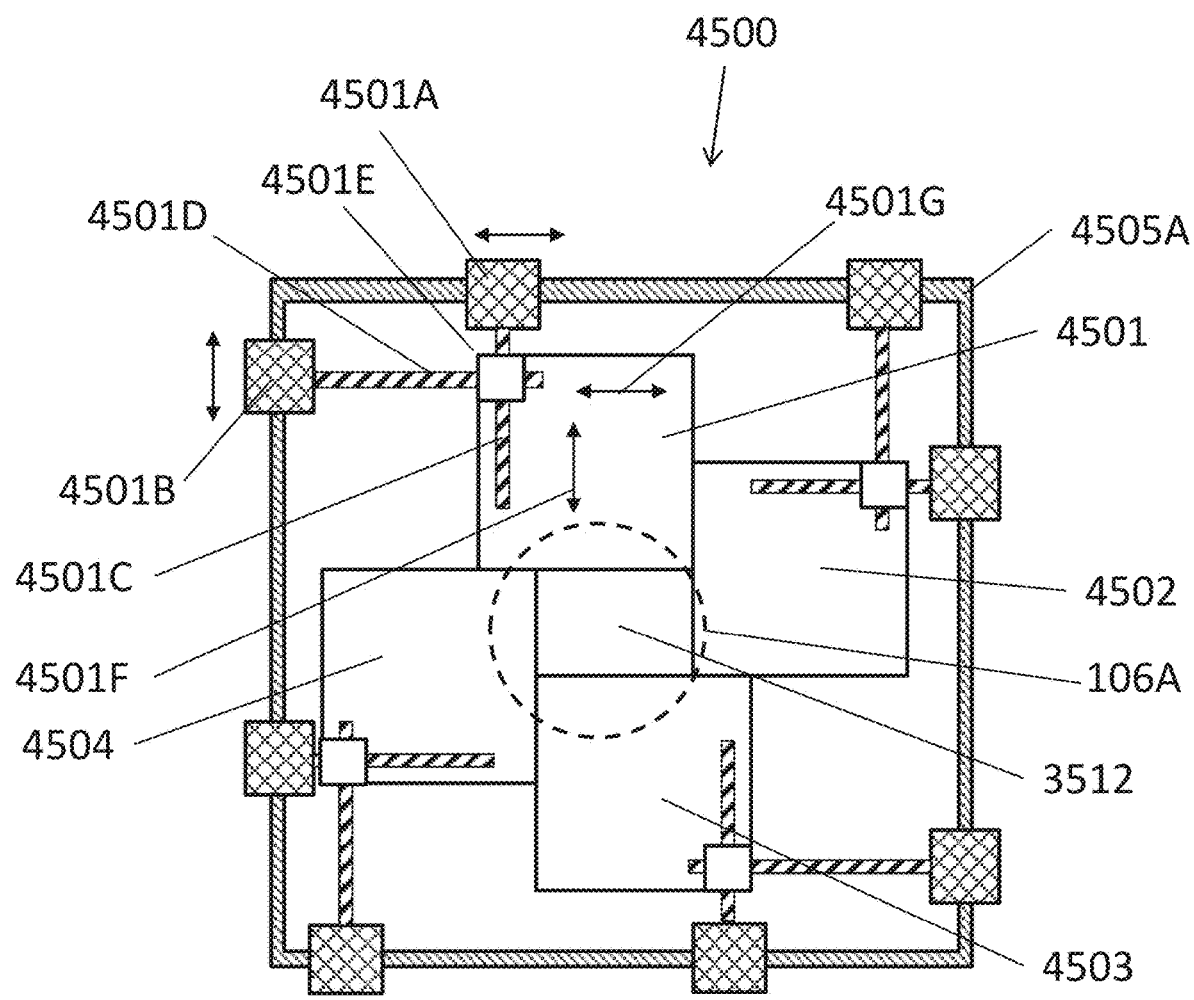
Figure 4
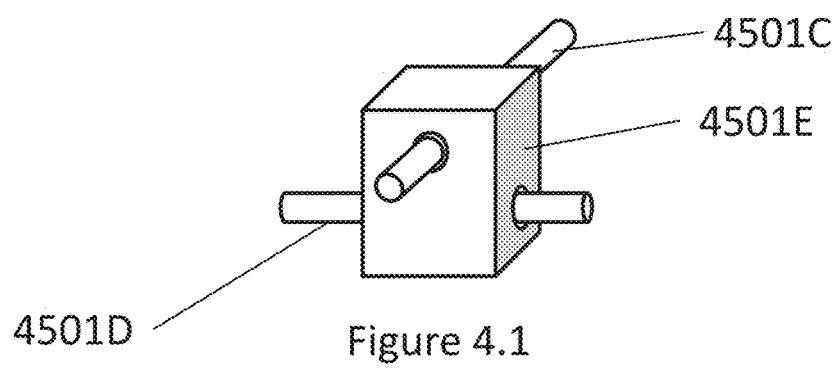
Figure 4.1

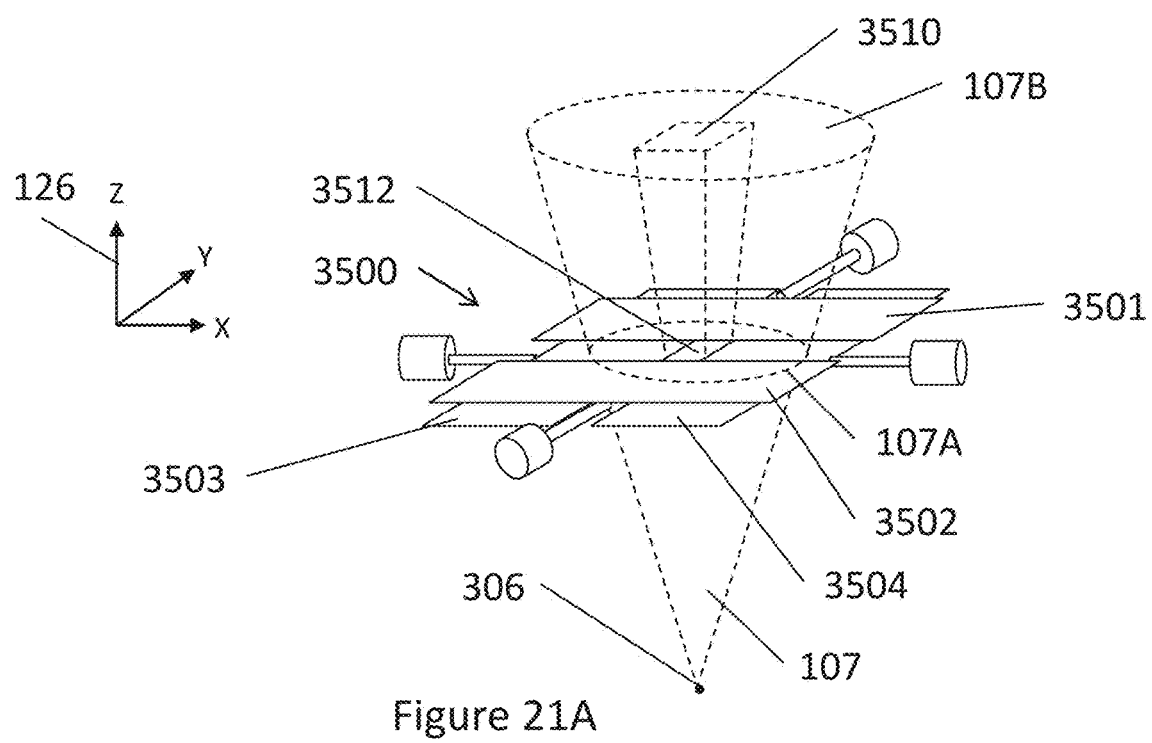
Figure 21A
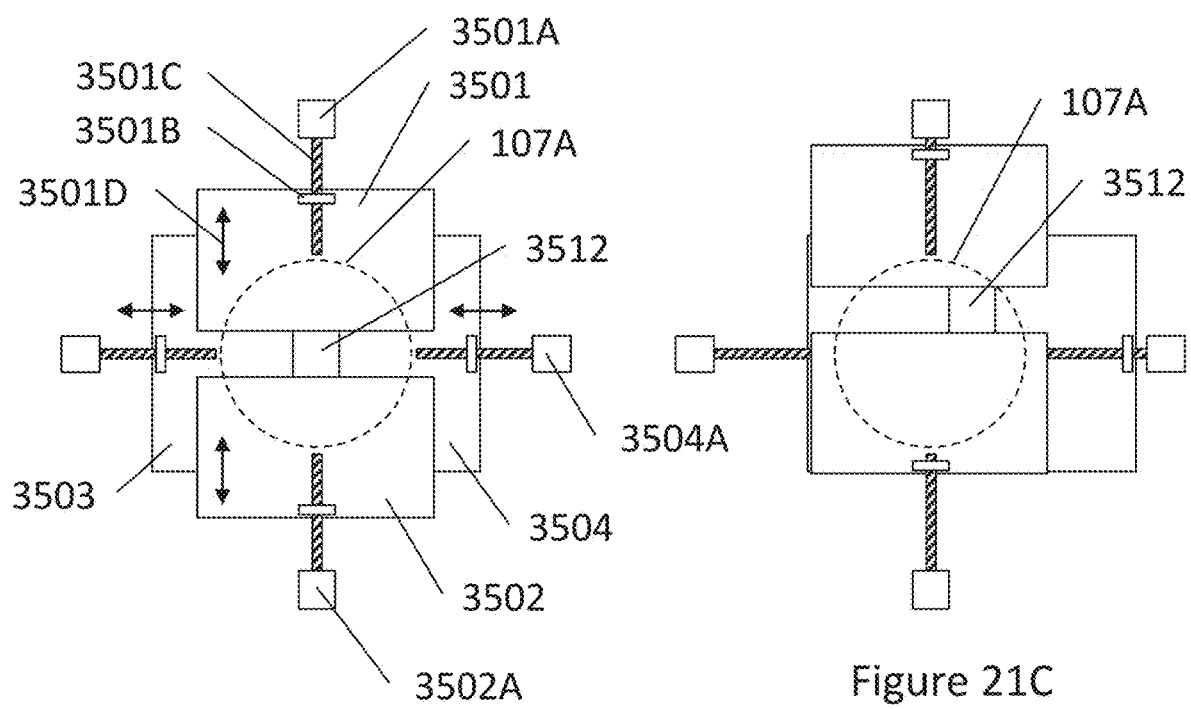
Figure 21B
Figure 21C

X-RAY REDUCTION SYSTEM

FIELD OF THE INVENTION

The invention is related to the field of x-ray imaging and more particularly to the field of controlling x-ray radiation amount during multiple frames imaging.

BACKGROUND OF THE INVENTION

In a typical multiple frames imaging (MFI) system the x-ray tube generates x-ray radiation over a relatively wide solid angle. To avoid unnecessary exposure to both the patient and the medical team, collimators of x-ray absorbing materials such as lead are used to block the redundant radiation. This way only the necessary solid angle of useful radiation exits the x-ray tube to expose only the necessary elements.

Such collimators are used typically in a static mode but may assume a variety of designs and x-ray radiation geometries. Collimators can be set up manually or automatically using as input, for example, the dimensions of the organ environment that is involved in the procedure.

In multiple frames imaging, where typically a series of images are taken automatically one after the other, the situation is more dynamic than in a single exposure x-ray.

For such cases collimators with materials partially-transparent to x-ray may be used to manipulate the x-ray energy distribution.

It is desired to change the distribution of the x-ray energy during the MFI session so that for at least 2 different frames of the MFI session the distribution of the x-ray beam will be different.

In MFI the x-ray radiation is active for a relatively long period and the treating physician typically has to stand near the patient, therefore near the x-ray radiation. As a result, it is desired to provide methods to minimize exposure to the medical team. Methods for reducing x-ray radiation intensity have been suggested where the resultant reduced signal to noise ratio (S/N) of the x-ray image is compensated by digital image enhancement. Other methods suggest a collimator limiting the solid angle of the x-ray radiation to a fraction of the image intensifier area and periodically moving the collimator to expose the entire input area of the image intensifier so that the Region of Interest (ROI) is exposed more than the rest of the area. This way, the ROI receives high enough x-ray radiation to generate a good S/N image while the rest of the image is exposed with low x-ray intensity, providing a relatively low S/N image or reduced real-time imaging, as per the collimator and method used. The ROI size and position can be determined in a plurality of methods. For example, it can be a fixed area in the center of the image or it can be centered automatically about the most active area in the image, this activity is determined by temporal image analysis of sequence of cine images received from the video camera of the multiple frames imaging system.

It is desired to provide collimator solutions to enable reduction of dose during MFI.

It is also desired to provide a method to move the collimator elements so as to support best imaging results.

It is desired to provide a method to handle the effects of this motion on image quality.

SUMMARY OF THE INVENTION

According to an aspect of the present invention there is provided an imaging system comprising: a radiation source and radiation thereby; a detector having an input surface; a monitor configured to display images detected by the detector; a Graphical User Interface (GUI) for determining at least one Region of Interest (ROI) on a displayed image; and a collimator comprising means for modulating intensity of the radiation according to the at least one ROI; wherein the GUI comprises means for displaying detected images and means for determining shape and location of the at least one ROI.

The imaging system may further comprise an image processing unit connected between the detector and the monitor, the image processing unit configured to optimize a detected image displayed on the monitor according to at least one image part in the at least one ROI.

The means for determining shape and location of the at least one ROI may comprise sliders.

The means for determining shape and location of the at least one ROI may comprise drawing tools.

The drawing tools may be configured to enable to mark an enclosing shape around at least one image area.

The drawing tools may be configured to enable to mark at least one line; and wherein the means for determining shape and location of the at least one ROI may comprise means for calculating an enclosing shape around the at least one line.

The means for determining shape and location of the at least one ROI may comprise means for tapping on a selected location on the means for displaying and means for determining an enclosing shape around the tapping location.

The means for determining shape and location of the at least one ROI may comprise means for tapping on a selected location on the means for displaying thereby drawing a predetermined enclosing shape around the tapping location.

The means for determining shape and location of the at least one ROI may comprise means for tapping on a selected location on the means for displaying; and wherein the imaging system may further comprises an image processing unit configured to perform image processing for recognizing an organ area in which the selected location is included, thereby drawing a predetermined shape around the recognized organ.

The imaging system may further comprise means for locking and moving the determined shape of the at least one ROI on the means for displaying.

The means for moving the determined shape of the at least one ROI may comprise means for moving the determined shape by dragging the determined shape to a different location on the means for displaying.

The means for moving the determined shape of the at least one ROI may comprise means for tapping on a different location on the means for displaying thereby automatically moving the determined shape to the different location on the means for displaying.

The imaging system may further comprise an image processing unit configured to perform image processing for recognizing an organ included in a selected location; and wherein the means for moving the determined shape of the at least one ROI may comprise means for automatically moving the determined shape according to movements of the organ on the means for displaying.

The means for moving the determined shape of the at least one ROI on the means for displaying may comprise at least one of a tracking device and a voice command.

The tracking device may comprise at least one of an eye tracker; and a hand gesture tracking device.

The imaging system may further comprise means for at least one of automatically moving a selected ROI on the means for displaying; and automatically changing the size of a selected ROI based on one of: a movement of a patient; a movement of a table, on which the patient is lying; and a movement of a medical device inserted into the patient's body.

The GUI may further comprise means for rotating the determined at least one ROI.

According to another aspect of the present invention there is provided a method of controlling a shape of a Region of Interest (ROI) in an imaging system, comprising: providing a imaging system comprising: a radiation source and radiation thereby; a detector having an input surface; a Graphical User Interface (GUI) for determining the at least one ROI; and a collimator comprising means for modulating intensity of the radiation according to the at least one ROI; wherein the GUI comprises means for displaying detected images and means for determining shape and location of the at least one ROI; and using the GUI for displaying detected images and determining shape and location of the at least one ROI.

The determining shape and location of the at least one ROI may comprise moving sliders.

The determining shape and location of the at least one ROI may comprise drawing an enclosing shape around at least one image area.

The determining shape and location of the at least one ROI may comprise drawing at least one line; and calculating an enclosing shape around the at least one line.

The determining shape and location of the at least one ROI may comprise tapping on a selected location on the means for displaying; and determining an enclosing shape around the tapping.

The determining shape and location of the at least one ROI may comprise tapping on a selected location on the means for displaying thereby drawing a predetermined shape around the tapping location.

The determining shape and location of the at least one ROI may comprise tapping on a selected location on the means for displaying; recognizing an organ area in which the selected location is included by image processing; and drawing a predetermined shape around the recognized organ.

The method may further comprise locking and moving the determined shape of the at least one ROI on the means for displaying.

The moving of the determined shape of the at least one ROI may comprise dragging the determined shape to a different location on the means for displaying.

The moving of the determined shape of the at least one ROI may comprise tapping on a different location on the means for displaying thereby automatically moving the determined shape to the different location on the means for displaying.

The moving of the determined shape of the at least one ROI may comprise using image processing for recognizing an organ; and automatically moving the determined shape according to movements of the organ on the means for displaying.

The moving of the determined shape of the at least one ROI on the means for displaying may comprise using at least one of a tracking device and a voice command.

The tracking device may comprise at least one of an eye tracker; and a hand gesture tracking device.

The method may further comprise at least one of automatically moving a selected ROI on the means for displaying; and automatically changing the size of a selected ROI based on one of: a movement of a patient; a movement of a table, on which the patient is lying; and a movement of a medical device inserted into the patient's body.

BRIEF DESCRIPTION OF THE DRAWINGS

The invention will be better understood in reference to the following Figures:

FIG. 4 is a top view of a collimator constructed of four partially x-ray transparent essentially non-overlapping plates with the ROI at the center;

FIG. 4.1 shows an example of possible arrangement of nut 4501E;

FIG. 13HJ is another example of possible shapes drawing and automatic ROI setup using the user interface of FIG. 13A;

FIG. 21A provides a view of a collimator constructed of 4 partially x-ray transparent plates;

FIG. 21B is a top view of the collimator of FIG. 21A with the ROI at the center;

FIG. 21C is a top view of the collimator of FIG. 21A with the ROI at an off-center location;

DETAILED DESCRIPTION OF THE INVENTION

Throughout the following description reference is made to various collimators having plates or filters. Both terms are used in the same sense, to describe filters intended to change the intensity of the radiation in a non-uniform manner over the Field of View (FOV), as opposed to filters intended for changing the spectrum of the radiation throughout the FOV. The action of collimator, is also described in terms of modulation the x-ray radiation intensity in the FOV or in other words, modulating the x-ray radiation intensity according to the ROI. Also, the word radiation also means x-ray radiation.

Figure 1A:
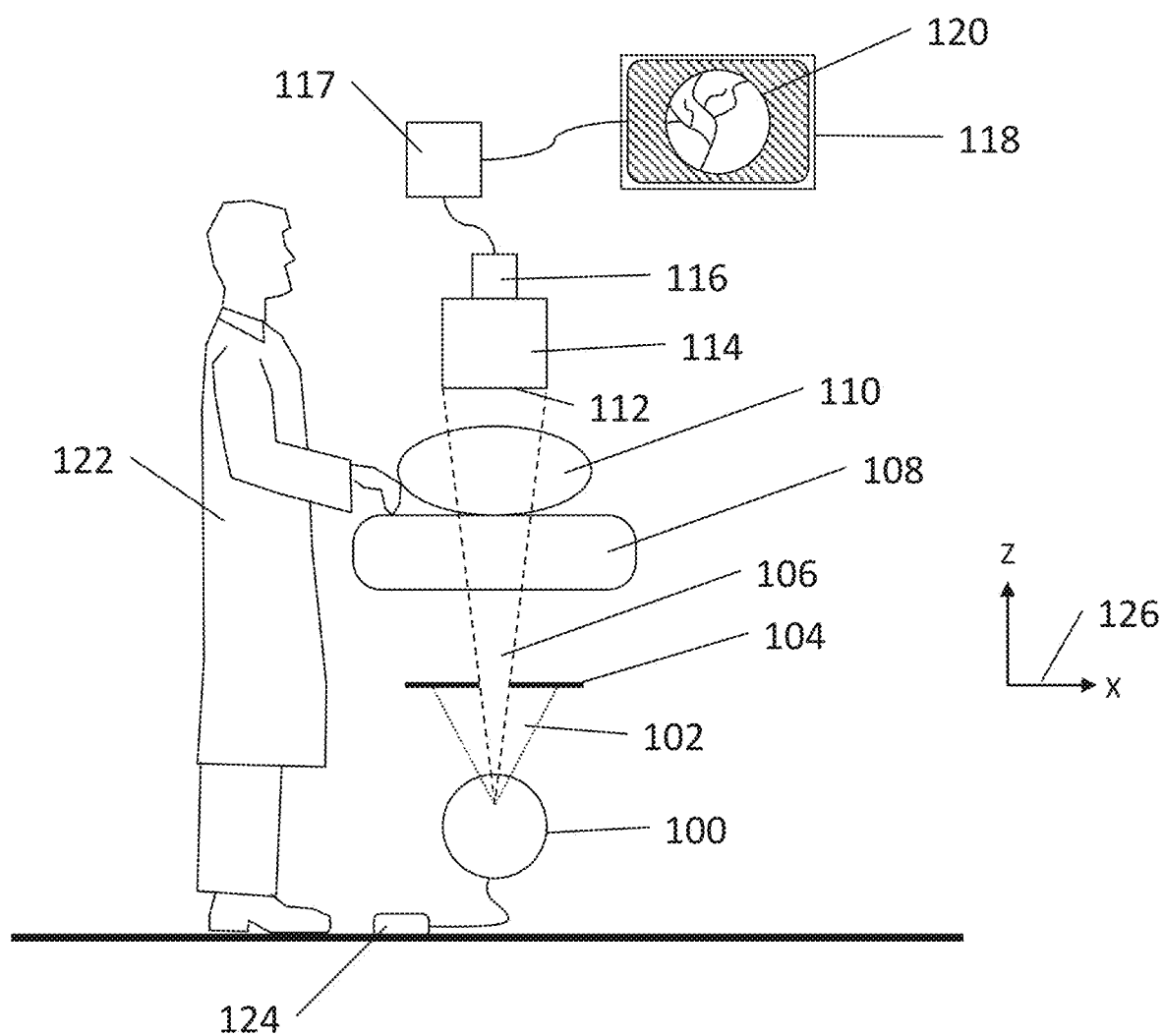
FIG. 1A is a simplified schematic illustration of an exemplary layout of a multiple frames imaging clinical environment and system.

Reference is made now to FIG. 1A which presents a typical layout of a multiple frames imaging clinical environment.

X-ray tube 100 generates x-ray radiation 102 directed upward occupying a relatively large solid angle towards a collimator 104. Collimator 104 blocks a part of the radiation allowing a smaller solid angle of radiation to continue in the upward direction, go through bed 108 that is typically made of material that is relatively transparent to x-ray radiation and through patient 110 who is lying on bed 108. Part of the radiation is absorbed and scattered by the patient and the remaining radiation arrives at the typically round input area 112 of image intensifier 114. The input area of the image intensifier is typically in the order of 300 mm in diameter but may vary per the model and technology. The image generated by image intensifier 114 is captured by camera 116, processed by image processor 117 and then displayed on monitor 118 as image 120.

Although the invention is described mainly in reference to the combination of image intensifier 114 and camera 116 it would be appreciated that both these elements can be replaced by a digital radiography sensor of any technology such as CCD or CMOS flat panels or other technologies such as Amorphous Silicon with scintillators located at plane 112. One such example is CXDI-50RF Available from Canon U.S.A., Inc., Lake Success, N.Y. The term "detector" is used to include any of these technologies, including the combination of any image intensifier with any camera and including any type of a flat panel sensor or any other device converting x-ray to electronic signal.

The terms "area" and "region" are used alternatively in the detailed description of the invention and they mean the same and are used as synonyms.

The term "x-ray source" is used to provide a wide interpretation for a device having x-ray point source that does not necessarily have the shape of a tube. Although the term x-ray tube is used in the examples of the invention in convention with common terminology in the art, it is represented here that the examples of the invention are not limited to a narrow interpretation of x-ray tube and that any x-ray source can be used in these examples (for example even radioactive material configured to function as a point source).

Operator 122 is standing by the patient to perform the medical procedure while watching image 120.

The operator has a foot-switch 124. When pressing the switch, continuous x-ray radiation (or relatively high frequency pulsed x-ray as explained below) is emitted to provide a cine imaging 120. The intensity of x-ray radiation is typically optimized in a tradeoff of low intensity that is desired to reduce exposure to the patient and the operator and high intensity radiation that is desired to enable a high quality image 120 (high S/N). With low intensity x-ray radiation and thus low exposure of the image intensifier input area, the S/N of image 120 might be so low that image 120 becomes useless.

Coordinate system 126 is a reference Cartesian coordinate system with Y axis pointing into the page and X-Y is a plane parallel to planes such as that of collimator 104 and image intensifier input plane 112.

It is a purpose of the present invention to provide high exposure at the input area of the image intensifier in the desired one or more ROIs that provide therefore a high S/N image there while reducing the exposure of other sections of the image intensifier area, at the cost of lower image quality (lower S/N). With this arrangement the operator can see a clear image in the one or more ROIs and get a good enough image for general orientation in the rest of the image area. It is also a purpose of this invention to provide more complex map of segments in the image where each segment results from a different level of x-ray radiation as desired by the specific application.

According to some embodiments, the x-ray system may include multiple filament elements to generate multiple and simultaneous X Ray beams, a subset of which may be selected and may be configured to modify the x-ray radiation in order to aim at the desired ROIs in the field of view according to the location of the operator's focus of attention.

According to some embodiments, the x-ray system may include a matrix/array of x ray tubes/sources to generate multiple and simultaneous X Ray beams, a subset of which may be selected and may be configured to modify the x-ray radiation in order to aim at the desired ROIs in the field of view according to the location of the operator's focus of attention.

According to some embodiments, the x-ray system may further include rotatable and translatable cathodes and/or anodes to generate multiple and simultaneous X Ray beams, a subset of which may be selected and may be configured to modify the x-ray radiation in order to aim at the desired ROIs in the field of view according to the location of the operator's focus of attention.

Figure 1B:
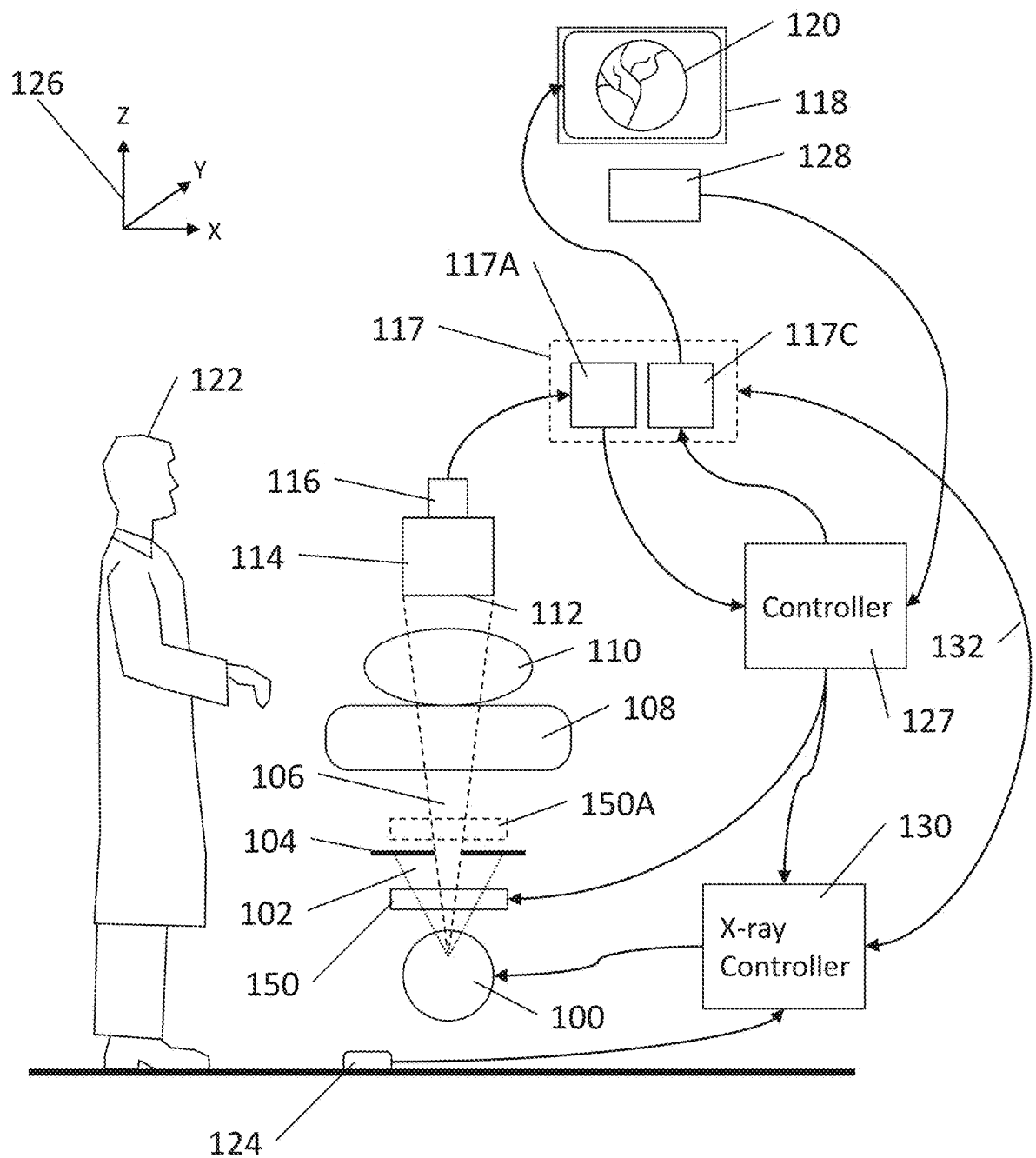
FIG. 1B is an illustration of an exemplary layout of the system of FIG. 1A showing additional details of components of the system example of the invention.

An example of a more detailed layout of a multiple frames imaging clinical environment according to the present invention is described in FIG. 1B. Operator 122 presses foot switch 124 to activate the x-ray. Input device 128 provides indication of one or more ROIs. This information is typically provided relative to monitor 118. This information, the at least one desired center of ROI, may be provided for example in terms of (X,Z) coordinates, in the plane of monitor 118, using coordinate system 126. It would be appreciated that in this example the plane of monitor 118 and therefore also image 120 are parallel to the (X,Z) plane of coordinate system 126. Other coordinate systems are possible, including coordinate systems that are bundled to monitor 118 and rotate with monitor 118 when it is rotated relative to coordinate system 126.

The data from input 128 is provided to controller 127 which is basically a computer, such as any PC computer.

Box 150 in FIG. 1B represents a collimator according to the present invention, for example, the collimator of FIGS. 4 through 11.

Box 150 can be located under collimator 104, above collimator 104 as shown by numerical reference 150A or instead of collimator 104 (not shown in FIG. 1B). The collimators represented by boxes 150 and 150A are controlled by controller 127. X-ray emission is also controlled by controller 127, typically through x-ray controller 130. The collimator partially blocks radiation, depending on the determined at least one desired center of ROI (step 2720). Part of the x-rays are absorbed by the patient 110 (step 2730) and the remaining radiation arrives at the image intensifier 114 (step 2740). In step 2750 the image is intensified and captured by a camera 116 and in step 2760 the captured image is transferred to the image processor 117 and in step 2770 the processed image is displayed on monitor 120.

Image processor 117 may assume many forms and may be incorporated in the current invention in different ways. In the example of FIG. 1B, image processor 117 includes two main sub units: 117A provides basic image correction such as pixel non-uniformity (dark offset, sensitivity, reconstruction of dead pixels etc), 117C provides image enhancement processing (such as noise reduction, un-sharp masking, gamma correction etc). In conventional systems, the image from sub-unit 117A is transferred for further processing in sub-unit 117C. The sub-units of image processor 117 can be supported each by a dedicated hardware but they can also be logical sub-units that are supported by any hardware.

In the example of FIG. 1B the image from camera 116 is corrected by image processing sub-unit 117A and then transferred to controller 127. Controller 127 processes the image as required from using any of the collimators represented by box 150 and returns the processed image to sub-unit 117C for image enhancement.

It would be appreciated that the image processing of controller 127 does not have to take place in controller 127 and it can be executed by a third sub-unit 117B (not shown in FIG. 1B) located between 117A and 117C. Sub-unit 117B can also be only a logical process performed anywhere in image processor 117.

It would also be appreciated that x-ray controller 130 is presented here in the broad sense of system controller. As such it may also communicate with image processor 117 to determine its operating parameters and receive information as shown by communication line 132, It may control image intensifier 114, for example for zoom parameters (communication line not shown), it may control camera 116 parameters (communication line not shown), it may control the c-arm and bed position (communication line not shown) and it may control x-ray tube 100 and collimator 104 operation parameters (communication line not shown).

There may be a user interface for operator 122 or other staff members to input requests or any other needs to x-ray controller 130 (not shown).

Figure 3:
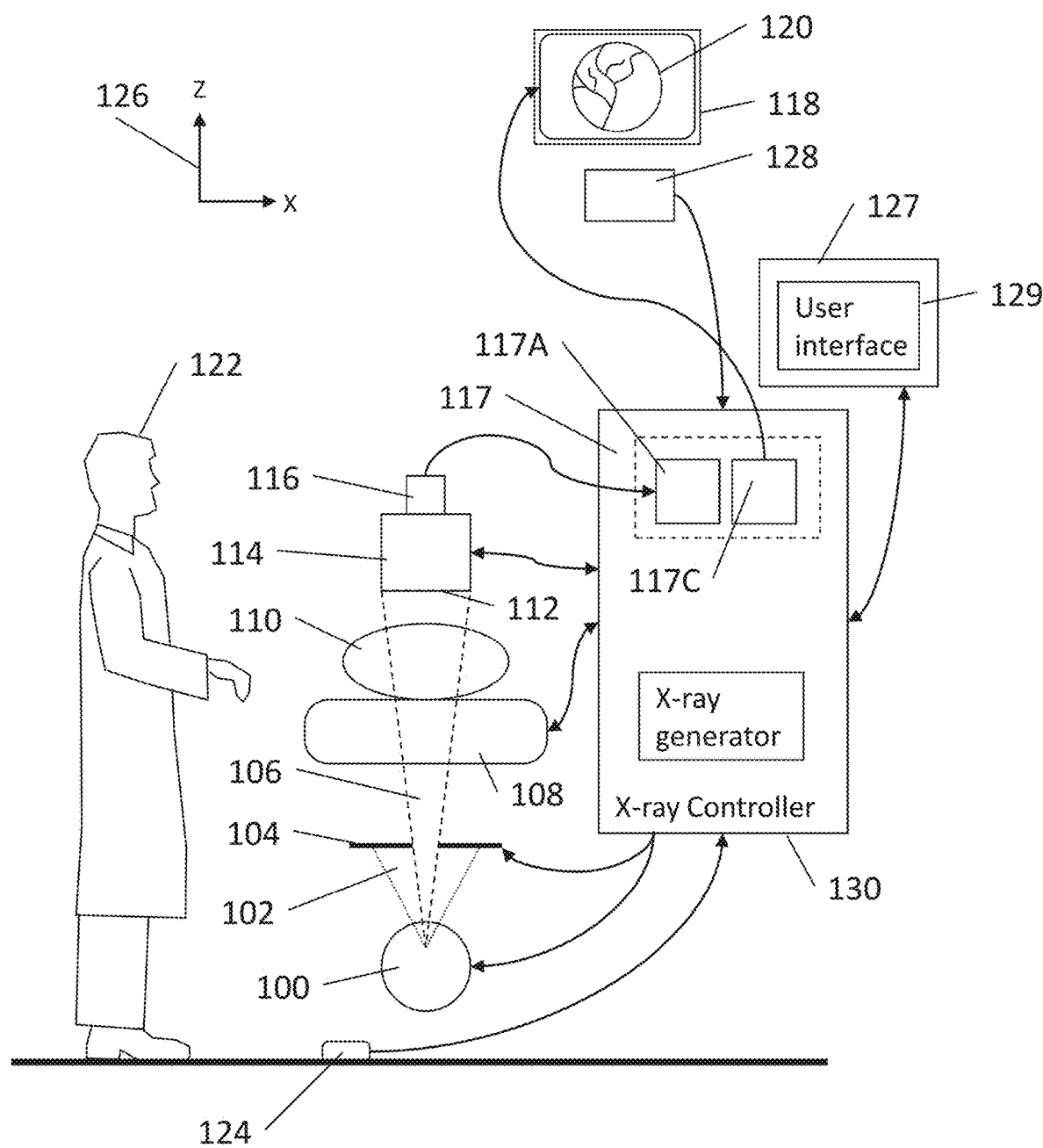
FIG. 3 is a simplified schematic illustration of an exemplary layout of a multiple frames imaging clinical environment and system with the addition of an input device.

Physically, part or all of image processor 117, controller 127 and x-ray generator (the electrical unit that drives x-ray tube 100) may all be included in x-ray controller 130. X-ray controller 130 may contain one or more computers and suitable software to support the required functionality. An example for such a system with an x-ray controller is mobile c-arm OEC 9900 Elite available from GE OEC Medical Systems, Inc., Salt Lake City, Utah USA. It would be appreciated that the exemplary system is not identical to the system of FIGS. 1B and 1s only provided as a general example. Some of these features are shown in FIG. 3.

Figure 2:
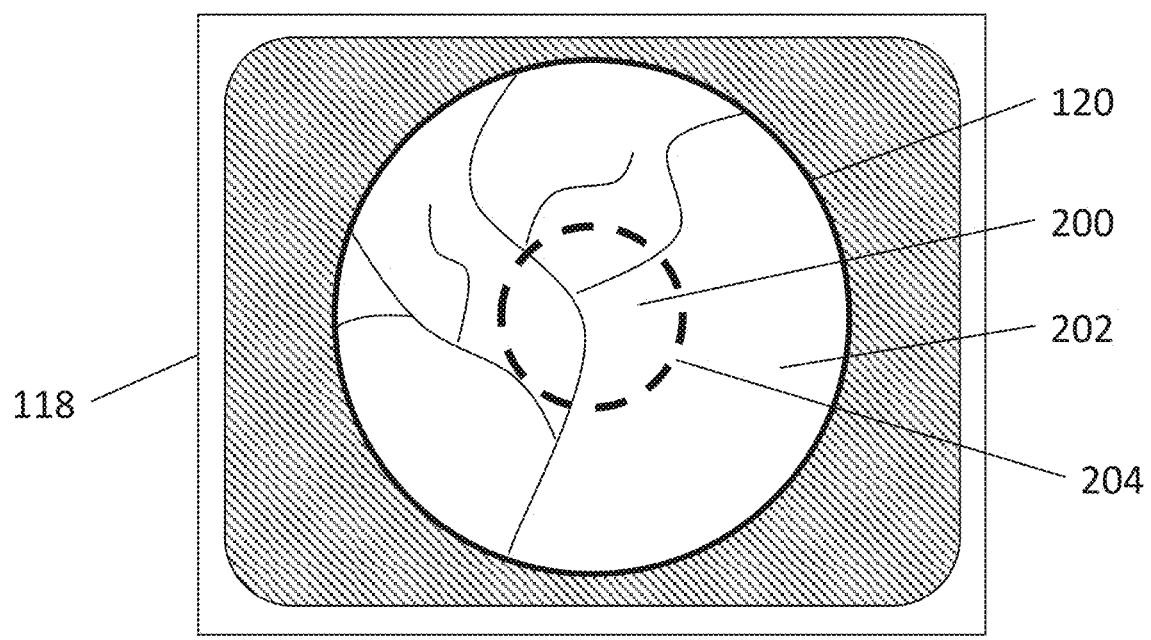
FIG. 2 is a schematic illustration of an exemplary image displayed on a monitor of a multiple frames imaging system.

Reference is made now to FIG. 2 illustrating an example of an image 120 displayed on monitor 118. In this example dashed circle line 204 indicates the border between segment 200 of the image and segment 202 of the image, both segments constitute the entire image 120. In this example it is desired to get a good image quality in segment 200, meaning higher x-ray DPP for segment 200 and it is acceptable to have a lower image quality in segment 202, meaning lower DPP for segment 202.

It would be appreciated that the two segments 200 and 202 are provided here only as one example of an embodiment of the invention that is not limited to this example and that image 120 can be divided to any set of segments by controlling the shape of the apertures in the collimators and mode of motion of the collimators. Such examples are provided below.

It would be appreciated that DPP should be interpreted as the x-ray dose delivered towards a segment representing one pixel of image 120 to generate the pixel readout value used to construct image 120 (excluding absorption by the patient or other elements which are not a part of the system, such as the hands and tools of the operator).

As explained above, pixels with different DPP per the collimator design and use are normalized to provide a proper display-frame. Normalization scheme is made in accordance with the x-ray exposure scheme (i.e., collimator shape, speed and position). Such normalization can be done on the basis of theoretical parameters.

Collimators according to this invention can be mounted on an x-ray system as stand-alone or together with another collimator, for example, such that is designed to limit the x-ray to a part of input area 112 of the image intensifier. Collimators of the invention and other collimators may be placed in any order along the x-ray path. The exposed part of area 112 is the remaining of the superposition of the area of all the collimators in the path of the x-ray block. In the design of such successive arrangement, the distances of each of the collimators from the x-ray source and distance to area 112 needs to be considered with the geometry of the collimators, as described above, to get the desired functionality.

In the present example, the at least one ROI becomes the area used for image optimization. The input device, provides the ROI coordinates of the at least one user on the screen. The ROIs are moved to these coordinates, with a complementary adjustment of the collimator and the optimization is made for the image included in the ROIs.

The image may be optimized per the ROIs' content using any of the above mentioned parameters or any other parameter that modifies the displayed value of a pixel in the image.

Attention is drawn now to FIG. 3 which presents an exemplary system for carrying out the invention.

Typically in x-ray systems, an ROI that is centered in image 120 (such as ROI 200 of FIG. 2) and has a fixed position is used for image analysis and for generating parameters to drive x-ray tube 100 and modify image 120. Parameters such as average value, maximum value and contrast may be calculated for this area. Such parameters are typically used to optimize the x-ray tube operation (such as mA, mAs and KVp).

In this example an input device 127 is used to provide x-ray controller 130 with the ROI coordinates of one or more users 122.

The input device can be any input device that affects the position and/or the shape of the ROI. For example, an eye tracker, a joy-stick, a keyboard, an interactive display, a gesture reading device, a voice interpreter or any other suitable device can be used to determine coordinates relative to image 120, and the ROI position and/or shape changes according to such input.

According to embodiments of the invention, some of the input devices may need a user interface 129.

The user interface can have any display, operated by any computer or tablet, use mouse, trackball or touch-screen, joystick or hand gesture to control the selection of the ROI.

The following examples, demonstrated in FIGS. 4 through 11, present collimators for collimating x-ray radiation in x-ray systems comprising a displayed image of the irradiated area. The systems share the following characteristics:

1. A first part of the image represents the ROI: unfiltered radiation section (100% of the radiation arriving at the collimator plates)
2. A second part of the image is background, where radiation is filtered by the collimator plates (100%>radiation≥0 of the radiation arriving at the collimator plates)
3. The background filter comprises at least three separate filters
4. The background image area comprises at least one point at one filter area of the image and at least one point at a second filter area of the image;
5. There is at least one contour, connecting these two points, wherein, the radiation along the contour encounters essentially the same filtering characteristics (same total filtering thickness for example, of filters of a uniform material composition).

For simplicity, a straight line connecting these two points can be considered for the description, but it should be appreciated that changing filtration characterization along this line due to changing angle of incidence of the radiation (and therefore the effective thickness) is particularly considered, in the scope of this invention, as essentially the same filtering characterization. Same is for any of the contour or the straight line, in regard to non-uniformity of the filter thickness, material homogeneity etc., typically present as a result of manufacturing accuracy limitations, they are all included in "essentially the same" terminology. This includes also filters that are not at the same height or without touching edges etc. They are still coupled but the distance between the edges may change according to the position (incidence angle). This will be explained in more details in conjunction with FIGS. 12D and 12E.

Also, when using the term "uniform" in reference to filtering, the scope of uniform includes such tolerances as described above.

Essentially non-overlapping filters means a design that is intended to support the above system characteristics in at least most of the image area. A small overlapping that, for example results in extra filtering along overlapping edges of two adjacent filters would still be included in "essentially non-overlapping"

Reference is made now to FIG. 4 providing an exemplary collimator 4500 according to the present invention.

Collimator 4500 comprises four plates 4501, 4502, 4503 and 4504 that are opaque or partially transparent to x-ray. In this example we shall assume that each such plate transmits 10% of beam 106 but it would be appreciated that other transmission levels may be contemplated. Plates 4501, 4502, 4503 and 4504 can be made from any suitable material, considering the desired effect of the spectral distribution of the transmitted x-ray beam. For example, copper or aluminum plates can be used.

Dashed circle 106A (FIG. 4A) represents x-ray cone 106 cross section at generally the plane of collimator 4500. Except for a rectangular shaped x-ray beam portion 3510 (FIG. 4A), the rest of the beam intensity is reduced due to plates 4501, 4502, 4503 and 4504.

Eight motors can move plates 4501, 4502, 4503 and 4504 as explained below.

The components of the motorizing elements are detailed in reference to plate 4501. The other 3 plates' mechanisms are analogous.

Motor 4501A drives screw 4501C that moves nut 4501E. Nut 4501E is connected to plate 4501, therefore enables plate 4501 to move in the directions of arrow 4501F.

Motor 4501B drives screw 4501D that moves nut 4501E. Nut 4501E is connected to plate 4501 therefore enables plate 4501 to move in directions of arrow 4501G.

Hence, each plate can move as indicated by dual-head arrows for each plate, independently of the other plates. An example of possible arrangement of nut 4501E is shown in FIG. 4.1. Rails 4505A may be used to support the plates and enable motion. Motors 4501A and 4501B slide freely on the rails 4505A according to the mentioned directions.

It would be appreciated that the specific motion mechanism described herein is provided to explain the invention and that the scope of the invention is not limited to this motion mechanism.

To create a rectangular ROI each one of two adjacent edges of a filter (plate) is parallel and in contact with the edge of a neighboring filter as demonstrated in FIG. 4.

The collimator 4500 is based on "active coupling", meaning the controller of the motors has to ensure coupling of the plates where coupling of two plates means they are in contact along at least a part of an edge.

As mentioned above, each plate is able to move independently but in order to prevent radiation penetration between the plates the controller ensures that when a plate moves in direction perpendicular to a coupling line, the adjacent plate coupled along this line moves with it and thus coupling is maintained. Namely, when one motor needs to be moved, the controller may move other motors as well, to maintain plates coupling.

It would be appreciated that coupling is not required at all times and it is typically preferred to have the coupling at least when radiation is turned on.

It is appreciated that a circular image/circular cone shape x-ray beam is only an example. The x-ray beam and the image may be rectangular or any other shape, depending on the c-arm and collimator setup.

Figure 4A:
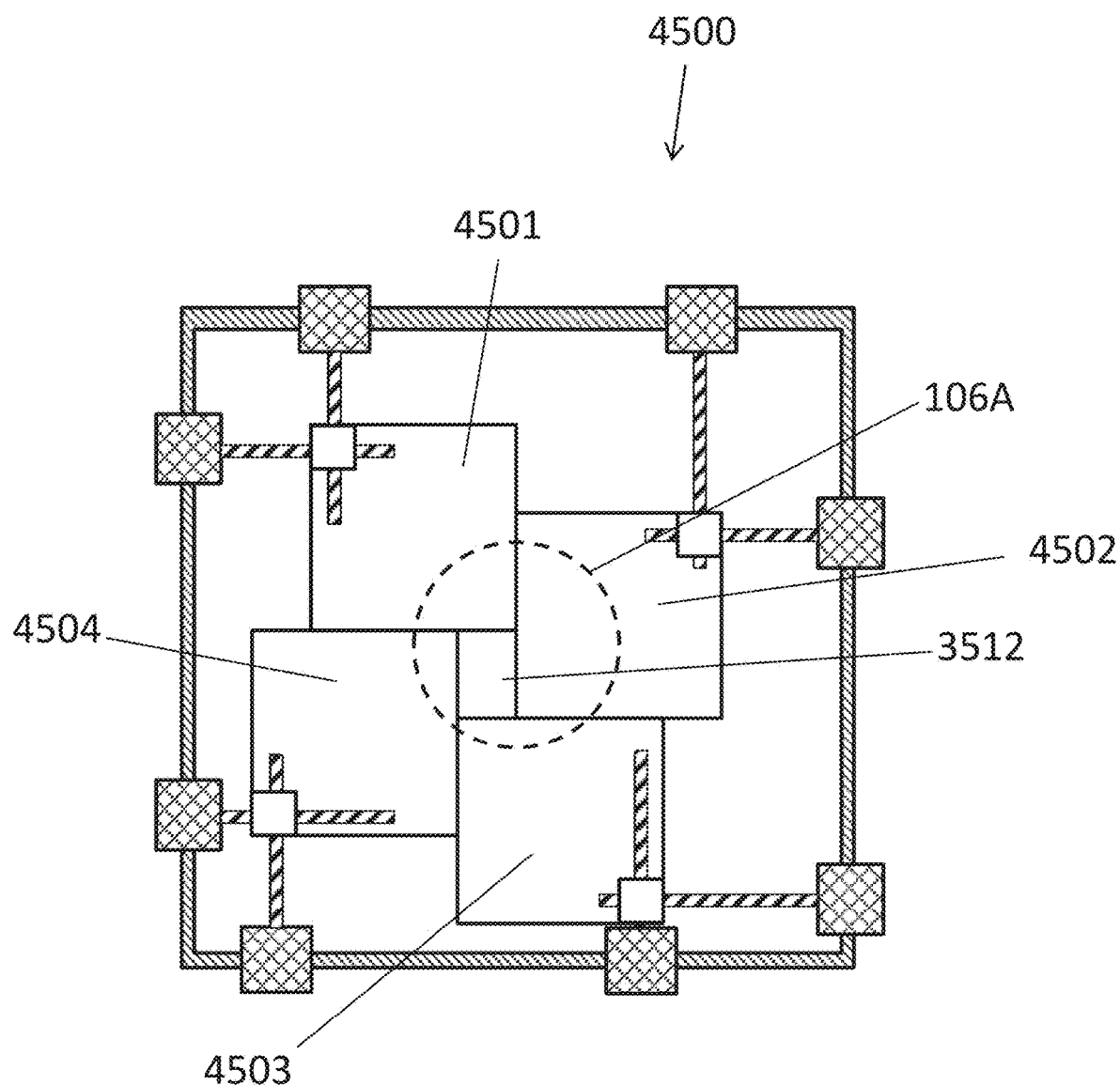
FIG. 4A is a top view of the collimator of FIG. 4 with the ROI at an off-center location.

In the example of FIG. 4A aperture 3512 is in the region of beam 106 (as shown by the beam cross section 106A) and has a certain size dictated by the required ROI. FIG. 4A demonstrates an adjustment of plates 4501, 4502, 4503 and 4504 in order to create the required aperture for providing radiation to the ROI that is different from the ROI example shape of FIG. 4.

With this example of collimator 4500 therefore ROI 3602 of image 120 (FIG. 5) cannot only be moved across the area of image 120 to the desired location but also the size and aspect ratio of the ROI can be changed as desired, to compensate for zoom in image intensifier 114 (FIG. 1A) or for other reasons.

Figure 5:
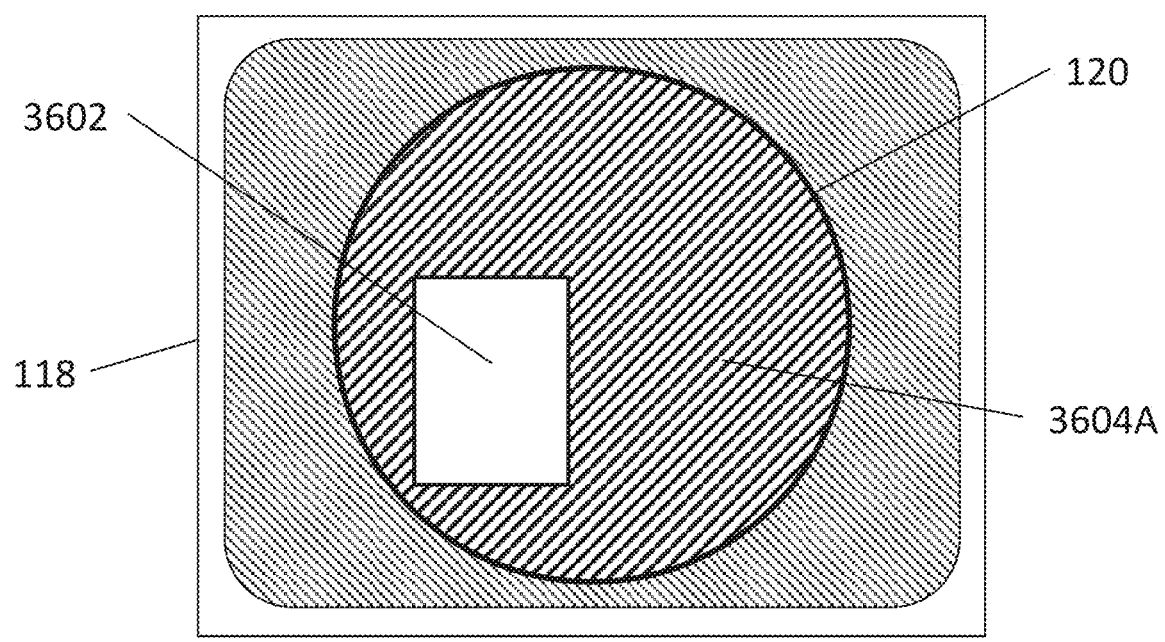
FIG. 5 illustrates the x-ray intensity distribution in different areas of the image when the ROI is at the center.

Reference is made now to FIG. 5, illustrating the x-ray intensity distribution in different areas of image 120 when the image ROI 3602 is in the position resulting from mechanical ROI 3512 presented in FIG. 4A. In this example there is no object (patient) between collimator 4500 and input area 112 so, ideally, without additional conventional collimator blocking radiation, the x-ray radiation over input area 112, outside of the ROI, would be uniform (up to specific system inherent uniformity limitations). In this example, as a result of collimator 4500 the area of image 120 is divided into two intensity areas: 3602, the ROI, where the original 100% intensity is and 3604A where the intensity is 10% of that at the ROI.

The above described methods to correct background are fully applicable to correct the background 3604A of the present example.

It would be appreciated therefore that the current example can be used together with the above described correction methods.

Figure 6:
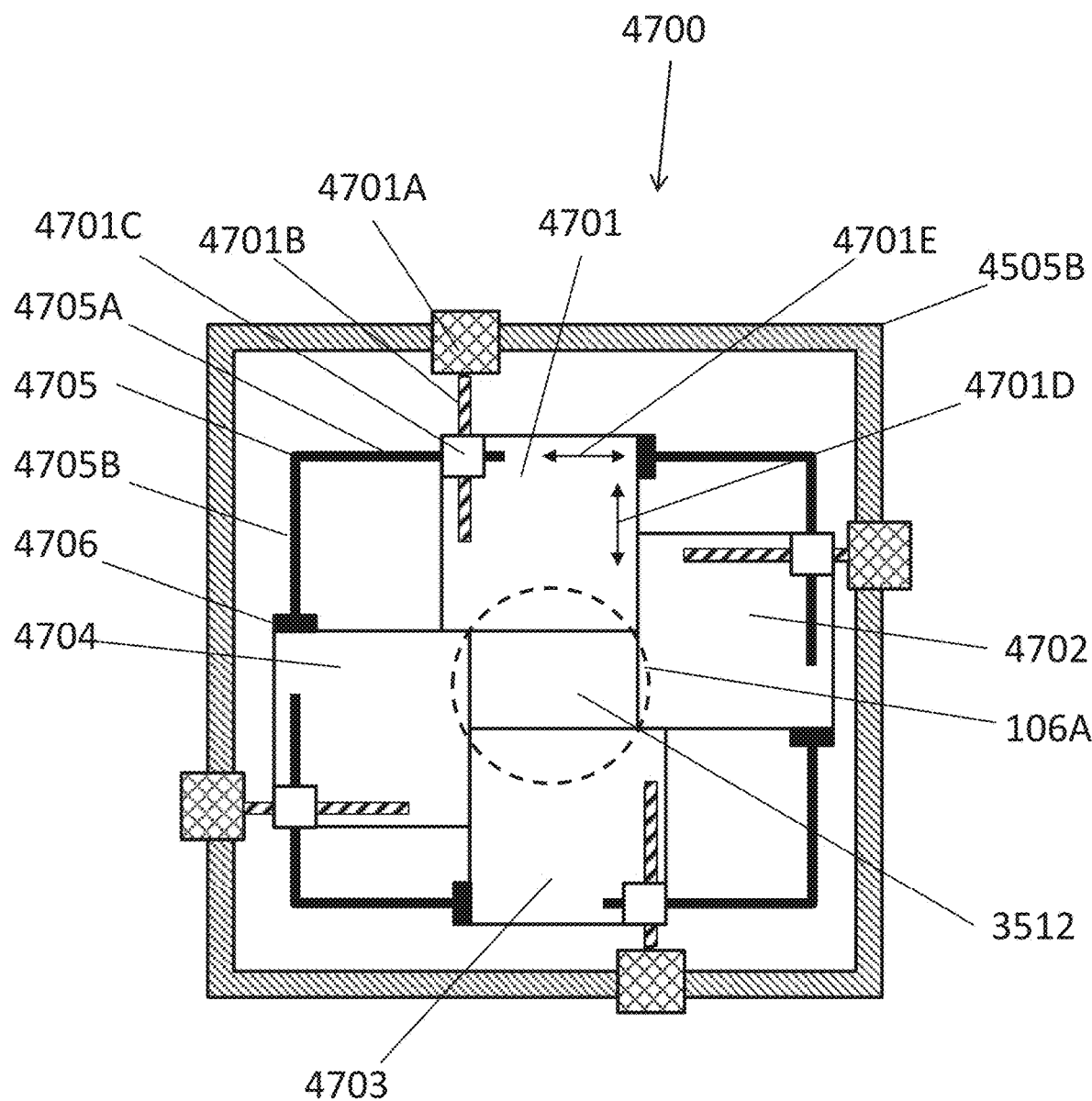
FIG. 6 is a top view of another example of a collimator constructed of four partially x-ray transparent essentially non-overlapping plates with the ROI at the center.

Reference is made now to FIG. 6 providing an example of collimator 4700 according to the present invention.

Collimator 4700 uses four motors instead of the eight motors used in the configuration of FIG. 4.

The components of the motorizing elements are detailed in reference to plate 4701. The other 3 plates' mechanisms are analogous.

Motor 4701A drives screw 4701B that moves nut 4701C. Nut 4701C is connected to plate 4701, therefore enables plate 4701 to move in the directions of arrow 4701D.

An "L" shaped coupler 4705 connects plates 4701 and 4704 wherein nut 4701C slides on the coupler side 4705A and plate 4704 is fixedly connected to the other side 4705B of the coupler via a connector 4706.

Therefore, as plate 4701 moves in the directions of arrow 4701D, plate 4704 moves with it in the same direction but in order to move in the directions of arrow 4701E, plate 4702 moves and moves plate 4701 with it.

Hence, according to this configuration, a single plate cannot move without causing movement of another plate.

The collimator 4700 is based on "passive coupling" meaning the "L" shaped couplers ensure coupling of the plates by forcing two adjacent edges of neighboring plates to maintain their relative positions by sliding along each other.

The four motors slide freely on the rails 4505B according to the mentioned directions.

It would be appreciated that some of the plates may be movable by one motor and a coupler and some plates may be movable by two motors.

In that case an "active coupling" is needed in addition to the "passive coupling".

It would be appreciated that the specific motion mechanism described herein is provided to explain the invention and that the scope of the invention is not limited to this motion mechanism.

To create a rectangular ROI each of two adjacent edges of a filter (plate) is parallel and in contact with the edge of a neighboring filter.

Figure 6A:
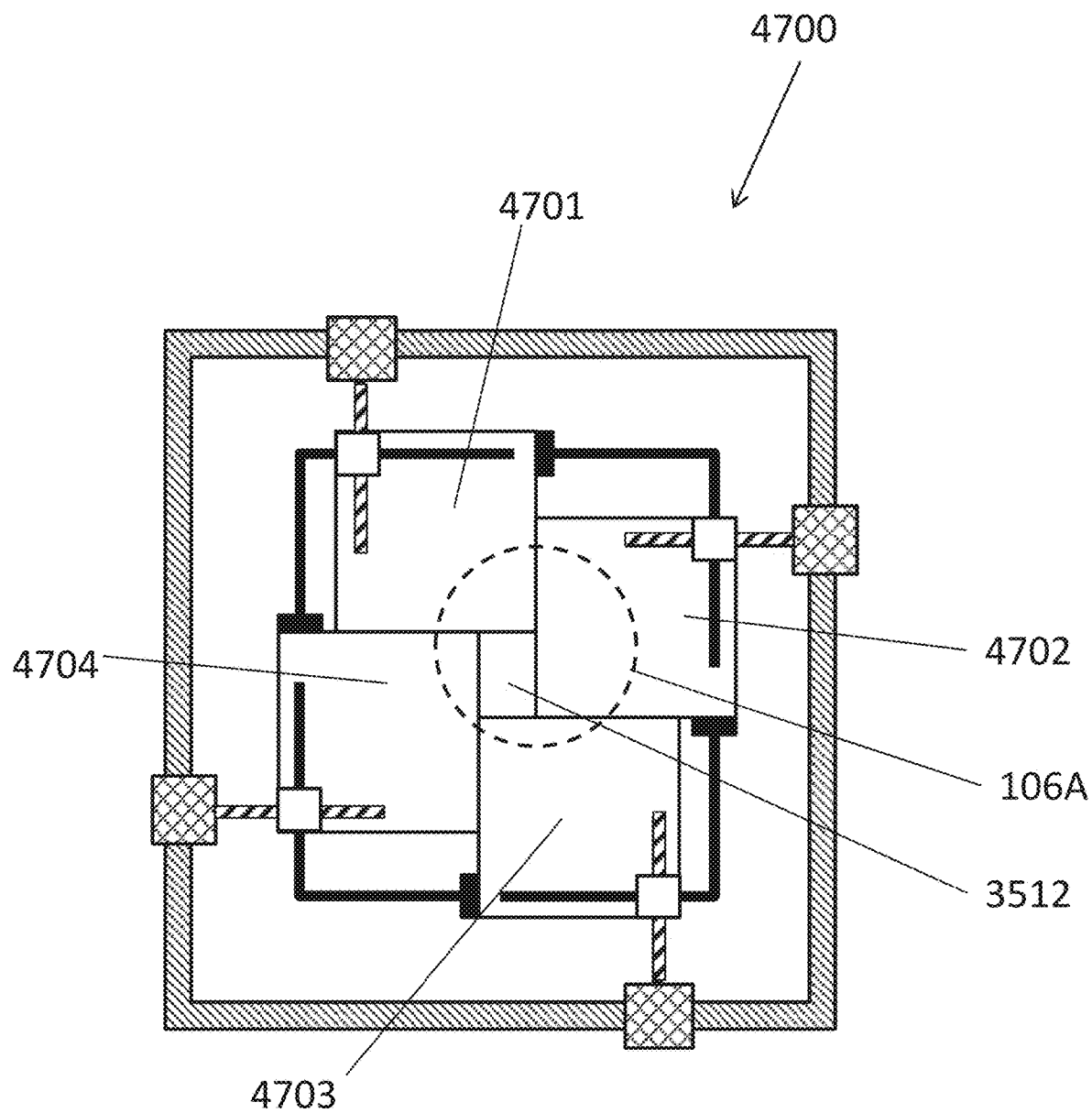
FIG. 6A is a top view of the collimator of FIG. 6 with the ROI at an off-center location.

Reference is made now to FIG. 6A.

FIG. 6A demonstrates an adjustment of plates 4701, 4702, 4703 and 4704 in order to create the aperture for providing radiation to the ROI.

With this example of collimator 4700 therefore the ROI of image 120 can not only be moved across the area of image 120 to the desired location but also the size and aspect ratio of the ROI can be changed as desired, to compensate for zoom in image intensifier 114 or for other reasons.

Figure 7:
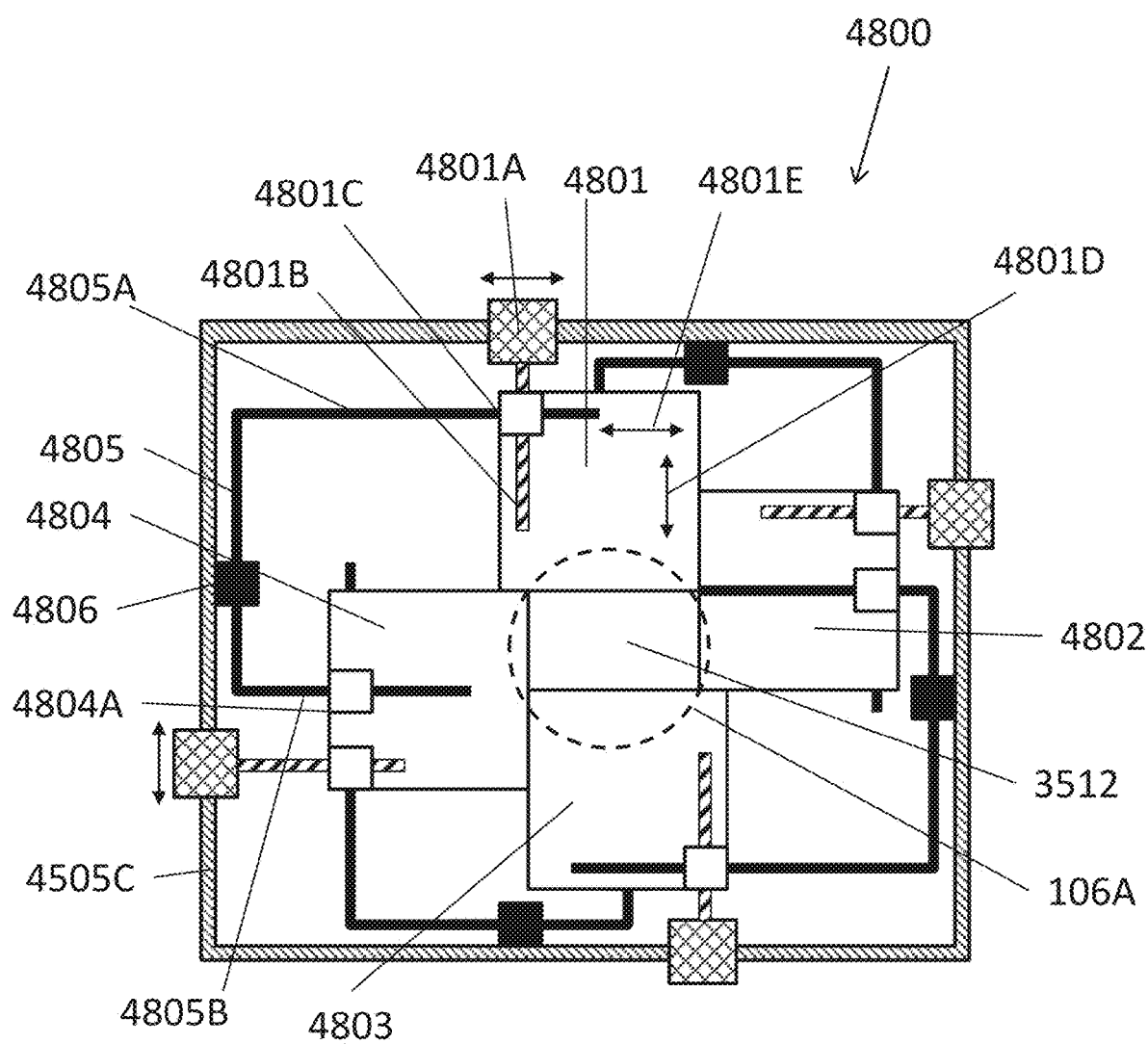
FIG. 7 is a top view of another example of a collimator constructed of four x-ray partially transparent essentially non-overlapping plates with the ROI at the center.

Reference is made now to FIG. 7 providing an example of collimator 4800 of the present invention.

Collimator 4800 also uses four motors instead of eight.

The components of the motorizing elements are detailed in reference to plate 4801. The other 3 plates' mechanisms are analogous.

Motor 4801A drives screw 4801B that moves nut 4801C. Nut 4801C is connected to plate 4801 therefore enables plate 4801 to move in the directions of arrow 4801D.

A "U" shaped coupler 4805 connects plates 4801 and 4804 wherein nut 4801C slides on the coupler side 4805A and nut 4804A slides on the coupler side 4805B. The connector 4806 is fixedly connected to the rail 4505C and allows the coupler to slide through it.

The "U" shaped coupler dictates the motion limitations and ensures plates' coupling.

Therefore, as plate 4801 moves in the directions of arrow 4801D, plate 4804 moves with it in the same direction but in order to move in the directions of arrow 4801E, plate 4802 moves and moves plate 4801 with it.

Hence, according to this configuration, a single plate cannot move without causing movement of another plate.

The collimator 4800 is based on "passive coupling" meaning the "U" shaped coupler ensures coupling of the plates by forcing two adjacent edges of neighboring plates to maintain their relative positions by sliding along each other. The motors slide freely on the rails 4505C according to the mentioned directions.

It would be appreciated that some of the plates may be movable by one motor and a coupler and some plates may be movable by two motors.

In that case an "active coupling" is needed in addition to the "passive coupling".

It would be appreciated that the specific motion mechanism described herein is provided to explain the invention and that the scope of the invention is not limited to this motion mechanism.

To create a rectangular ROI each of two adjacent edges of a filter (plate) is parallel and in contact with the edge of a neighboring filter.

Figure 7A:
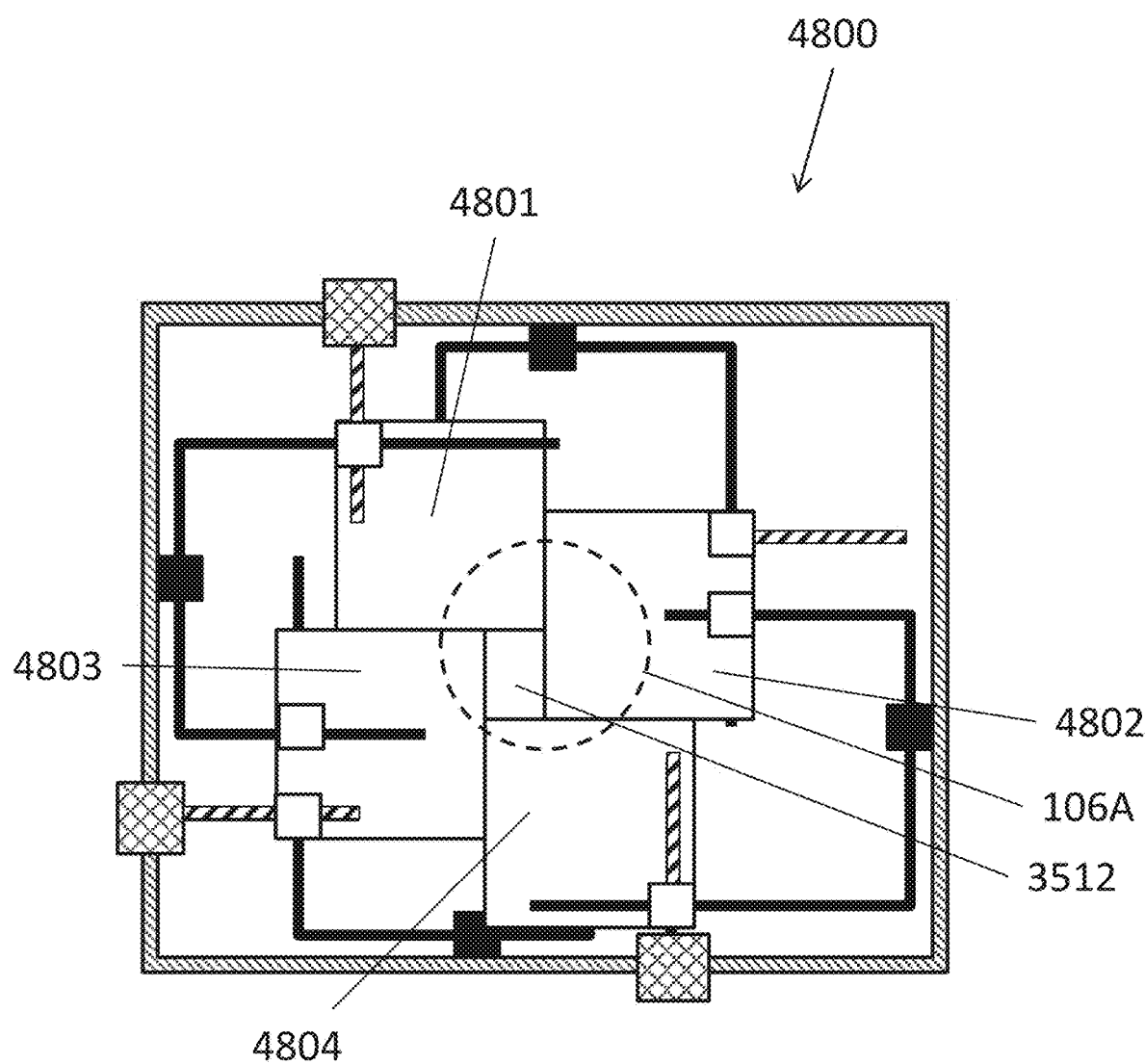
FIG. 7A is a top view of the collimator of FIG. 7 with the ROI at an off-center location.

Reference is made now to FIG. 7A.

In the example of FIG. 7A aperture 3512 is at the region of beam 106 (as shown by the beam cross section 106A) and it has a certain size.

FIG. 7A demonstrates an adjustment of plates 4801, 4802, 4803 and 4804 in order to create the aperture for providing radiation to the ROI.

With this example of collimator 4800 therefore the ROI of image 120 can not only be moved across the area of image 120 to the desired location but also the size and aspect ratio of the ROI can be changed as desired, to compensate for zoom in image intensifier 114 or for other reasons.

Figure 11:
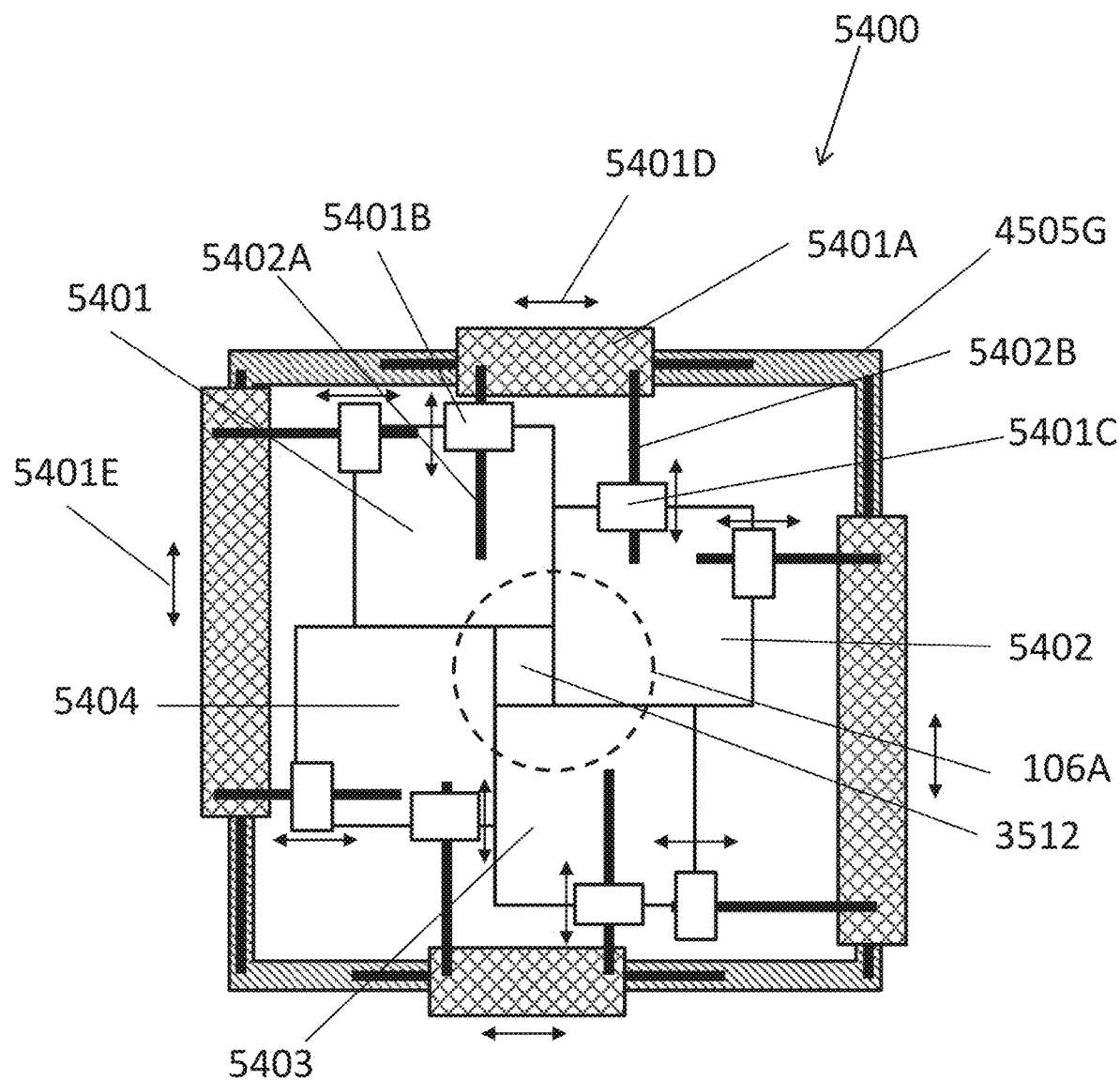
FIG. 11 is a top view of a collimator constructed of four x-ray partially transparent essentially non-overlapping plates with the ROI at an off-center location.

Reference is made now to FIG. 11 providing an example of collimator 5400 of the present invention.

Collimator 5400 also uses four motors instead of eight.

The components of the motorizing elements are detailed in reference to plate 5401. The other 3 plates' mechanisms are analogous.

Motor 5401A moves on rail 4505G and connects plates 5401 and 5402 via couplers 5402A and 5402B and nuts 5401B and 5401C respectively, thereby enabling plate 5401 to move in the directions of arrow 5401D.

The nuts 5401B and 5401C slide freely on the couplers 5402A and 5402B respectively. The couplers 5402A and 5402B dictate the motion limitations and ensure plates' coupling.

Therefore, as plate 5401 moves in the directions of arrow 5401D, plate 5402 moves with it in the same direction but in order to move in directions of arrow 5401E, plate 5404 moves and moves plate 5401 with it.

Hence, according to this configuration, a single plate cannot move without causing movement of another plate.

The collimator 5400 is based on "passive coupling" meaning the couplers 5402A and 5402B ensure coupling of the plates by forcing two adjacent edges of neighbor filters to maintain the distance between them by sliding along each other.

The motors slide on the rails 4505G according to the mentioned directions.

It would be appreciated that the specific motion mechanism described herein is provided to explain the invention and that the scope of the invention is not limited to this motion mechanism.

To create a rectangular ROI each of two adjacent edges of a filter (plate) is parallel and in contact with the edge of a neighboring filter.

Figure 11A:
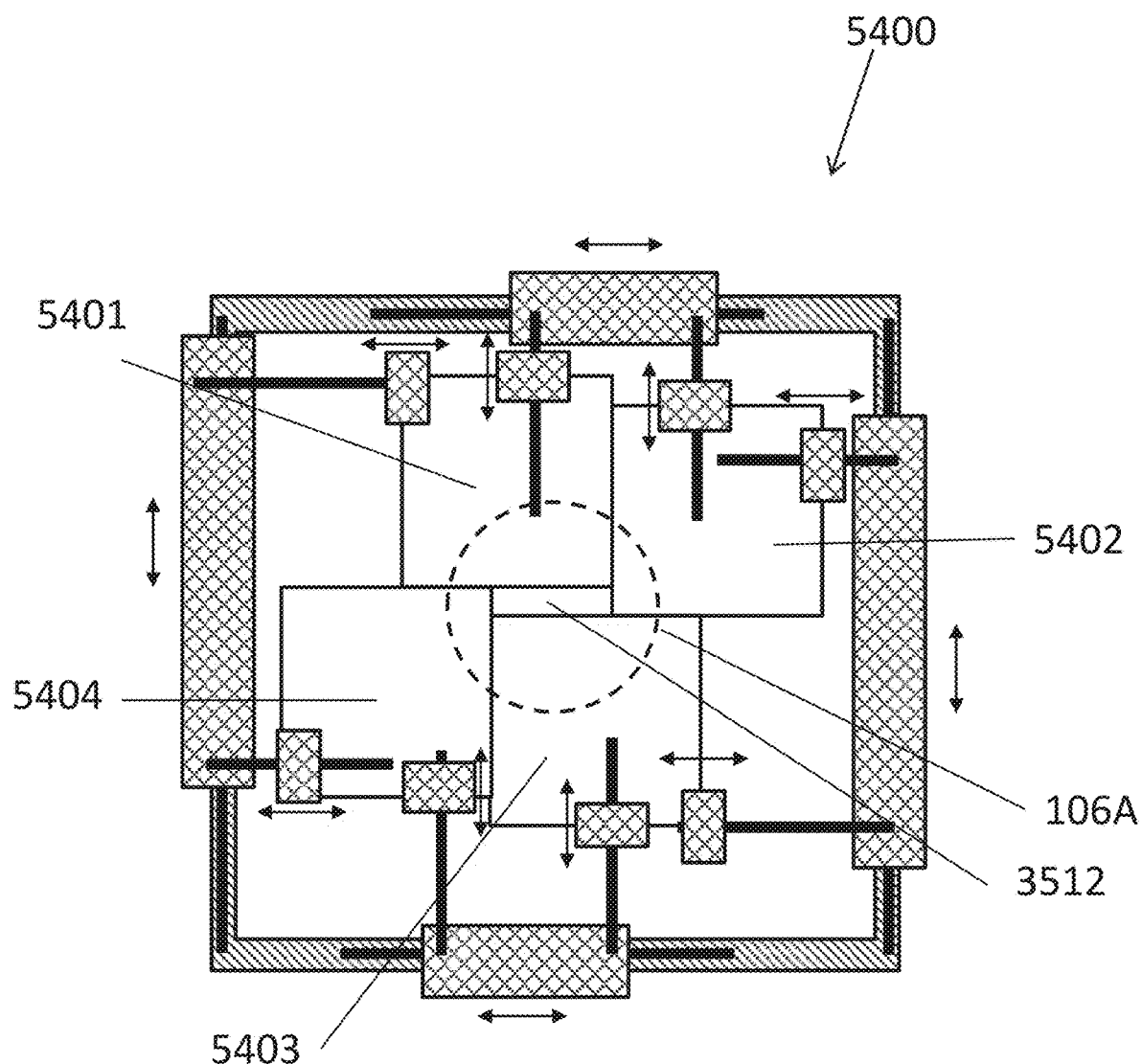
FIG. 11A is a top view of the collimator of FIG. 11 with the ROI at the center.

Reference is made now to FIG. 11A.

In the example of FIG. 11A aperture 3512 is at the region of beam 106 (as shown by the beam cross section 106A) and it has a certain size.

FIG. 11A demonstrates an adjustment of plates 5401, 5402, 5403 and 5404 in order to create the aperture for providing radiation to the ROI.

With this example of collimator 5400 therefore the ROI of image 120 can not only be moved across the area of image 120 to the desired location but also the size and aspect ratio of the ROI can be changed as desired, to compensate for zoom in image intensifier 114 or for other reasons.

Figure 8:
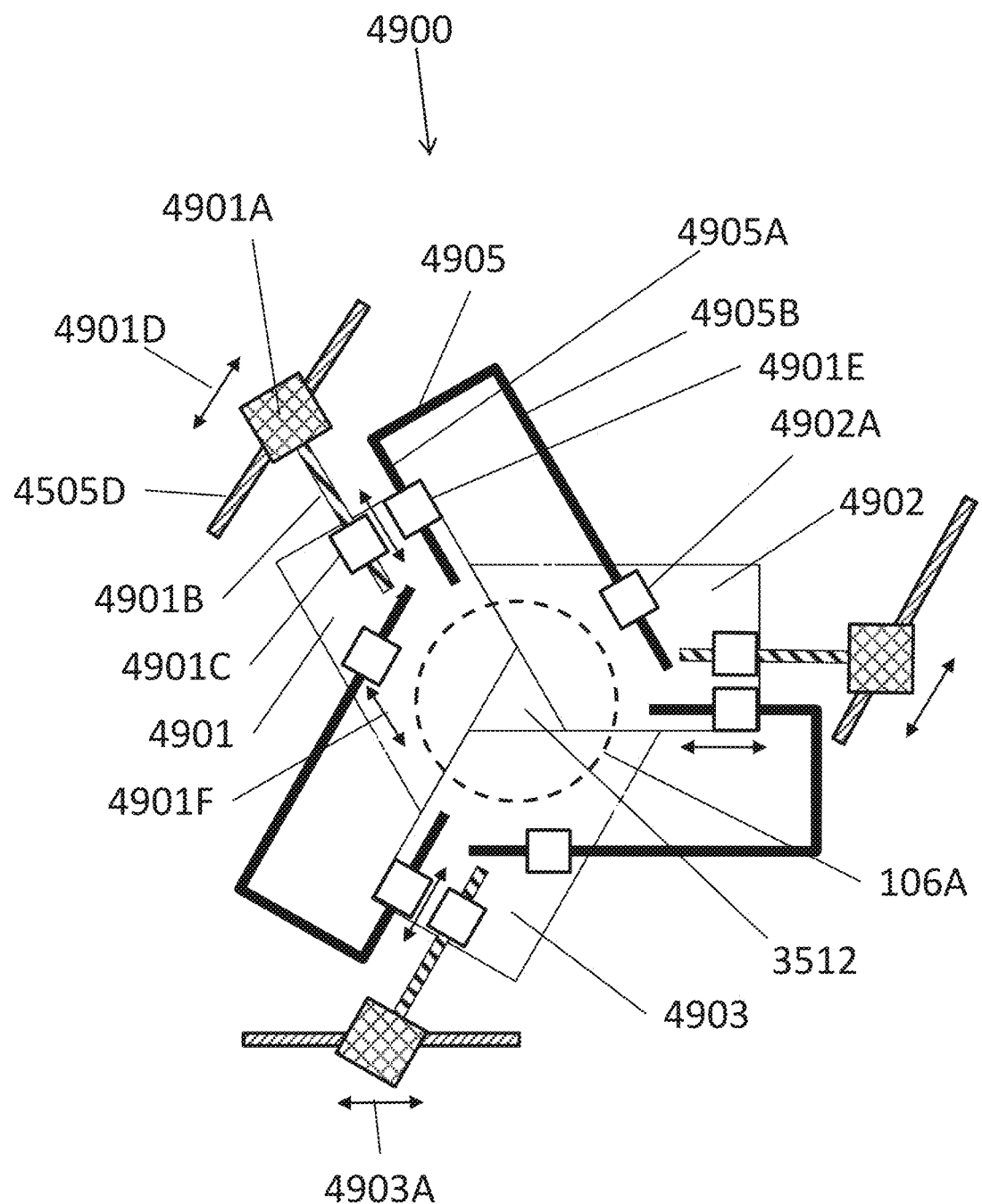
FIG. 8 is a top view of another example of a collimator constructed of three x-ray partially transparent essentially non-overlapping plates with the ROI at the center.

Reference is made now to FIG. 8 providing an example of collimator 4900 of the present invention.

Collimator 4900 has three filters (plates) and uses three motors.

The components of the motorizing elements are detailed in reference to plate 4901. The other two plates' mechanisms are analogous.

Motor 4901A drives screw 4901B that moves nut 4901C. Nut 4901C is connected to plate 4901 therefore enables plate 4901 to move in the directions of arrow 4901F.

A "U" shaped coupler 4905 connects plates 4901 and 4902 wherein nut 4901E slides on the coupler side 4905A and nut 4902A slides on the coupler side 4905B.

The "U" shaped coupler dictates the motion limitations and ensure plates' coupling.

Therefore, as plate 4901 moves in directions of arrow 4901F, plate 4903 moves with it in the directions of arrow 4903A but in order to move in the directions of arrow 4901D, plate 4902 moves in the directions of arrow 4903A and moves plate 4901 with it.

Hence, according to this configuration, a single plate cannot move without causing movement of another plate. Therefore, when the controller moves one motor, other motors may need to move.

The collimator 4900 is based on "passive coupling" meaning the couplers 5402A and 5402B ensure coupling of the plates by forcing two adjacent edges of neighbor filters to maintain the distance between them by sliding along each other.

The motors slide freely on the rails 4505D according to the mentioned directions.

It would be appreciated that some of the plates may be movable by one motor and a coupler and some plates may be movable by two motors.

In that case an "active coupling" is needed in addition to the "passive coupling".

It would be appreciated that the specific motion mechanism described herein is provided to explain the invention and that the scope of the invention is not limited to this motion mechanism.

Figure 8A:
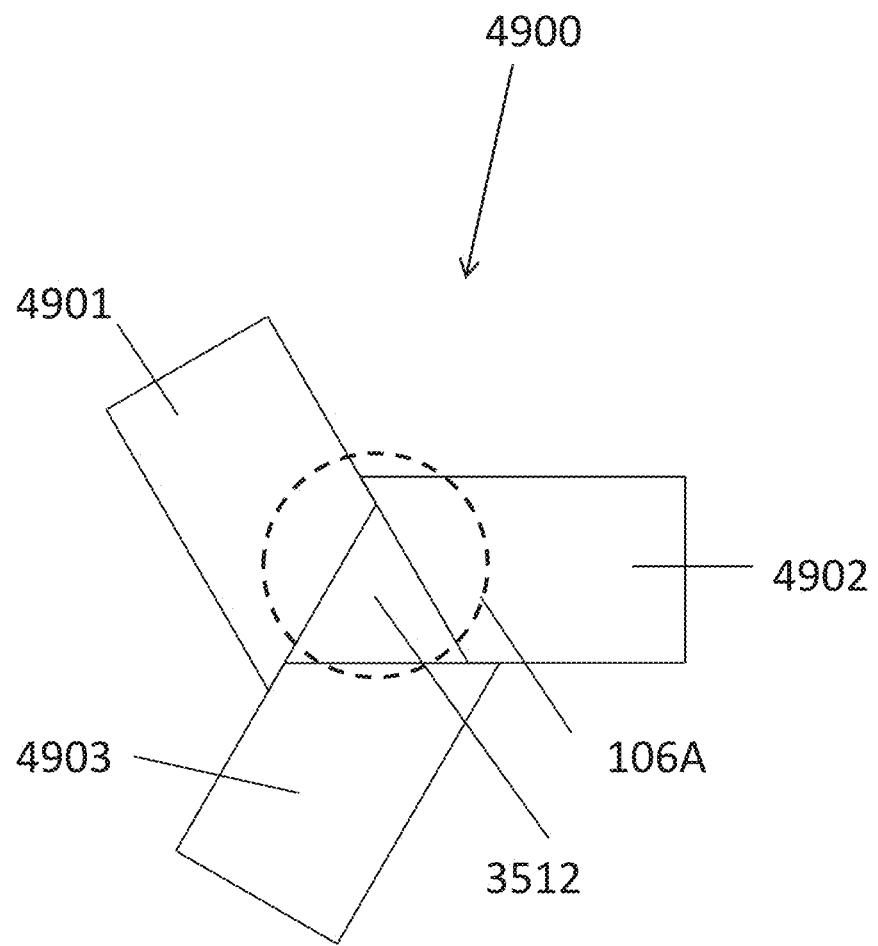
FIG. 8A is a top view of the collimator of FIG. 8 with the ROI at an off-center location.

Reference is made now to FIG. 8A.

FIG. 8A demonstrates an adjustment of plates 4901, 4902 and 4903 in order to create the aperture for providing radiation to the ROI.

With this example of collimator 4900 therefore the ROI of image 120 can not only be moved across the area of image 120 to the desired location but also the size and aspect ratio of the ROI can be changed as desired, to compensate for zoom in image intensifier 114 or for other reasons.

Figure 9:
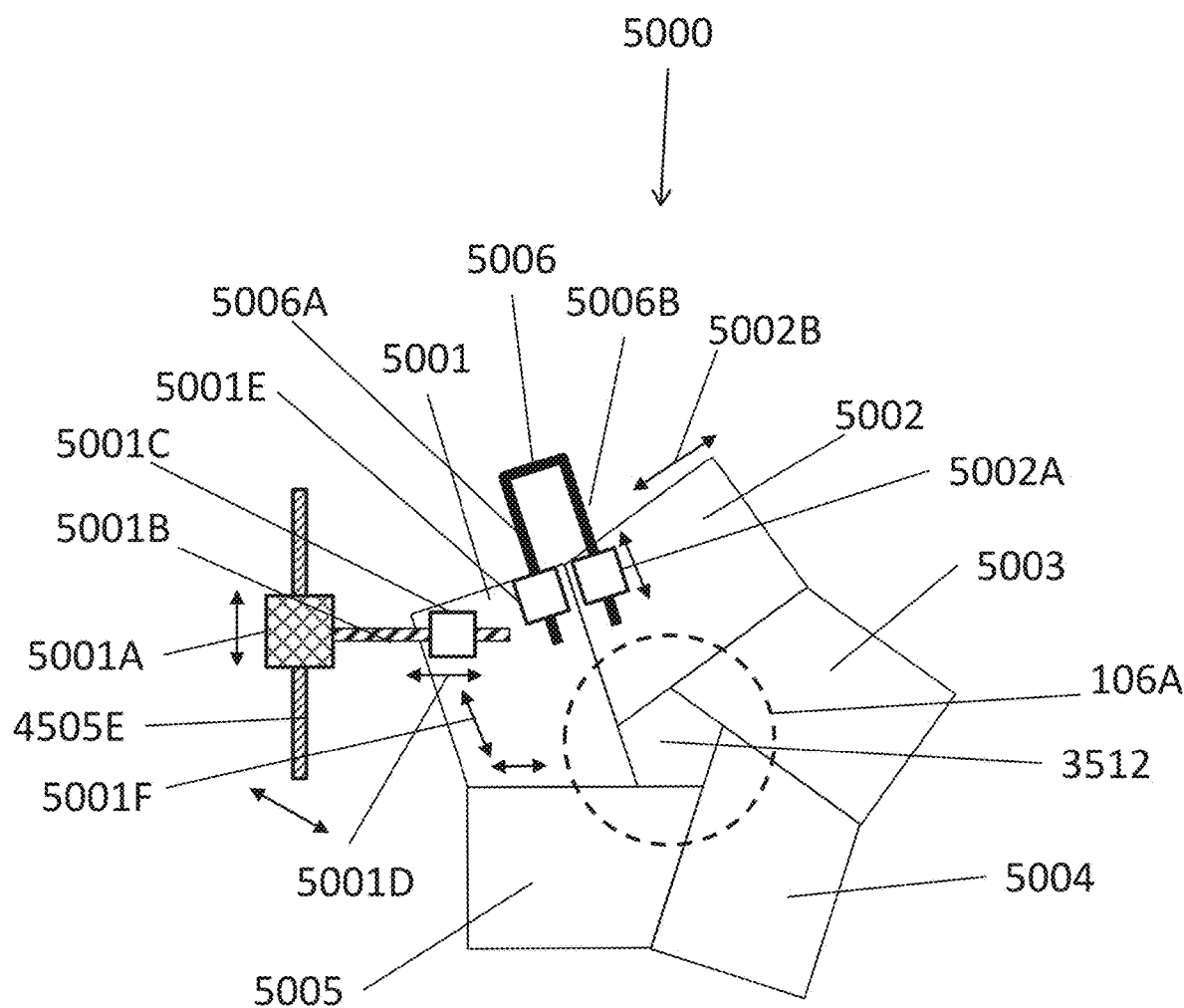
FIG. 9 is a top view of another example of a collimator constructed of five x-ray partially transparent essentially non-overlapping plates with the ROI at the center.

Reference is made now to FIG. 9 providing an example of collimator 5000 of the present invention.

Collimator 5000 has five plates (filters) and uses five motors.

The components of the motorizing elements are detailed in reference to plate 5001. The other four plates' mechanisms are analogous.

Motor 5001A drives screw 5001B that moves nut 5001C. Nut 5001C is connected to plate 5001 thus enabling plate 5001 to move in the directions of arrow 5001D. A "U" shaped coupler 5006 connects plates 5001 and 5002 wherein nut 5001E slides on the coupler side 5006A and nut 5002A slides on the coupler side 5006B.

The "U" shaped coupler dictates the motion limitations and ensure plates' coupling.

Therefore, as plate 5001 moves in directions of arrow 5001D, plate 5002 moves with it in the directions of arrow 5002B but in order to move in the directions of arrow 5001F, plate 5005 moves and moves plate 5001 with it.

Hence, according to this configuration, a single plate cannot move without causing movement of another plate. Therefore, when the controller moves one motor, other motors may need to move.

The collimator 5000 is based on "passive coupling" meaning the "U" shaped couplers ensure coupling of the plates by forcing two adjacent edges of neighbor filters to maintain the distance between them by sliding along each other.

The motors slide freely on the rails 4505E according to the mentioned directions.

It would be appreciated that some of the plates may be movable by one motor and a coupler and some plates may be movable by two motors.

In that case an "active coupling" is needed in addition to the "passive coupling".

It would be appreciated that the specific motion mechanism described herein is provided to explain the invention and that the scope of the invention is not limited to this motion mechanism.

Figure 9A:
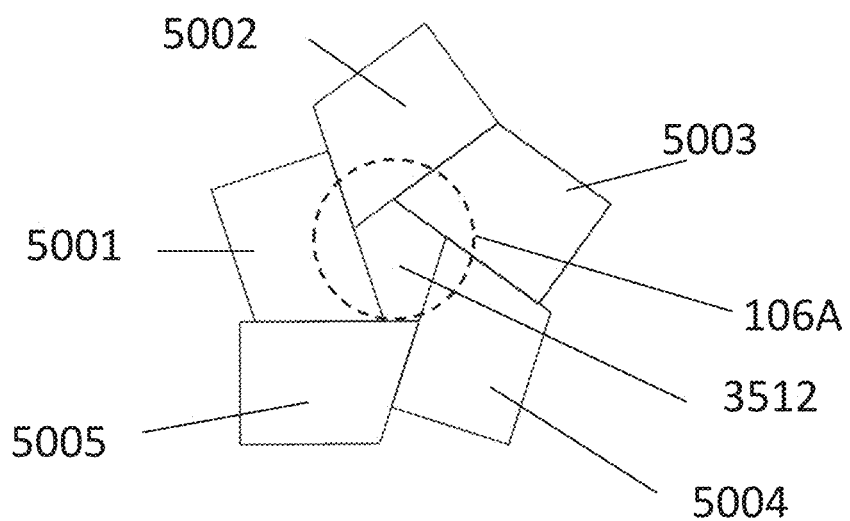
FIG. 9A is a top view of the collimator of FIG. 9 with the ROI at an off-center location.
Figure 9B:
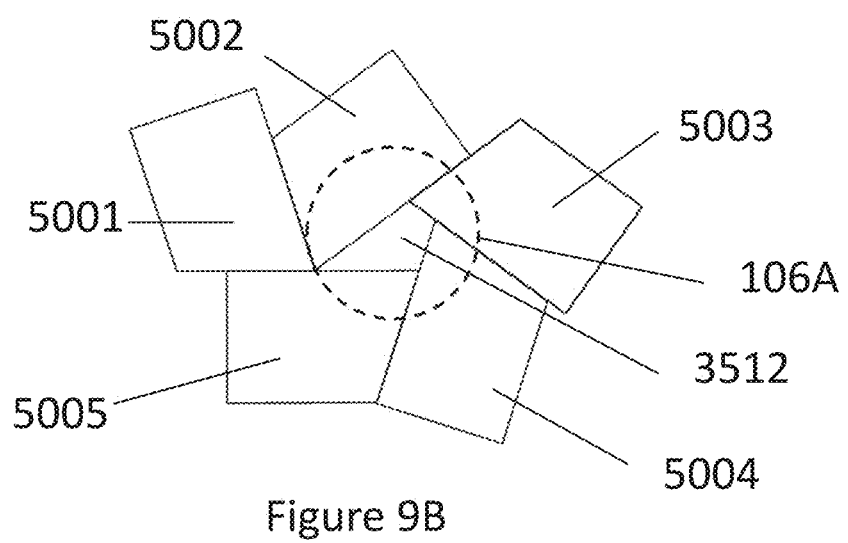
FIG. 9B is a top view of the collimator of FIG. 9 with a different ROI at the center.
Figure 9C:
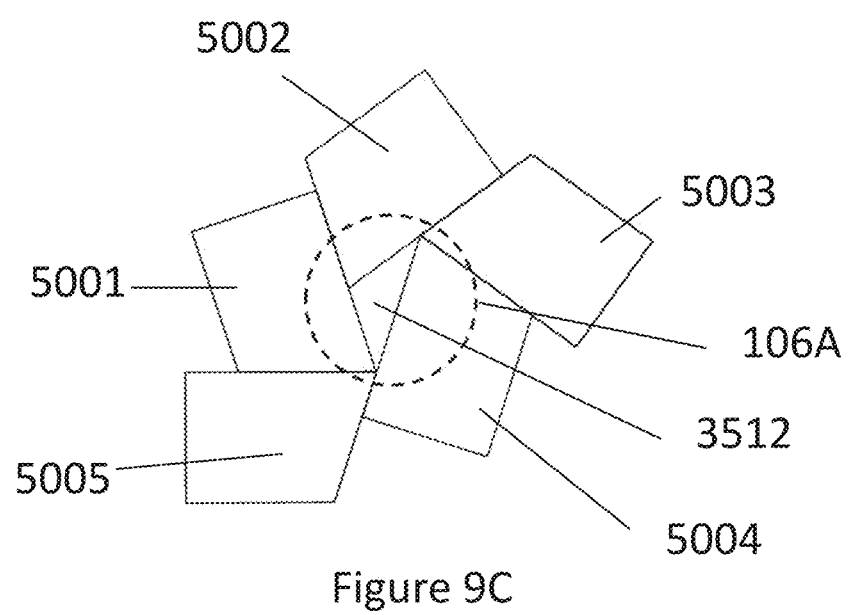
FIG. 9C is a top view of the collimator of FIG. 9 with a different ROI at the center.

Reference is made now to FIG. 9A through 9C.

In the examples of FIGS. 9A, 9B and 9C aperture 3512 is at the region of beam 106 (as shown by the beam cross section 106A) and it has a certain size.

FIG. 9A demonstrates an adjustment of plates 5001, 5002, 5003, 5004 and 5005 in order to create a specific needed pentagonal ROI.

FIG. 9B demonstrates an adjustment of plates 5001, 5002, 5003, 5004 and 5005 in order to create a specific needed quadrangular ROI.

FIG. 9C demonstrates an adjustment of plates 5001, 5002, 5003, 5004 and 5005 in order to create a specific needed triangular ROI.

Figure 10:
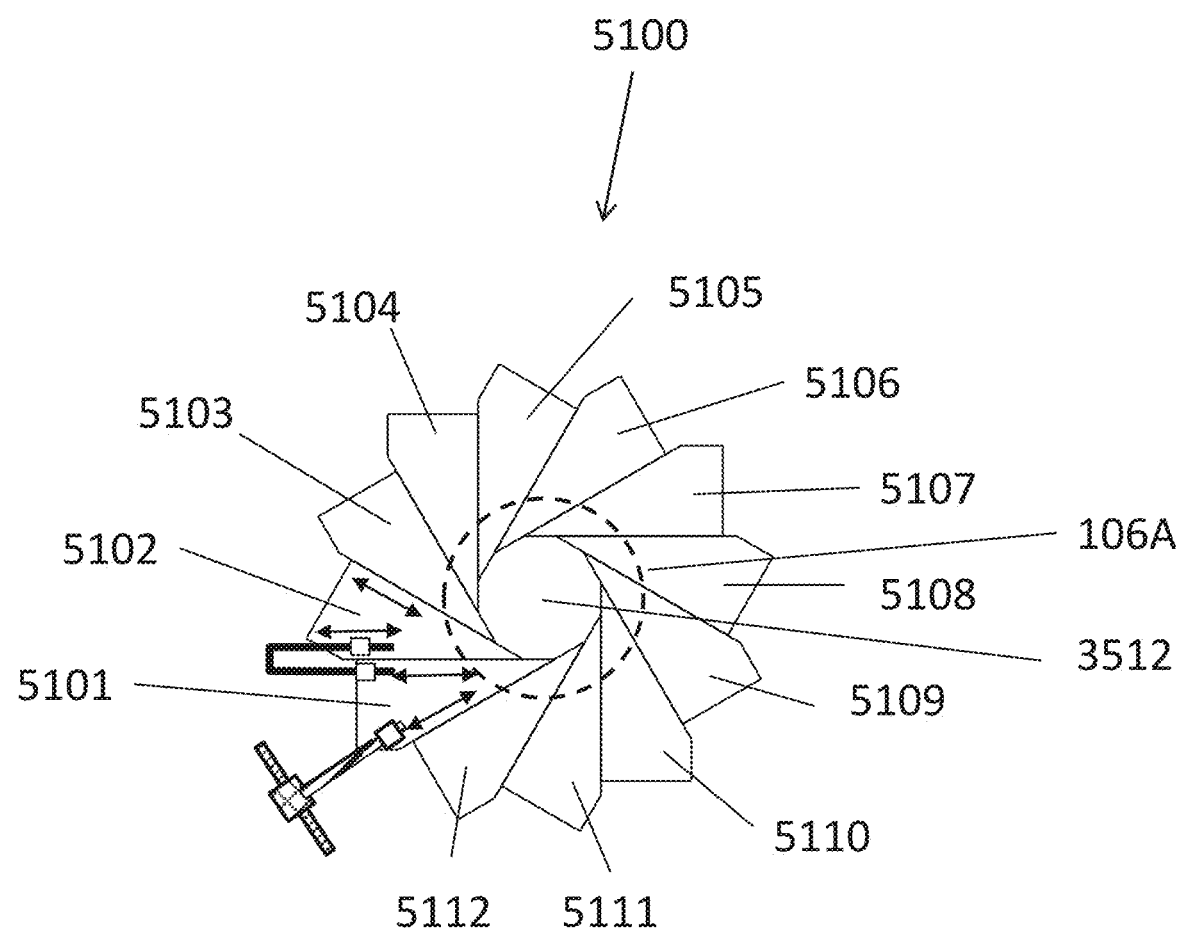
FIG. 10 is a top view of another example of a collimator constructed of twelve x-ray partially transparent essentially non-overlapping plates with the ROI at the center.

Reference is made now to FIG. 10 providing an example of collimator 5100 of the present invention.

Collimator 5100 has twelve plates (filters) and uses twelve motors.

Figure 10A:
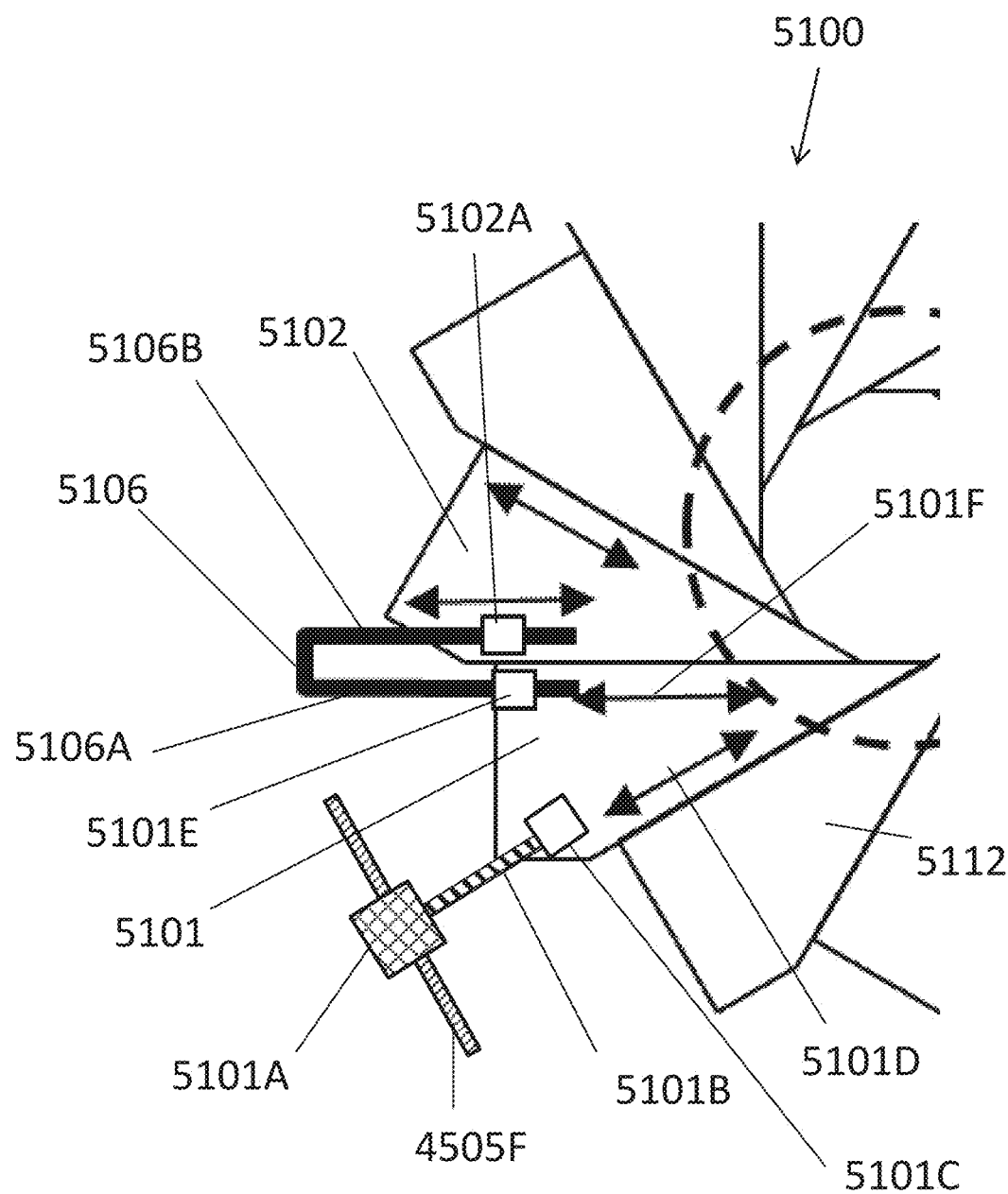
FIG. 10A is a top view of an enlargement of the components of the motorizing elements of the collimator of FIG. 10.

FIG. 10A shows an enlargement of the components of the motorizing elements that are detailed in reference to plate 5101. The other eleven plates' mechanisms are analogous.

Motor 5101A drives screw 5101B that moves nut 5101C. Nut 5101C is connected to plate 5101 thus enabling plate 5101 to move in the directions of arrow 5101D.

A "U" shaped coupler 5106 connects plates 5101 and 5102 wherein nut 5101E slides on the coupler side 5106A and nut 5102A slides on the coupler side 5106B.

The "U" shaped coupler dictates the motion limitations and ensures plates' coupling.

Therefore, as plate 5101 moves in the directions of arrow 5101D, plate 5102 moves with it in the same direction but in order to move in directions of arrow 5101F, plate 5112 moves and moves plate 5101 with it.

Hence, according to this configuration, a single plate cannot move without causing movement of another plate. Therefore, when the controller moves one motor, other motors may need to move.

The collimator 5100 is based on "passive coupling" meaning the "U" shaped couplers ensure coupling of the plates by forcing two adjacent edges of neighbor filters to maintain the distance between them by sliding along each other.

The motors slide freely on the rails 4505F according to the mentioned directions.

It would be appreciated that some of the plates may be movable by one motor and a coupler and some plates may be movable by two motors.

In that case an "active coupling" is needed in addition to the "passive coupling".

It would be appreciated that the specific motion mechanism described herein is provided to explain the invention and that the scope of the invention is not limited to this motion mechanism.

Figure 10B:
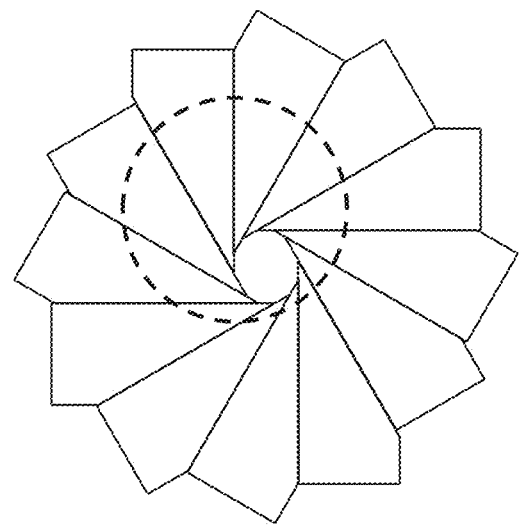
FIG. 10B is a top view of the collimator of FIG. 10 with the ROI at an off-center location.
Figure 10C:
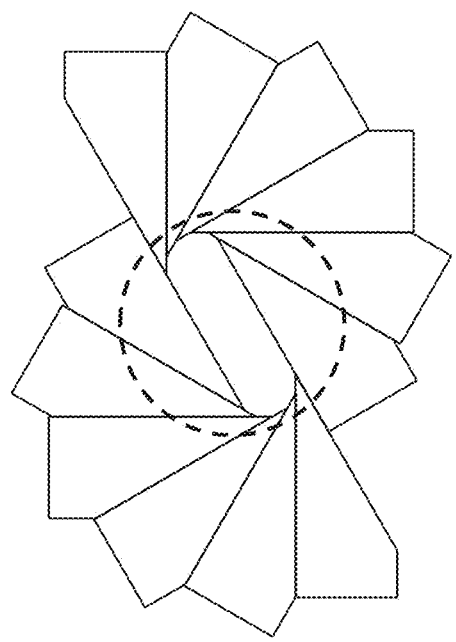
FIG. 10C is a top view of the collimator of FIG. 10 with the ROI at the center.

Reference is made now to FIGS. 10B and 10C

FIGS. 10B and 10C demonstrate an adjustment of plates 5101 through 5112 in order to create a specific ROI such as 3512B and 3512C.

The concept is expandable to any number of plates >2.

All the examples shown can also be placed on a rotatable and/or displaceable mechanism in x-y plane. Rotation is particularly useful for solutions with relatively small number of plates (such as 3, 4 and 5). 12 plates virtually eliminate the need for rotation.

A problem that may occur while using the "essentially non-overlapping filters" collimators aforementioned is a penetration of X-Ray radiation between the collimator plates.

Figure 12C:
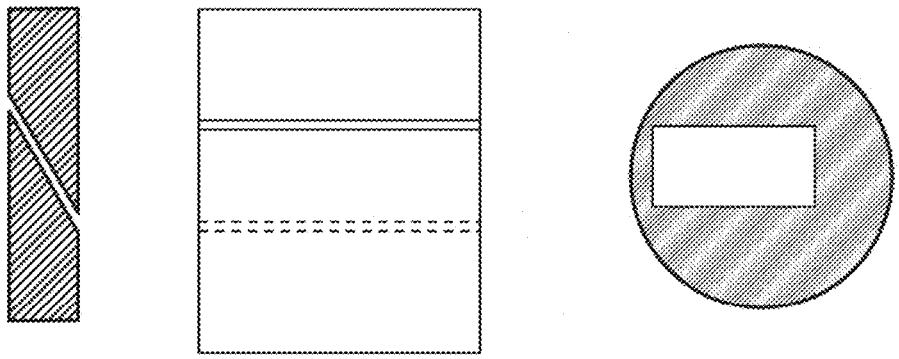
FIG. 12C demonstrates the use of "tapered edge" plates and the resulting image.
Figure 12B:
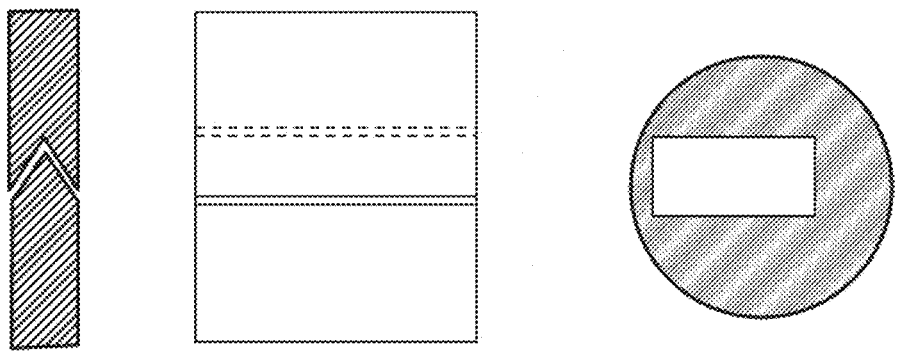
FIG. 12B demonstrates the use of "V shaped edge" plates and the resulting image.
Figure 12A:
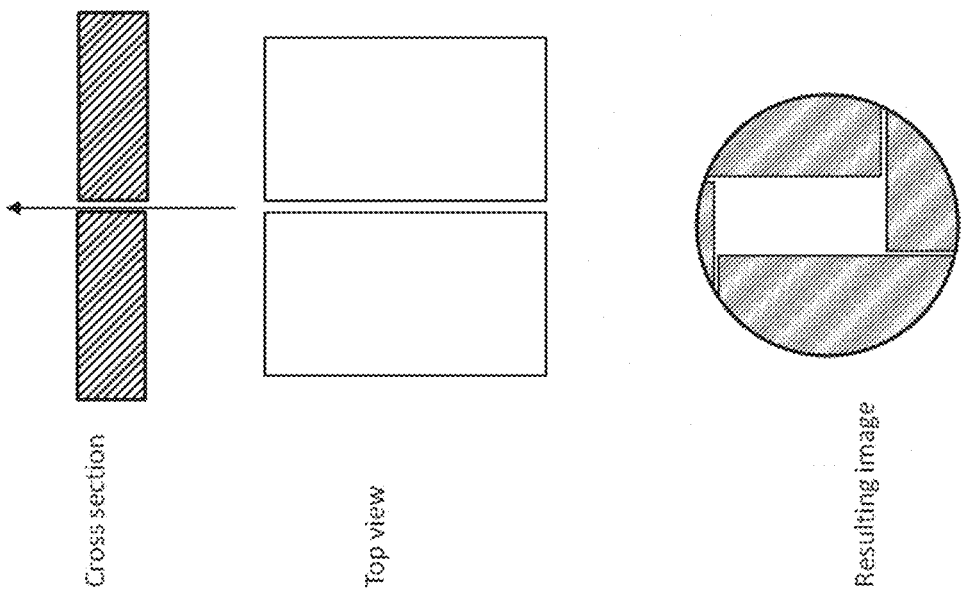
FIG. 12A demonstrates the use of "straight edge" plates and the resulting image with the x-ray radiation penetration.

FIG. 12A demonstrates the use of "straight edge" plates with radiation beam 5320 penetrating the filtering layer through a small gap between plates 5322 and 5324. This makes the line along which the two plates meet visible on the image as illustrated on resulting image 5326.

FIGS. 12B and 12C offer two solutions to the problem.

FIG. 12B demonstrates the use of "V shaped edge" plate with a negative or reversed V edge plate fitting each other so that ray 5320A cannot pass through the line of plates contact without being filtered. The resulting image 5326A without the effect of radiation un-intended penetration is shown.

FIG. 12C demonstrates the use of "tapered edge" plates and the resulting image.

Other edge shapes are considered, such as arcuate, concave, convex, contoured, or stepped, or any complementary, mating edge shape that effectively prevent line-of sight through the abutting plates along the primary direction of beam travel.

Figure 12D:
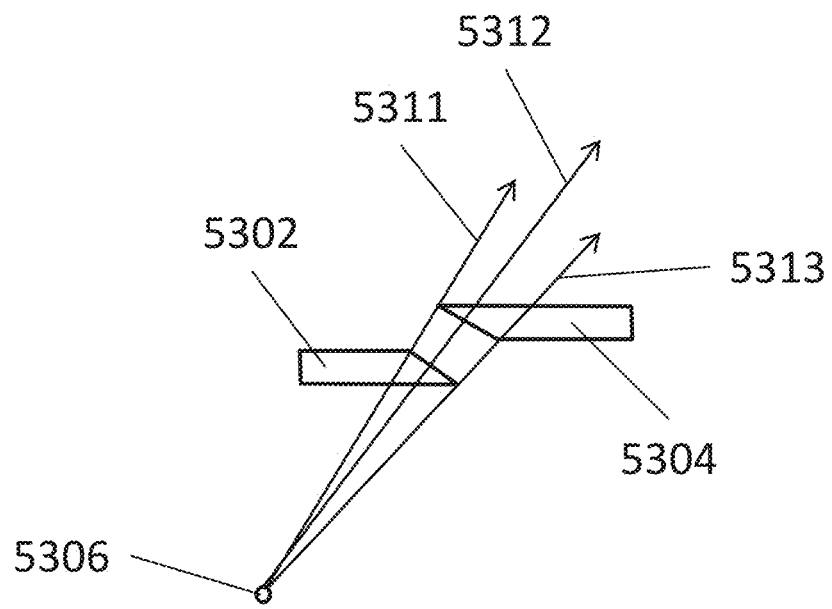
FIG. 12D demonstrates coupling when two filters are not at the same distance from the radiation source.
Figure 12E:
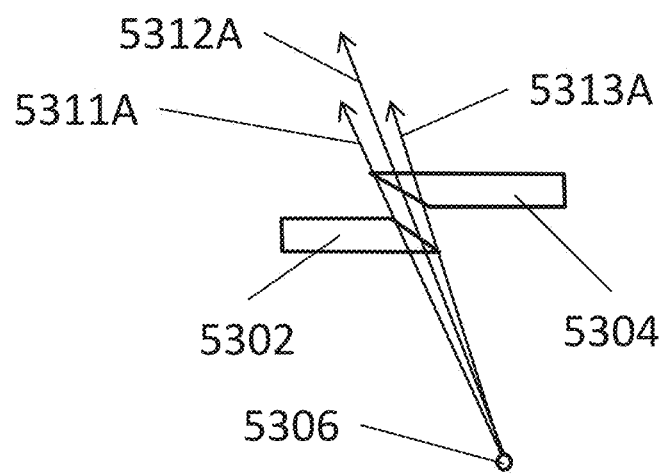
FIG. 12E also demonstrates coupling when two filters are not at the same distance from the radiation source.

FIGS. 12D and 12E provide another example for the coupling concept of the present invention. For this example, plates 5302 and 5304 of FIG. 12C are used. Unlike FIG. 12C where plates 5302 and 5304 are at the same plane, in FIGS. 12D and 12E plates 5302 and 5304 are not in the same plane. Plate 5304 is further away from radiation source 5306, in direction perpendicular to the planes of plates 5302 and 5304.

In FIG. 12D plates 5302 and 5304 are shown to the right of radiation source 5306. The horizontal distance between plates 5302 and 5304 is set so that radiation rays passing through each of the filters and in the zone including both filters experience essentially the same filtering. In this example ray 5311 is passing through plate 5302 only, ray 5313 is passing through plate 5304 only and ray 5312 passes through both plates 5302 and 5304. The horizontal distance between plates 5302 and 5304 is set so that all 3 rays experience essentially the same thickness of filtering.

In FIG. 12E plates 5302 and 5304 are shown to the left of radiation source 5306. Ray 5311A passes through plate 5302 only, ray 5313A passes through plate 5304 only and ray 5312A passes through both plates 5302 and 5304. The horizontal distance between plates 5302 and 5304 is set so that all 3 rays experience essentially the same thickness of filtering. Note that the horizontal distance between plates 5302 and 5304 in FIG. 12E is smaller than in FIG. 12D. This is because the change in the angle of incidence of the radiation rays. This demonstrates the concept of plates that are "coupled" in this invention. They are coupled in the sense of a constraint, requiring that the distance between the plates serves the purpose of essentially uniform filtering on a transition from one plate to another and not, for example, mechanical fixed distance (although mechanical fixed distance can serve as the desired coupling implementation for certain mechanical designs). It would be appreciated that the specific examples described here are provided to explain the invention and that the scope of the invention is not limited to these specific solutions.

It would be appreciated that although the above was described in reference to an image intensifier it is applicable to any detector, including a flat panel detector. The geometry of the detector, the zoom area and the ROI can be of a mixed nature and do not need to be of the same nature (i.e. circular or rectangular or another geometry).

It would be appreciated that throughout the description when, for example, the term aperture is used in the context of elongated aperture, the intention is to an elongated aperture.

It would be appreciated that "partially transparent" and "attenuating" are equivalent and the role of such a term is dependent on the amount of transparency or attenuation. In the above description the role of such terms is provided by the context of the description with specific value examples where needed. The structure examples provided in this disclosure can be implemented with different degrees of transparency to x-ray (or, equivalently, with different degrees of attenuation of x-ray), as preferred for specific implementations. As such they can be highly transitive to x-ray (low attenuation) or poorly transmissive to x-ray (high attenuation). High attenuation also refers to "x-ray blocking" terms since x-ray cannot be 100% blocked and "blocking" is used in the field of the invention to indicate high attenuation.

Figure 13:
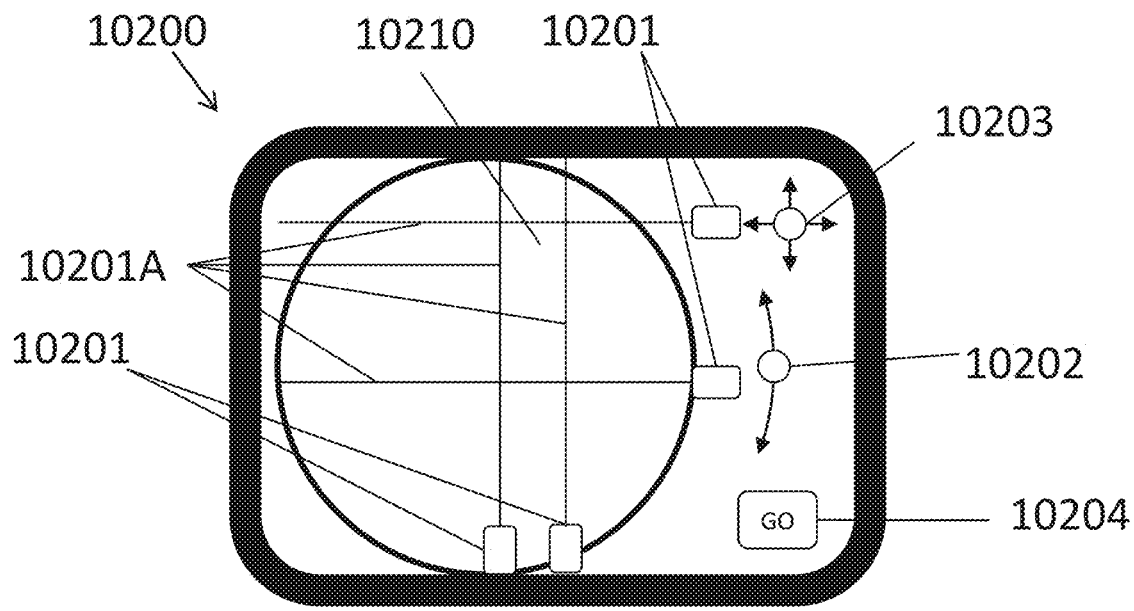
FIG. 13 shows an exemplary user interface which may be implemented as part of a control application.

FIG. 13 shows an exemplary user interface which may be implemented as part of a control application running on an electronic device having an interactive display, such as a tablet, a monitor or a smartphone. The application communicates with the controller 132 and displays the captured and corrected x-ray image.

The user uses four sliders 10201 to determine ROI 10210 size and location according to the area encodes by border lines 10201A, a rotation button 10202 to determine a rotation direction of the selected ROI (clockwise or anticlockwise) and initiates a rotation of the ROI accordingly until released, a displacement button 10203 for moving the selected ROI without changing its size and orientation and an optional "GO" button 10204 for implementing the actual motion of the collimator plates according to the indicated location, orientation and aperture size.

In the absence of a "GO" button, the plates' motion could starts each time the buttons are released or, in another example, after a predetermined time period with no changes in the interface setup.

Figure 13A:
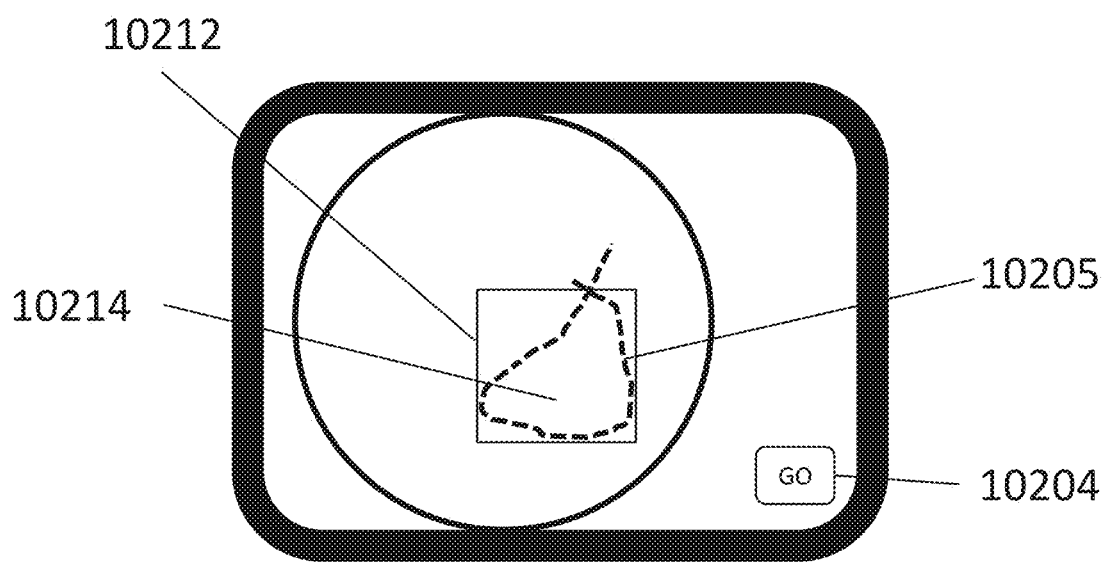
FIG. 13A is another example of a user interface and automatic ROI setup.

FIG. 13A is another example of a user interface. In order to select the wanted ROI the user marks any enclosing shape such as shape 10205 on the screen and the collimator plates are arranged in a position where they form an aperture that best encloses the shape. "GO" button 10204 is optional.

In the absence of a "GO" button, the plates' motion could starts each time the user stops drawing, or in another example, after the user removes his finger or drawing pen from a touch screen, or, in another example, after a predetermined time period with no changes in the interface setup.

Figure 13B:
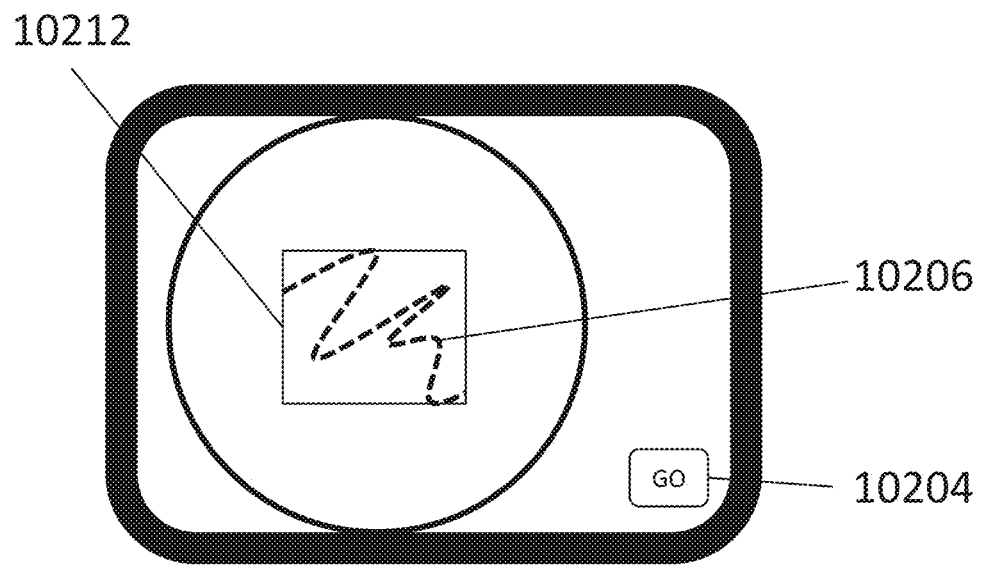
FIG. 13B is another example of possible shape drawing and automatic ROI setup using the user interface of FIG. 13A.

FIG. 13B is another example that is implemented on the same user interface as in FIG. 13A. In order to select the wanted ROI the user marks any shape such as line 10206 on the screen and the collimator plates are arranged in a position where they form an aperture that best encloses the shape.

"GO" button 10204 is optional.

In the absence of a "GO" button, the plates' motion could starts each time the user stops drawing, or in another example, after the user removes his finger or drawing pen from a touch screen, or, in another example, after a predetermined time period with no changes in the interface setup.

Figure 13C:
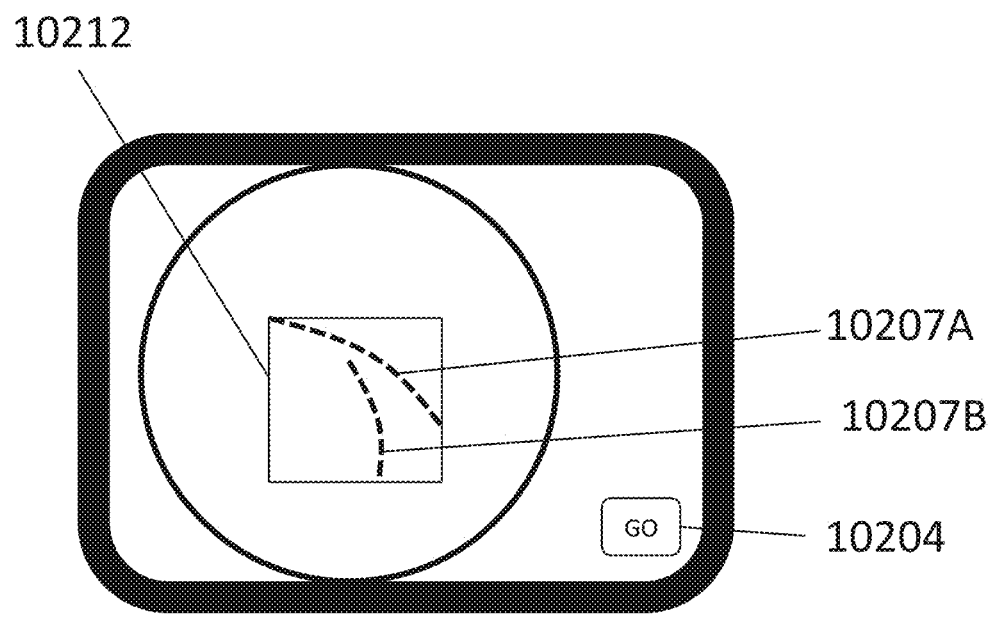
FIG. 13C is another example of possible shapes drawing and automatic ROI setup using the user interface of FIG. 13A.

FIG. 13C is another example that is implemented on the same user interface as in FIG. 13A. In order to select the wanted ROI the user marks more than one shape such as lines 10207A and 10207B on the screen and the collimator plates are arranged in a position where they form an aperture that best encloses the shapes.

"GO" button 10204 is optional.

In the absence of a "GO" button, the plates' motion could start each time the user stops drawing a shape segment. Alternatively, the plates' motion could start after a predetermined time period with no changes in the interface setup.

If time≤time period—shape is not completed (wait for the user to add new segment to the existing segments).

If time>time period—the drawing is finished and motion of ROI is engaged.

Figure 13D:
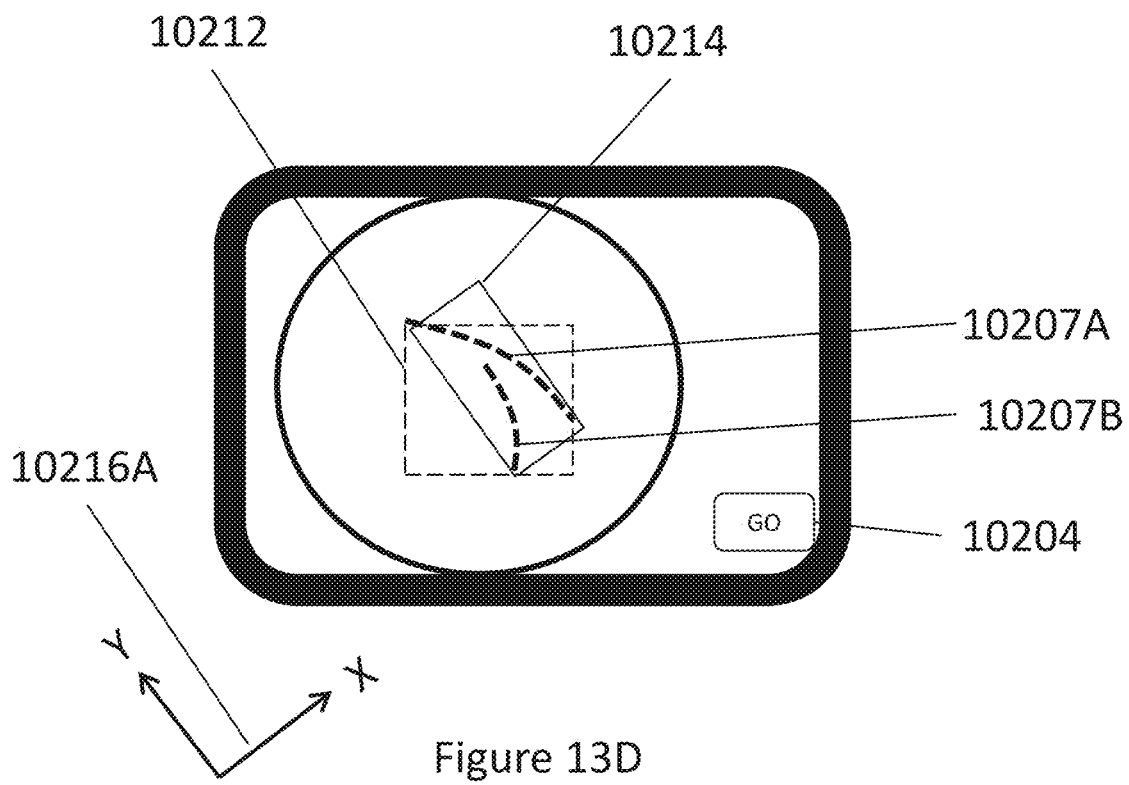
FIG. 13D is another example of possible shapes drawing and automatic ROI setup using the user interface of FIG. 13A.

FIG. 13D is another example that is implemented on the same user interface as in FIG. 13A. In order to select the wanted ROI the user marks more than one shape such as lines 10207A and 10207B on the screen and the collimator plates are arranged and rotated in a position where they form the smallest aperture that encloses the shapes. In this example the aperture shape is fixed.

Figure 13E:
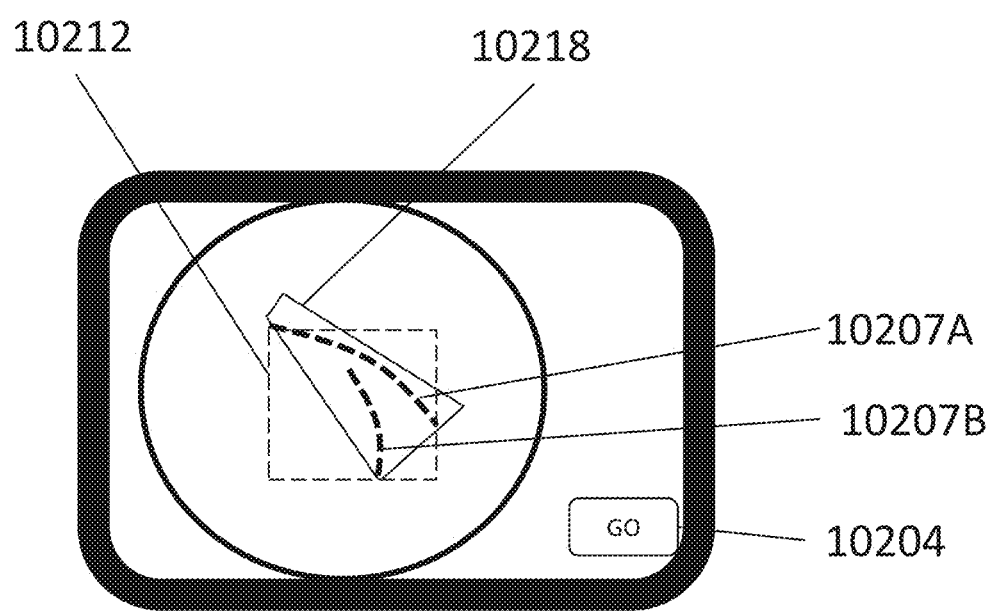
FIG. 13E is another example of possible shapes drawing and automatic ROI setup using the user interface of FIG. 13A.

FIG. 13E is another example that is implemented on the same user interface as in FIG. 13A. In order to select the wanted ROI the user marks more than one shape such as lines 10207A and 102078 on the screen and the collimator plates are arranged and rotated in a position where they form the smallest aperture that best encloses the shapes. In this example the aperture shape may be changed.

Figure 13F:
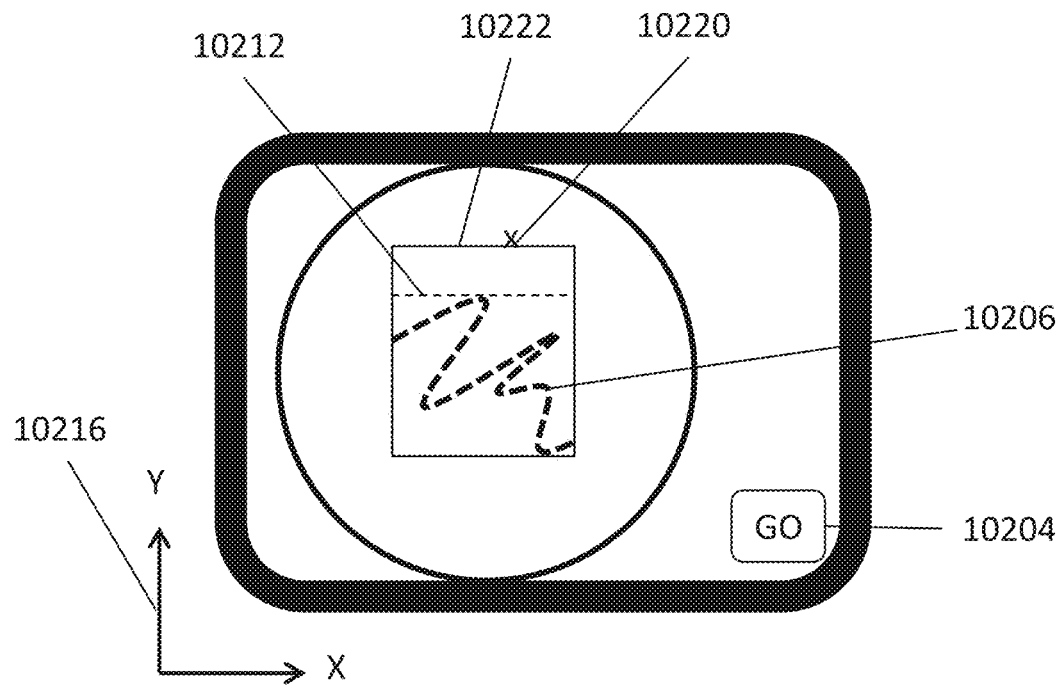
FIG. 13F is another example of possible shapes drawing and automatic ROI setup using the user interface of FIG. 13A.

FIG. 13F is another example that is implemented on the same user interface as in FIG. 13A. In order to select the wanted ROI the user marks any shape such as line 10206 on the screen and the collimator plates are arranged in a position where they form an aperture that encloses the shape.

When an additional point 10220 is added outside the ROI, the nearest edge to that point could move in parallel to its direction to that point so that calculated ROI 10212 changes to ROI 10222. In this example the aperture shape is fixed.

Figure 13G:
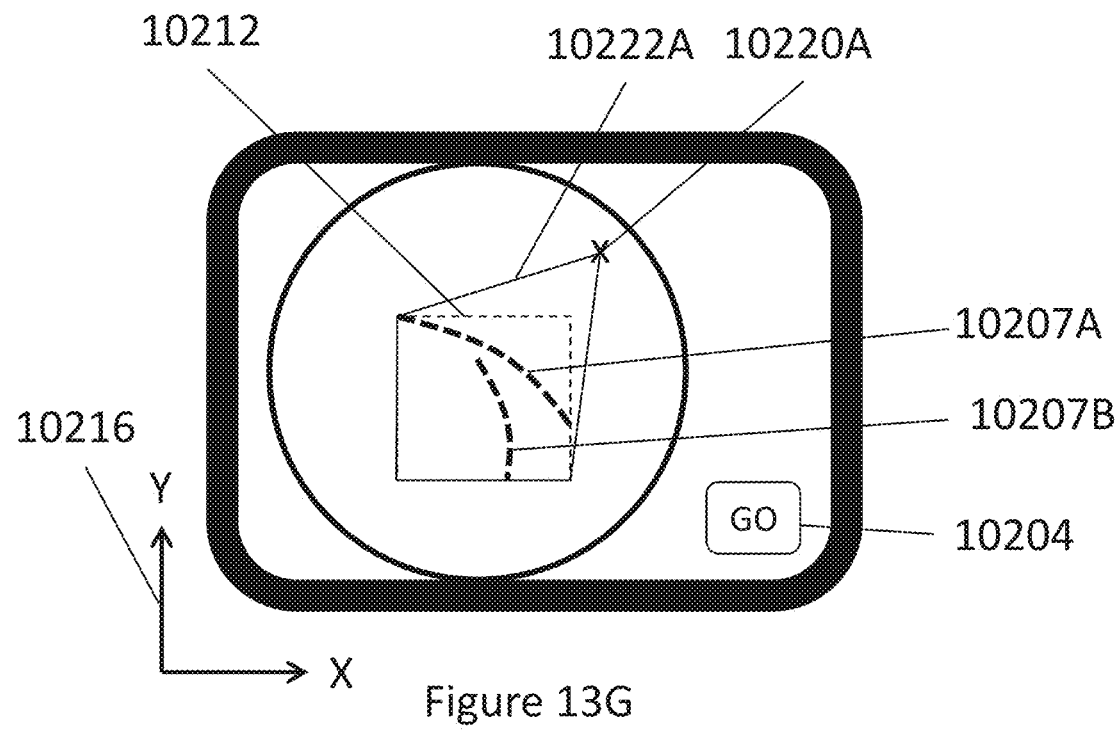
FIG. 13G is another example of possible shapes drawing and automatic ROI setup using the user interface of FIG. 13A.

FIG. 13G is another example, if the of the point 10220A to two nearest edges of the ROI is below some determined value, the corner where these two lines meet could move to the marked point so that calculated ROI 10212 changes to ROI 10222A. In this example the aperture shape may be changed.

Figure 13H:
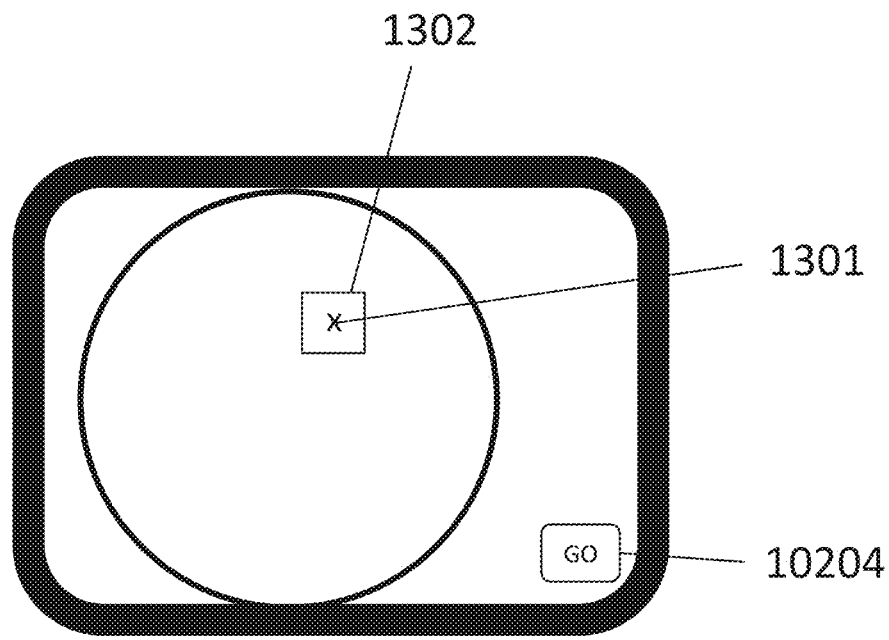
FIG. 13H is another example of possible shapes drawing and automatic ROI setup using the user interface of FIG. 13A.
Figure 13I:
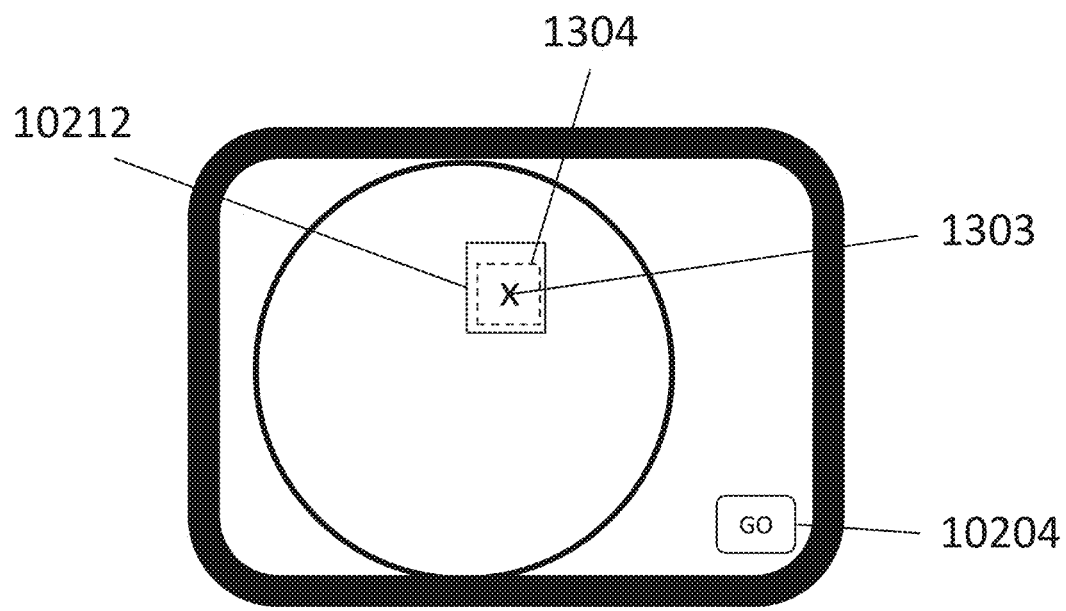
FIG. 13I is another example of possible shapes drawing and automatic ROI setup using the user interface of FIG. 13A.

According to embodiments of the present invention, in order to select the wanted ROI the user may use another method of ROI selection (on top of the described in conjunction with FIGS. 13A-G). One may tap on the screen and the collimator plates are arranged in such a position where they form an aperture accordingly, according to, but not limited to, one of the following options:

1. A predetermined circle around the tap is recognized as the location of the desired ROI (as if the user has drawn that circle by himself to set an ROI) and the collimator plates are arranged and/or rotated in a position where they form spatial radiation modulation according to that predetermined circle; or
2. A predetermined circle around the tap is recognized as the location of the desired ROI (as if the user has drawn that circle by himself to set an ROI) and the collimator plates are arranged and/or rotated in a position where they form the smallest possible aperture so that higher radiation intensity area best encloses that circle on the image; or
3. (FIG. 13H) A predetermined shape 1302 around the tap 1301 is recognized as the location of the desired ROI (as if the user has drawn that predetermined shape by himself to set an ROI) and the collimator plates are arranged and/or rotated in a position where they form higher radiation intensity area to fit, as possible, that predetermined shape on the image; or
4. (FIG. 13I) A predetermined shape 1304 around the tap 1303 is recognized as the location of the desired ROI (as if the user has drawn that predetermined shape by himself to set an ROI) and the collimator plates are arranged and/or rotated in a position where they form the smallest possible aperture so that higher radiation intensity area 10212 best encloses that shape on the image; or
5. Using image processing, the system of the present invention may automatically recognize an organ that includes the tapping location and provides a shape that best encloses that organ, that shape is recognized as the desired ROI and the collimator plates are arranged and/or rotated in a position where they form the smallest possible aperture so that higher radiation intensity area best encloses that desired ROI.

Example for automatically recognize an organ is provided in "Automatic Classification of Body Parts X-ray Images" by Moshe Aboud[1], Assaf B. Spanier[1,2], and Leo. Joskowicz[2] ([1] Department of Software Engineering, Jerusalem College of Engineering, [2] The Selim and Rachel Benin School of Engineering, The Hebrew Univ., Jerusalem, Israel)

"GO" button 10204 is optional.

In the absence of a "GO" button, the plates' motion could starts each time the user removes his finger or drawing pen from a touch screen, or, in another example, after a predetermined time period with no changes in the interface setup.

Figure 13J:
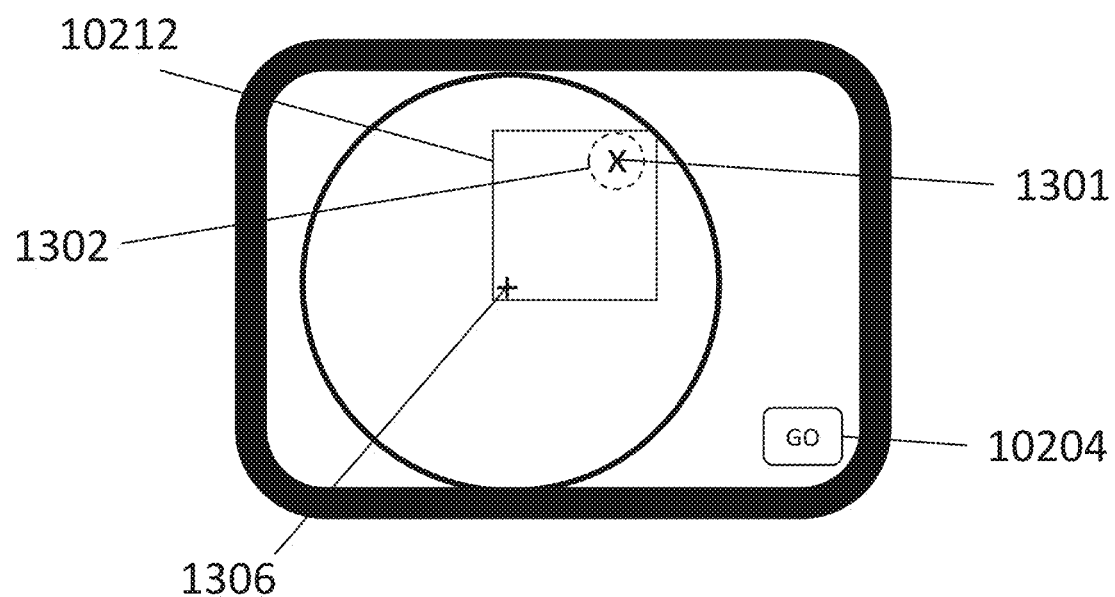
FIG. 13K is a block diagram of an exemplary automatic following of an organ process.

According to embodiments of the present invention, as shown in FIG. 13J, the final ROI 10212 may need to include at least one predetermined location 1306 in the Field of View (FOV). In such cases, the collimator plates are arranged and/or rotated in a position where they form the smallest possible aperture so that higher radiation intensity area best encloses the selected ROI 1302 including the at least one predetermined location 1306.

It will be appreciated that the user interface and the user interface capabilities described in the present invention are not tied or limited to the collimators described in the present invention and the present invention is not limited to use only those collimators.

Alternatively or additionally, the user interface of the present invention may be used with any collimator capable of moving an aperture, create an aperture, or form a shape in a desired location.

According to embodiments of the present invention, when the ROI is selected, the user interface may enable the user to:

1. Lock the selected ROI (maintain the shape and size unchanged) and drag it to a different location within the FOV on the screen; or
2. Lock the selected ROI and tap on a different location on the screen to automatically move the selected ROI to the new tapping location.
3. Lock the selected ROI to automatically follow an organ existing in the selected ROI.

Figure 13K:
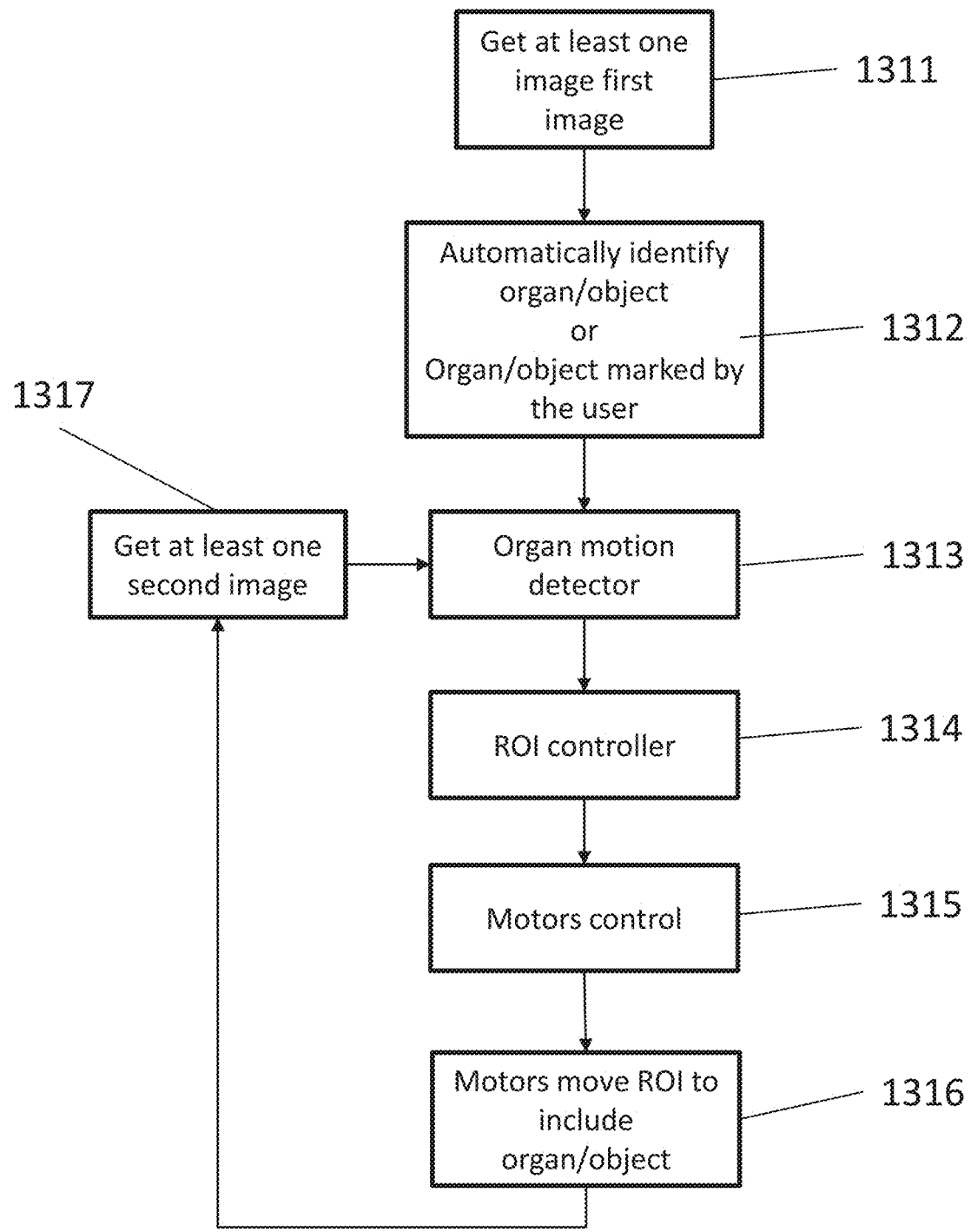

A block diagram of such automatic following of an organ is shown in FIG. 13K.

At least one first image is received by the imaging system (1311). An organ or object is identified automatically or manually by the user (1312). An organ detector or object detector keeps tracking the motion of the identified organ/object (1313) and provides the ROI controller (1314) with information of the location of the organ/object in the image. The ROI controller send the required ROI position to the motors control (1315) that sends motion instructions to the motors, that in turn, move the ROI to include the organ/object (1316). At least one second image is received (1317) and the process repeats.

It would be appreciated that the organ/object tracking does not have to be synchronized in a loop with the at least one second images but it can run, independently on any, typically latest image received, each time tracking calculation cycle starts.

According to embodiments of the present invention, when the ROI is selected, the system may enable the user to lock the selected ROI and move it to a different location on the screen according to measurements received from a tracking device, such as, for example, an eye tracker, a hand gesture tracking device, by a voice command, etc.

According to embodiments of the present invention, the system may enable to automatically move or change the size of a selected ROI based on the movement of the patient and/or the table, on which the patient is lying, and/or the movement of a medical device inserted into the patient's body.

For example, if the selected ROI is recognized as including a specific organ, and the user selected locking method #3, the ROI may be moved automatically, following that organ, when the patient and/or the table, on which the patient is lying, moves. When this locking method is enabled, the system can use image processing with registration and temporal movement detection to determine the changed location of the center of the captured organ and use this path as if the user virtually dragged the locked ROI by himself.

Moreover, the system may change the ROI shape according to the movement or zoom changes in order to make sure that the organ is covered by, or included in, the ROI.

ROI 10212 borders could be automatically calculated and set in a variety of methods including:

1. Closing on the enclosed area 10214 so that two of the ROI edges are horizontal and located at maximum Y and minimum Y of area 10214 (in reference to coordinate system 10216 in FIG. 13A-13C) at the top and at the bottom of area 10214 and two of the ROI edges are vertical and located at maximum X and minimum X of the border of area 10214 at the left and at right of area 10214.
2. Same method as (1) but including the marking lines that are outside of enclosed area 10214.
3. The method of either (1) or (2) and also rotating the rectangular ROI to an angle that encloses a smaller area. This is demonstrated in FIG. 13D where ROI 10214 is rotated and each of the edges of the ROI is set, relative to coordinate system 10216A that is now rotated, for reference, at the same angle ROI 10214 is rotated. Also here the edges parallel to the Y direction enclose on the combined shape of 10207A and 102078 in a position of maximum X and minimum X of the combined shape and the edges parallel to the X axis direction enclose on the combined shape of 10207A and 102078 in a position of maximum Y and minimum Y of the combined shape so that ROI 10214 has smaller area than ROI 10212 of FIG. 13C for the same shape. Different criteria may be involved in determining the ROI shape, size and angle. For example:
    1. Minimal area could be one criterion for setting the ROI angle and borders as described above.
    2. Aspect ratio could be another criterion to set the ROI angle and borders as described above.
    3. Minimal ROI dimension could also be used as a criterion for calculating the desired ROI.
    4. An area or dimension factor criterion could also be used to calculate the desired ROI. For example, the calculated area to enclose with the ROI can be a certain percentage of the minimal area. In another example at least one calculated dimensions of the ROI can be changed by a certain percentage. Such changes could also be done using an additive value (positive or negative) instead or with a percentage value.
    5. A criterion using a percentage of the entire field of view could be used to calculate the desired ROI. For example, such a criterion could require that the ROI area would be 15% of the area of the field of view. In another example the area of the ROI could include a certain amount of pixels of the image.
    6. A constraint input by the user could be used also. For example, after setting ROI according to any of the above methods, the user could mark a point outside the ROI (10220 in FIG. 13F) and the nearest edge to that point could move in parallel to its direction to that point so that calculated ROI 10212 changes to ROI 10222 (FIG. 13F). In another example, if the difference of the point distances to two nearest edges of the ROI is below some determined value (10220A in FIG. 13G), the corner where these two lines meet could move to the marked point so that calculated ROI 10212 changes to ROI 10222A (FIG. 13G).
    7. The constraints of section (f) above could also be introduced by any of touching at least one of the line images of the ROI and dragging it perpendicularly to its direction and touching at least one of the corner images of the ROI and dragging it in any direction. Such touching and dragging could be done using any input device such as a finger on a touch screen or a mouse of a computer.
    8. A combination of any of the above criteria could be used to calculate the desired ROI. For example, An ROI with a minimal area could be calculated, then the aspect ratio criterion could be employed to increase the smaller size of the ROI until the aspect ratio limitation is satisfied. Then, if the resulting area is still below any area criterion, the ROI could be increased (maintaining the aspect ratio, angle and center) until the area criterion is satisfied. Following that the user can mark a point near an edge, inside the ROI, and the edge moves to that point (overriding the aspect ratio and area criteria.
4. The method of either (1), (2) or (3) and also changing from rectangle to any 4-edges shape enclosing the minimal area, as per the example of ROI 10218 of FIG. 13E.
5. Closing on the drawn area 10206 so that two of the ROI edges are horizontal and tangent to the border of 10206 area at the top and at the bottom of area 10206 and two of the ROI edges are vertical and tangent to the border of 10206 area at the left and at right of area 10206.
6. Closing on the drawn area comprising more than one drawing 10207A and 102078 so that two of the ROI edges are horizontal and tangent to the border of 10207A and 10207B area at the top and at the bottom of drawings 10207A and 10207B and two of the ROI edges are vertical and tangent to the border of 10207A and 10207B area at the left and at right of drawings 10207A and 10207B.
7. The method of either (5) or (6) and also rotating the rectangular ROI to an angle that encloses the minimal area.
8. The method of either (5), (6) or (7) and also changing from rectangle to any 4-edge shape so as to enclose the minimal area.

In the example of FIGS. 13A-13D and 13F an enclosing rectangle is shown, which corresponds to a rectangular aperture such as shown in conjunction with the collimator of FIGS. 4-7, as will be explained below. In the example of FIGS. 13E and 13G an enclosing quadrilateral is shown, which corresponds to a quadrilateral aperture such as shown in conjunction with an embodiment of the collimator of FIG. 8-10

The user interface can be operated using touch screen or any other input device such as a computer mouse.

Both user interface options (FIGS. 13 and 13A) may be active at the same time and the user may select the most appropriate one.

Figure 14:
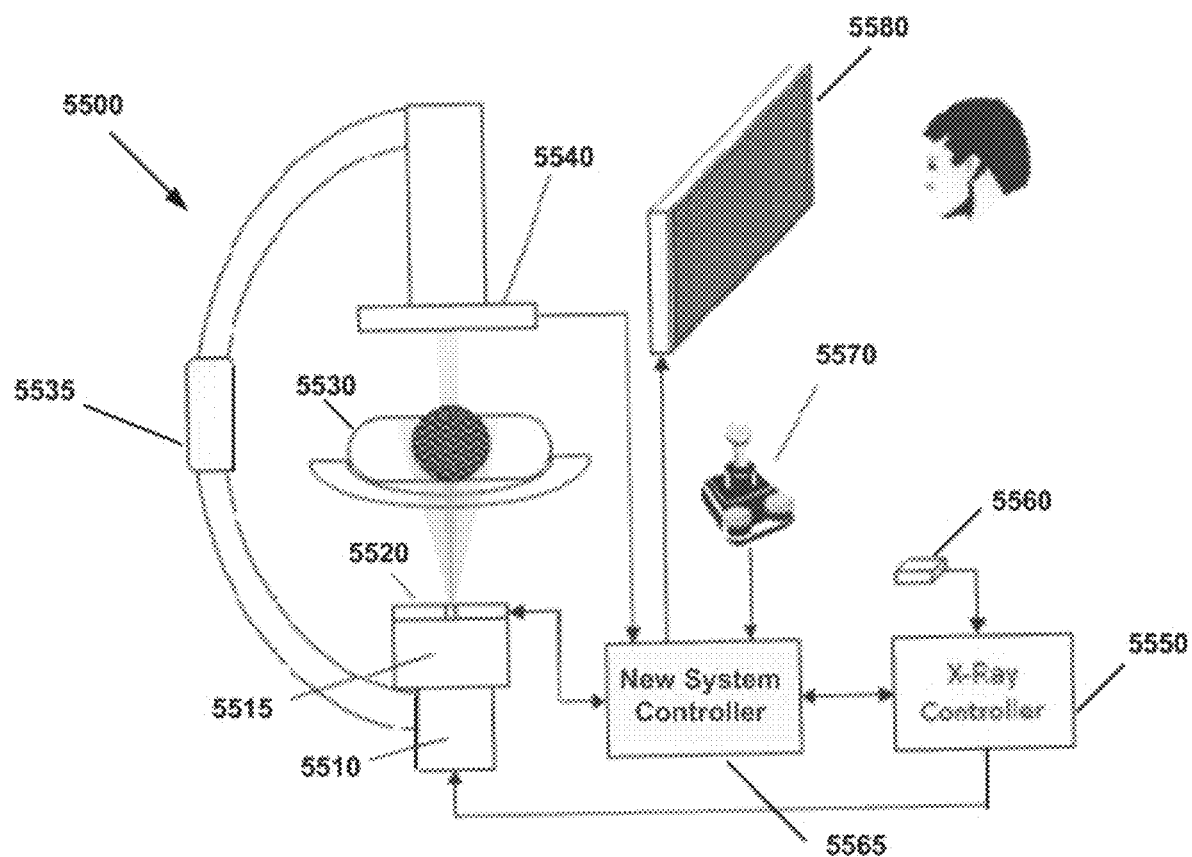
FIG. 14 depicts schematically an existing system with the additional collimator that is mechanically connected.

According to another embodiment of the present invention, any collimator described herein and any other existing or future collimator may be added to an existing multiple frame imaging system as a retrofit, mechanically connected with the C-Arm and mounted between the existing collimator and the patient. FIG. 14 depicts schematically such a system 5500 comprising an X-ray source 5510, an original collimator 5515, an additional collimator 5520 according to the present invention, a patient 5530, a C-Arm 5535, a detector 5540, an X-Ray controller 5550, an X-Ray operating pedal 5560, an exemplary user interface device joy stick 5570 and a display 5580.

The new system controller 5565 is connected with the detector 5540 to receiver therefrom detected images, image process them as described above in conjunction with the various embodiments, displays the corrected image on the display 5580 and controls the collimator 5520 according to inputs from the joy stick (or tablet or any other user interface device capable of indicating a required ROI relative to a displayed image).

Display 5580 may display the image obtained through both collimators without image correction, the image obtained through both collimators with image correction and the image obtained through the original collimator only.

According to embodiments of the invention, the user interface device may provide selection between the two collimators to determine which collimator is currently addressed. Furthermore, when the original collimator is selected for operation/activation the newly inserted collimator would translate in parallel with the X-Ray detector plane and move out of the X Ray beam pathway so that not to effect the beam.

The additional collimator 5520 according to the present invention may be connected to the original collimator 5515, or to the radiation tube or to the c-arm by mechanical or other connection means as will be explained bellow in FIGS. 16-19A.

Figure 15:
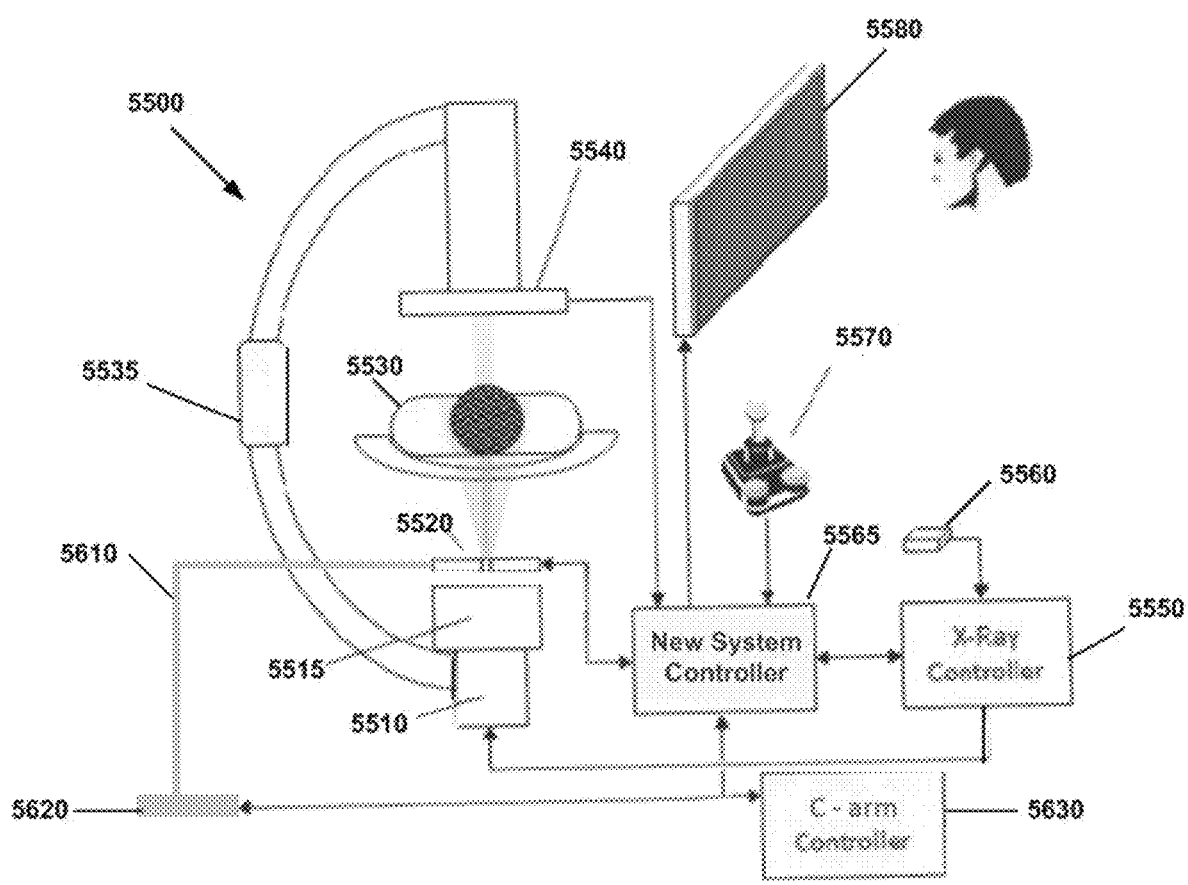
FIG. 15 depicts schematically an existing system with the additional collimator that is driven by a robotic arm.

FIG. 15 is another embodiment of the system of FIG. 14 according to the present invention. The additional collimator 5520 may also be driven by a robotic arm 5610 such as for example in coordination with the original collimator 5515, such that the new collimator moves and functions while being mechanically supported on its own base without necessarily being mechanically attached to any moving section of the original X-ray system. Such robotic arm will use electronic sensors and controllers to provide accurate tracking motion as needed to perform the collimation function of the new collimator which is attached to the end effector/gripper/hand of the robot.

The "robotic arm" may be controlled by use of:
1. Multiple sensors such as optical, magnetic or others that ensure tracking and coordination with the original collimator and X Ray system.
2. The robot controller 5620 communicates directly with (or in some cases may be embedded within) the C-ARM motion controller 5630.

Figure 16:
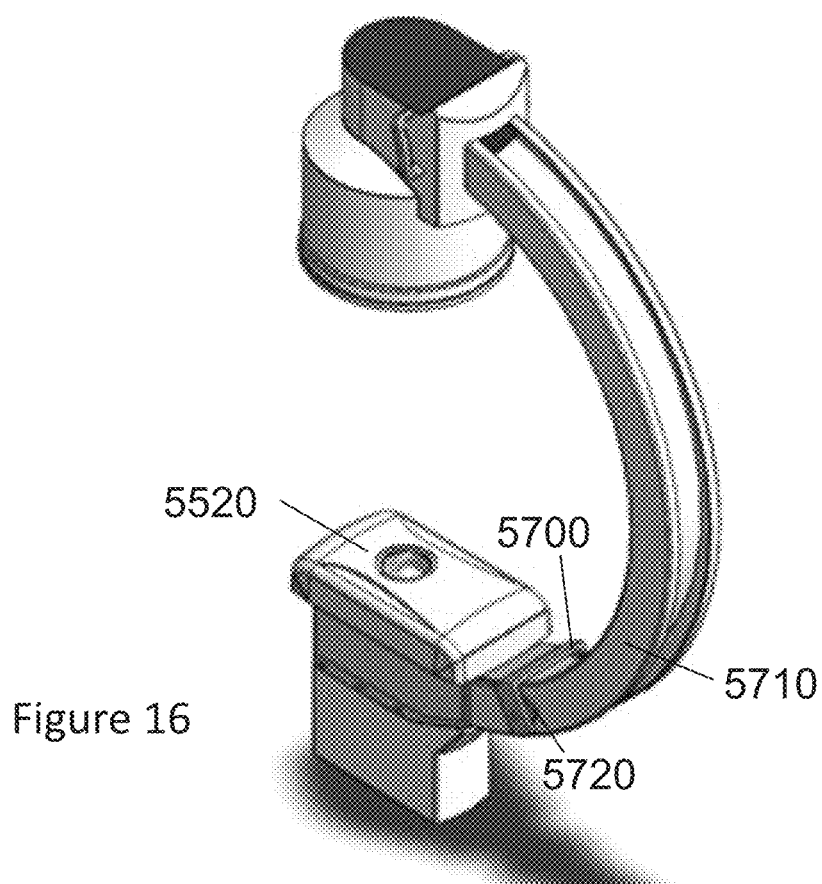
FIG. 16 is an example of a mechanical connection.

As mentioned above the additional collimator 5520 according to the present invention may be connected to the original collimator 5515, or to the radiation tube or to the c-arm by mechanical or other connection means. FIG. 16 is an example of such mechanical connection. Collimator 5520 is steadily mounted via adapter 5700 to the c-arm 5710 by screws, glue, welding, etc. 5720 that ensure coupling of the adapter and the collimator.

Figure 16A:
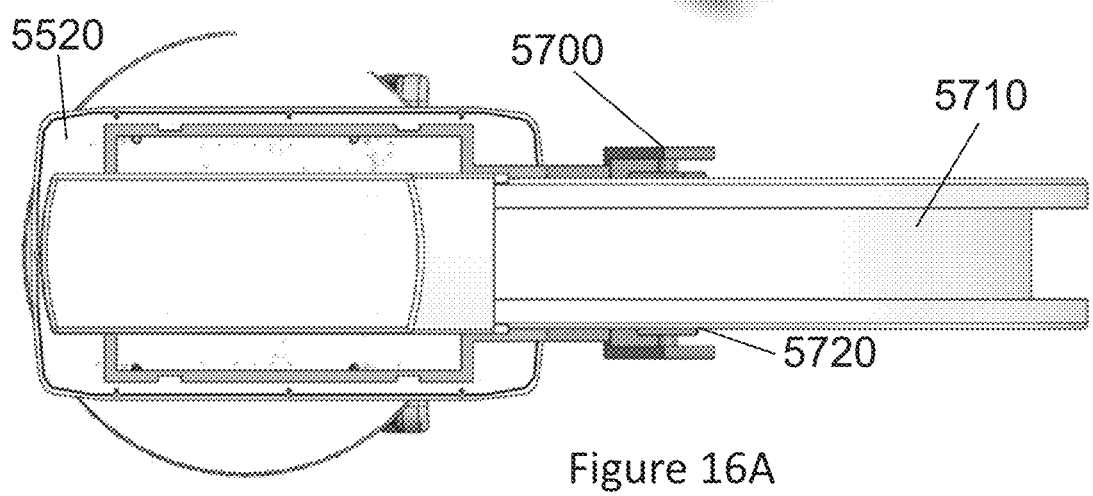
FIG. 16A is a top view of the system of FIG. 16.

FIG. 16A is a top view of the system of FIG. 16.

Figure 17:
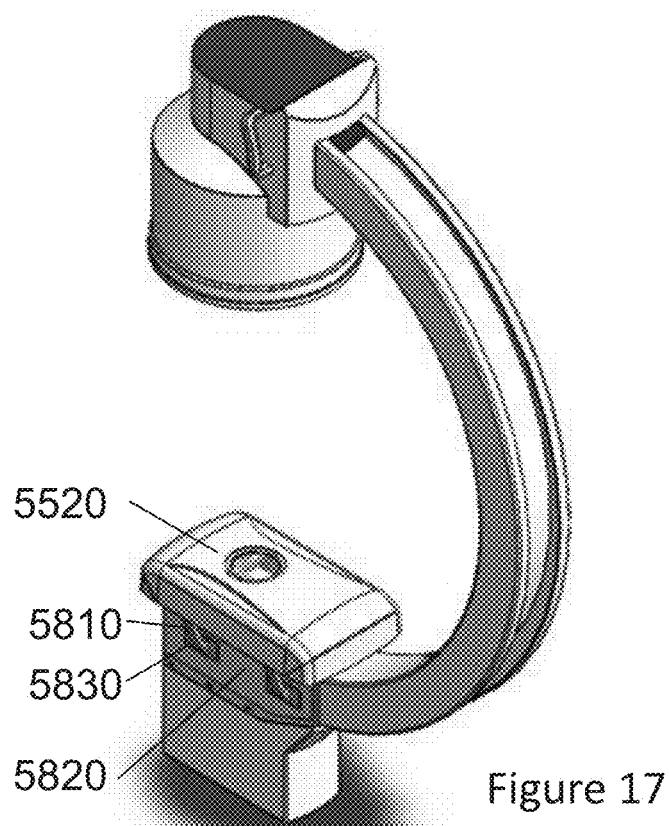
FIG. 17 is another example of a mechanical connection.

FIG. 17 is another example of a mechanical connection. Collimator 5520 is steadily mounted via adapter 5810 to the original collimator cover or to the radiation tube cover 5820 by screws, glue, welding, etc. 5830 that ensure coupling of the collimator.

Figure 17B:
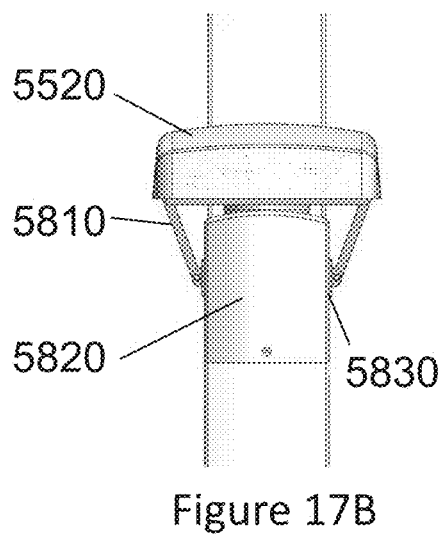
FIG. 17B is another side view of the system of FIG. 17.
Figure 17A:
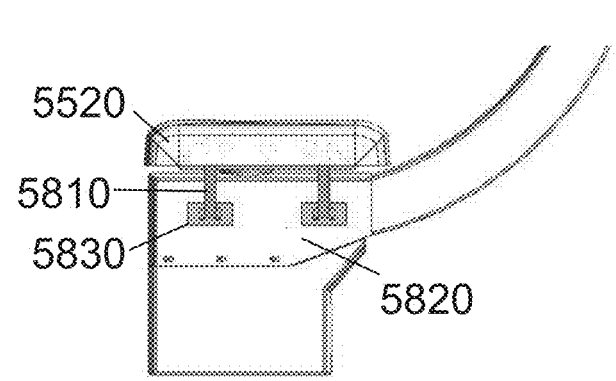
FIG. 17A is a side view of the system of FIG. 17.

FIGS. 17A and 17B are side views of the system of FIG. 17.

Figure 18:
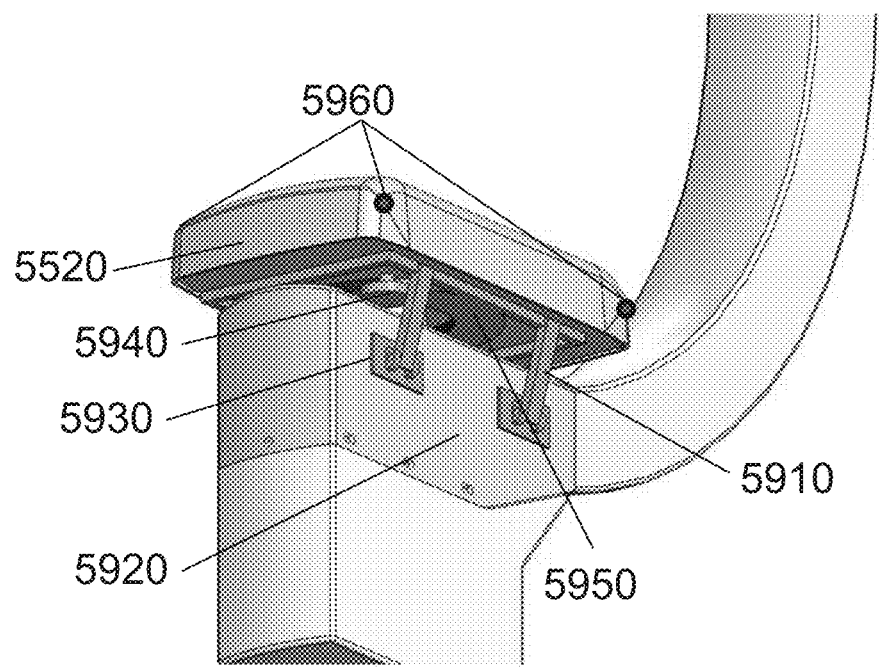
FIG. 18 is another example of a mechanical connection.

FIG. 18 is another example of a mechanical connection. Collimator 5520 is steadily mounted via adapter 5910 to the original collimator cover or to the radiation tube cover 5920 by screws, glue, welding, etc. 5930 that ensure coupling of the collimator. The adapter additionally comprises a rotation unit comprising a motor 5940 and a slew bearing 5950. After the collimator 5520 is mounted, it can be rotated using this rotation unit. Sensors 5960 may be placed in each corner of the collimator 5520 (two not shown) in order to prevent collision, for example, with the c-arm.

Figure 18A:
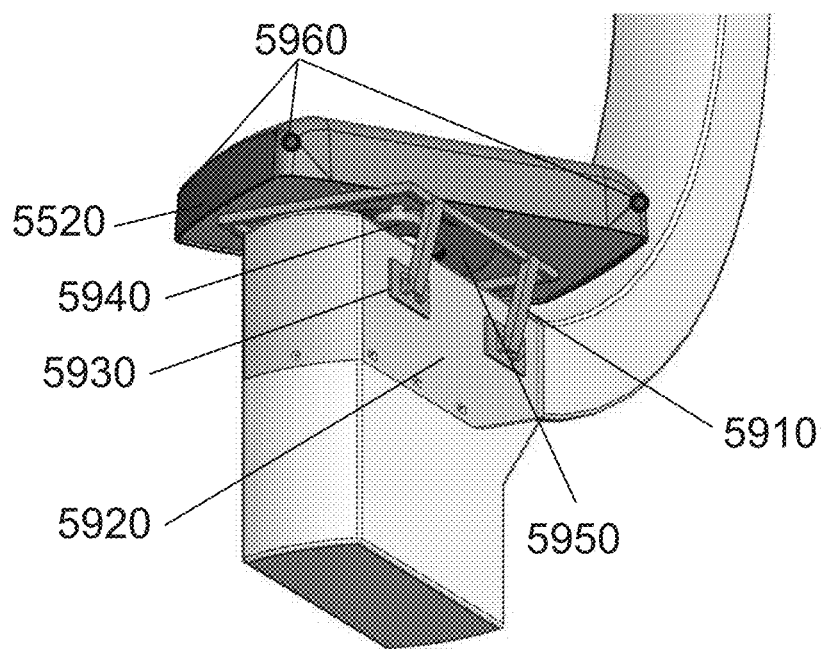
FIG. 18A is an example of a rotated collimator of the system of FIG. 17.

FIG. 18A is an example of the system of FIG. 18 when collimator 5520 is rotated.

Figure 19:
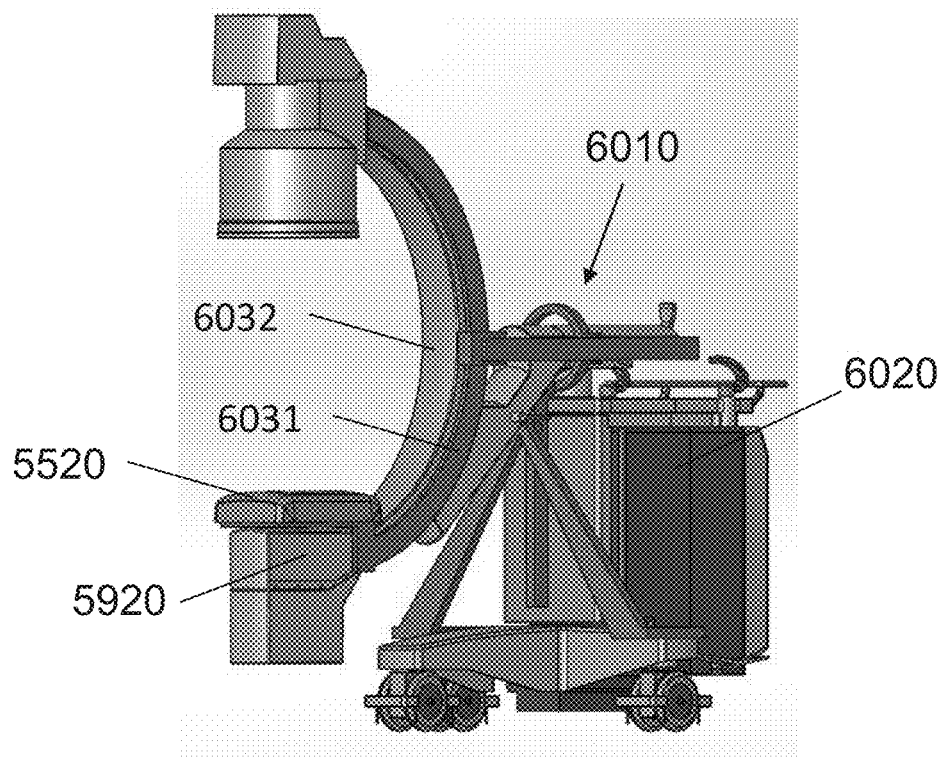
FIG. 19 is another example of a mechanical connection.

FIG. 19 is another example of a mechanical connection. Collimator 5520 is steadily mounted via adapter 6010 to the c-arm cabinet 6020. The adapter may be connected anywhere on the c-arm cabinet or rest on wheels on the floor, typically next to cabinet 6020 or the cabinet wheels (not shown).

If it is coupled to the cabinet, it travels with it. The motions of adaptor 6010 components are the same as the c-arm analog components in directions of dual head arrows 6030-6060 (shown in FIG. 19A).

Figure 19A:
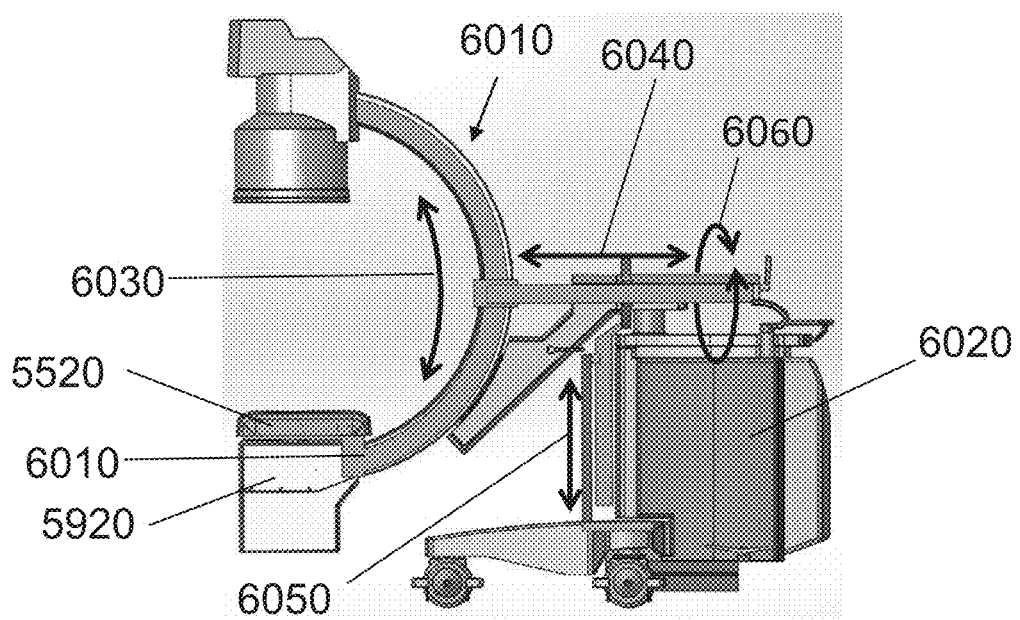
FIG. 19A is a side view of the system of FIG. 19.

FIG. 19A is a side view of the system of FIG. 19 with direction dual head arrows 6030-6050.

For example, component 6031 adaptor 6010 is coupled to c-arm component 6032 and whenever c-arm part 6032 moves, adaptor component 6031 follows it and maintains its' position relative to c-arm component 6032. In the same way, each component of the c-arm "arm" that holds collimator 5920 has the analog component in adaptor 6010 that is coupled to it, and moves with it maintaining the relative position.

Figure 20A:
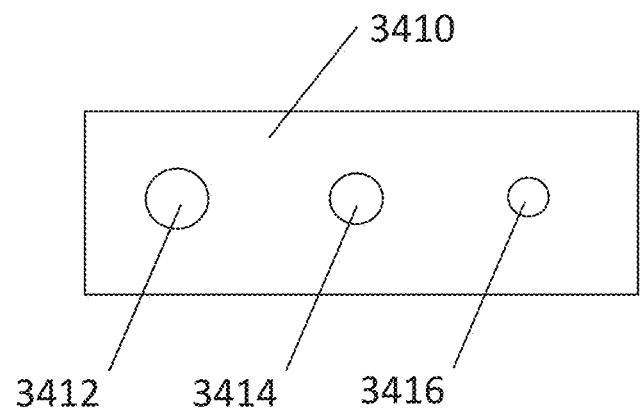
FIG. 20A shows an exemplary collimator having three holes for ROI of three different sizes.

According to embodiments of the present invention, the system may use a multiple holes collimator. FIG. 20A shows an exemplary collimator 3410 having three holes for ROI of three different sizes. For example, each ROI hole diameter is designed to project ⅓ of the exposed area diameter. For example, if image intensifier input area 112 diameter is 12" and it has 2 zoom options 9" and 6" then hole 3414 will be 9/12 of hole 3412 and hole 3416 will be 6/12 of hole 3412 in diameter. For each zoom of image intensifier 114 the corresponding area of collimator 3410 is used so that the ROI is maintained ⅓ in diameter of image 120 diameter.

Figure 20B:
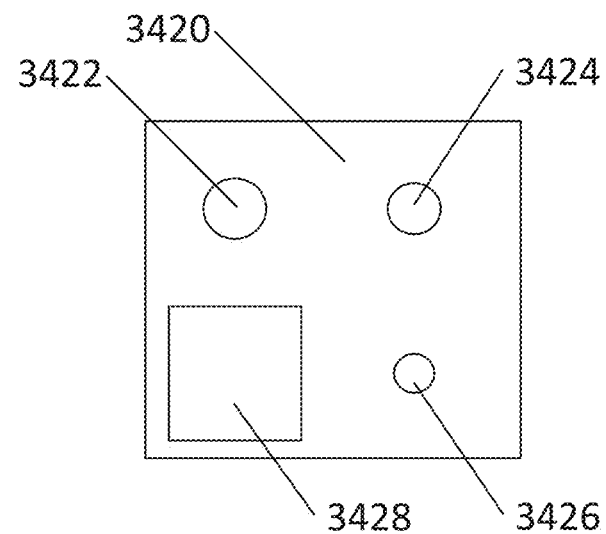
FIG. 20B shows another exemplary collimator having four holes for ROI of three four sizes.

FIG. 20B shows another exemplary collimator 3420 enabling adjustment of ROI hole to the zoom options of the image intensifier 114 in a similar manner to collimator 3410 but with a different geometry and holes 3422, 3424, 3426 and 3428.

Rectangular hole 3428 (that can also be a relatively large circular hole) provides a collimator area which does not limit the x-ray and enables conventional usage of such system.

It would be appreciated that collimators with a plurality of holes such as those of FIGS. 20A and 20B can also be moved perpendicularly to the collimator plane to provide variable size ROI onto input area 112 and/or also may be rotated. By combining more than one-hole size and movement perpendicularly to the collimator area, more ROI sizes can be provided with reduced vertical movement range comparing to one hole.

As the variety of holes dimensions increases, a smaller motion range is required perpendicularly to the collimator plane to cover more ROI sizes.

It would also be appreciated that the examples of FIGS. 20A and 20B can be combined with any of the edges as shown in FIGS. 12A to 12E.

Reference is made now to FIG. 21A providing another example of collimator 3500 of the present invention. Coordinate system 126 is present in FIG. 21A to provide orientation in reference to FIG. 1B.

X-ray focal point 306 is shown and a cone-shaped x-ray beam 107 is projected upwards towards input area 112 (not shown—see, e.g., FIG. 1B).

Plates 3501, 3502, 3503 and 3504 are partially transparent to x-ray. In this example we shall assume that each such plate transmits 30% of beam 107 but it would be appreciated that other transmission levels are available. Plates 3501, 3502, 3503 and 3504 can be made from any suitable material, considering the desired effect of the spectral distribution of the transmitted x-ray beam. For example, copper plates can be used.

Dashed circle 107A represents x-ray cone 107 cross section at generally the plane of collimator 3500. Except for a rectangular shaped x-ray beam, 3510, the rest of the beam (107B) intensity is reduced due to plates 3501, 3502, 3503 and 3504. Where there is only one layer of plates the x-ray beam is reduced to 30% of its original intensity. In areas where two plates overlap the x-ray beam is reduced to 9% of its original intensity (30%×30%), With this example ROI 3510 is now rectangular. Motors can move plates 3501, 3502, 3503 and 3504 as explained in FIG. 21B.

It would be appreciated that due to x-ray spectral changes depending on thickness of filtering material, the result of 2 layers, each allowing 30% of the incident x-ray to pass, is typically not 9% but depends on the original x-ray spectrum and the material of the filter. Yet, in the disclosure of this invention we shall assume such relations (30%×30%=9%) to simplify the description of the invention. Actual absorbance of one layer Vs 2 layers can be designed per the needs of any specific application and it will be ignored in this disclosure.

In FIG. 21B the components of the motorizing elements are detailed in reference to plate 3501. The other 3 plate's mechanisms are analogue.

Motor 3501A drives screw 3501C that moves nut 3501B. Nut 3501B is connected to plate 3501 therefore enables plate 3501 to move in directions of arrow 3501D. Therefore, each plate can move independently of the other plates as indicated by dual-head arrow for each plate. Rails that may be used to support the plates and enable motion are not shown in this figure. It would be appreciated that the specific motion mechanism described here is provided to explain the invention and that the scope of the invention is not limited to this motion mechanism.

In the example of FIG. 21B hole 3512 is at the center of beam 107 (as shown by the beam cross section 107A) and it has a certain size.

In the example of FIG. 21C plates 3503 and 3504 were moved to the right without changing the distance between these plates. Plates 3501 and 3502 were moved upwards without changing the distance between these plates. As a result hole 3512 moved towards the top-right edge of x-ray beam cross-section 107A but without changing its' dimensions.

Figure 21D:
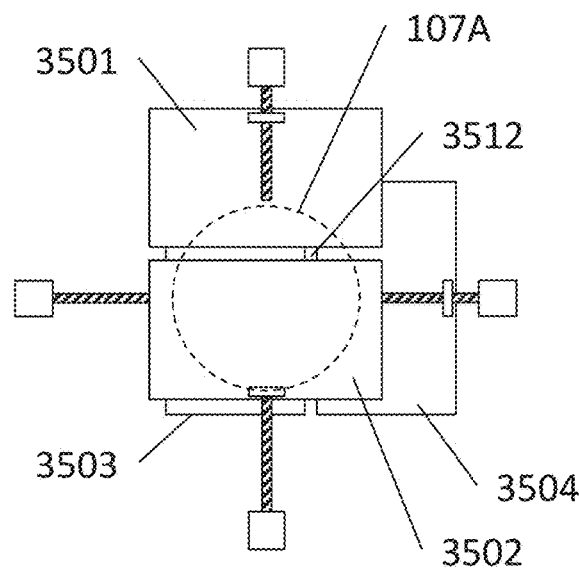
FIG. 21D is a top view of the collimator of FIG. 21C with a smaller ROI.

In the example of FIG. 21D hole 3512 is also generally at the top-right area of x-ray beam cross-section 107A but the distance between plates 3501 and 3502 was reduced and also the distance between plates 3503 and 3504 was reduced. As a result, the size of hole 3512 was reduced and the resultant ROI is smaller now.

Figure 21E:
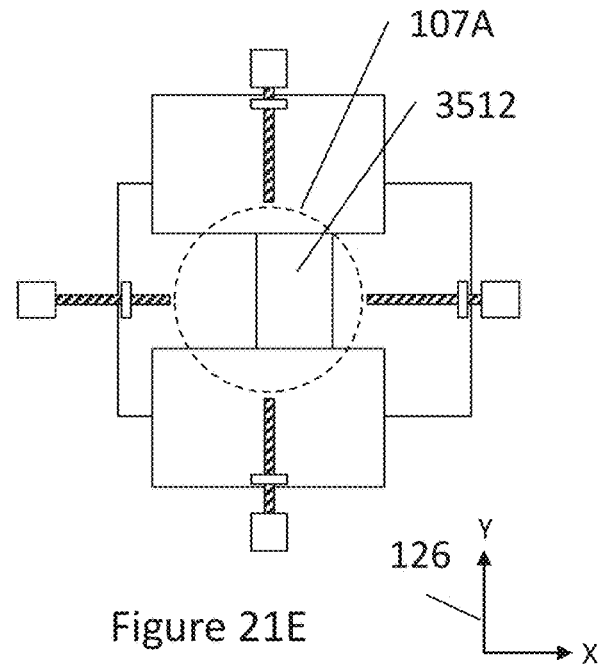
FIG. 21E is a top view of the collimator of FIG. 21C with a larger ROI and with a different geometry.

In FIG. 21E the hole is still in the upper-right area of x-ray beam cross-section 107A but the distance between plates was changed again to produce a large rectangle that is also particularly longer in the Y direction than in the X direction. The ROI therefore becomes larger and also of a different shape.

With this example of collimator 3500 therefore the ROI of image 120A can not only be moved across the area of image 120A to the desired location but also the size and aspect ratio of the ROI can be changed as desired, to compensate for zoom in image intensifier 114 or for other reasons.

It would be appreciated that although FIG. 21A implies that pairs of collimator plates are arranged in the same plane, this is not a limitation of the invention and each of the plates of a plates pair can be positioned in a different plane.

Figure 22:
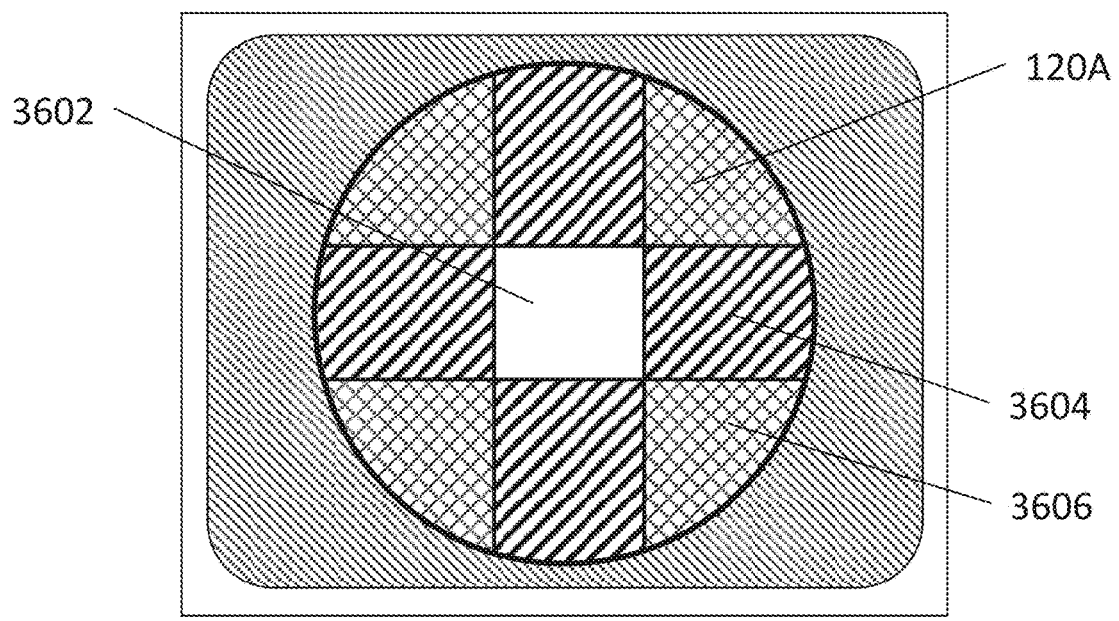
FIG. 22 illustrates the x-ray intensity distribution in different areas of the image when the ROI is in the position presented in FIG. 21B.

Reference is made now to FIG. 22, illustrating the x-ray intensity distribution in different areas of image 120A when the ROI is in the position presented in FIG. 21B. In this example there is no object (patient) between collimator 3500 and input area 112 so, ideally, without collimator 3500 the x-ray radiation over input area 112 would be uniform. In this example, as a result of collimator 3500 the area of image 120A is divided to 3 intensity areas: 3602, the ROI, where the original 100% intensity is, 3604 (4 such areas) where the intensity is 30% of the ROI and 3606 (4 such areas) where the intensity is 9% of the ROI.

The above described methods to correct background are fully applicable to correct the background of the present example where each of areas 3604 and 3606 require its own correction parameters.

It would be appreciated therefore that the current example can be used together with the above described correction methods.

It would be appreciated that although the above was described in reference to an image intensifier it is applicable to any detector, including a flat panel detector. The geometry of the detector, the zoom area and the ROI can be of a mixed nature and do not need to be of the same nature (i.e. circular or rectangular or another geometry).

It will be appreciated that any of the above described collimator's plates and collimators may be partially transparent to x-ray radiation.

It will be appreciated that the above described collimator's plates and collimators are not limited to be partially transparent and may be opaque.

It will be appreciated that for every zoom factor, any one of the collimator's holes may be used for any desired ROI.

It will also be appreciated that the shape of the holes is not limited to the shape shown and any shape may be used.

It would be appreciated by those skilled in the art that the above described methods and technologies are not limited to the configurations and methods mentioned herein above as examples. These are provided as examples and other configurations and methods can be used to optimize final result, depending on the specific design and the set of technologies implemented in the production of the design, including combinations of various embodiments described separately.

The herein above embodiments are described in a way of example only and do not specify a limited scope of the invention.

The scope of the invention is defined solely by the claims provided herein below.

The invention claimed is:

1. An imaging system comprising:
   a radiation source and radiation thereby;
   a detector having an input surface;
   a monitor configured to display images detected by said detector;
   a Graphical User Interface (GUI) for determining at least one Region of Interest (ROI) on a displayed image; and
   a collimator comprising means for modulating intensity of said radiation according to said at least one ROI; and
   means for locking and moving said determined shape of said at least one ROI on said means for displaying;
   wherein said GUI comprises means for displaying detected images and means for determining shape and location of said at least one ROI.

2. The system of claim 1, further comprising:
   an image processing unit connected between said detector and said monitor, said image processing unit configured to optimize a detected image displayed on said monitor according to at least one image part in said at least one ROI.

3. The system of claim 1, wherein said means for determining shape and location of said at least one ROI comprises sliders.

4. The system of claim 1, wherein said means for determining shape and location of said at least one ROI comprises drawing tools.

5. The system of claim 4, wherein said drawing tools are configured to enable to mark an enclosing shape around at least one image area.

6. The system of claim 4, wherein said drawing tools are configured to enable to mark at least one line; and wherein said means for determining shape and location of said at least one ROI comprises means for calculating an enclosing shape around said at least one line.

7. The system of claim 1, wherein said means for determining shape and location of said at least one ROI comprises means for tapping on a selected location on said means for displaying and means for determining an enclosing shape around said tapping location.

8. The system of claim 1, wherein said means for determining shape and location of said at least one ROI comprises means for tapping on a selected location on said means for displaying thereby drawing a predetermined enclosing shape around said tapping location.

9. The system of claim 1, wherein said means for determining shape and location of said at least one ROI comprises means for tapping on a selected location on said means for displaying; and wherein said imaging system further comprises an image processing unit configured to perform image processing for recognizing an organ area in which said selected location is included, thereby drawing a predetermined shape around said recognized organ.

10. The system of claim 1, wherein said means for moving said determined shape of said at least one ROI comprises means for moving said determined shape by dragging said determined shape to a different location on said means for displaying.

11. The system of claim 1, wherein said means for moving said determined shape of said at least one ROI comprises means for tapping on a different location on said means for displaying thereby automatically moving said determined shape to said different location on said means for displaying.

12. The system of claim 1, wherein said imaging system further comprises an image processing unit configured to perform image processing for recognizing an organ included in a selected location; and wherein said means for moving said determined shape of said at least one ROI comprises means for automatically moving said determined shape according to movements of said organ on said means for displaying.

13. The system of claim 1, wherein said means for moving said determined shape of said at least one ROI on said means for displaying comprises at least one of a tracking device and a voice command.

14. The system of claim 13, wherein said tracking device comprises at least one of an eye tracker; and a hand gesture tracking device.

15. The system of claim 1, further comprising means for at least one of automatically moving a selected ROI on said means for displaying; and automatically changing the size of a selected ROI based on one of: a movement of a patient; a movement of a table, on which said patient is lying; and a movement of a medical device inserted into said patient's body.

16. The system of claim 1, wherein said GUI further comprises means for rotating said determined at least one ROI.

17. A method of controlling a shape of a Region of Interest (ROI) in an imaging system, comprising:
providing an imaging system comprising:
a radiation source and radiation thereby;
a detector having an input surface;
a Graphical User Interface (GUI) for determining at least one ROI; and
a collimator comprising means for modulating intensity of said radiation according to said at least one ROI;
wherein said GUI comprises means for displaying detected images and means for determining shape and location of said at least one ROI;
using said GUI for displaying detected images and determining shape and location of said at least one ROI; and
locking and moving said determined shape of said at least one ROI on said means for displaying.

18. The method of claim 17, wherein said determining shape and location of said at least one ROI comprises moving sliders.

19. The method of claim 17, wherein said determining shape and location of said at least one ROI comprises drawing an enclosing shape around at least one image area.

20. The method of claim 17, wherein said determining shape and location of said at least one ROI comprises drawing at least one line; and calculating an enclosing shape around said at least one line.

21. The method of claim 17, wherein said determining shape and location of said at least one ROI comprises tapping on a selected location on said means for displaying; and determining an enclosing shape around said tapping.

22. The method of claim 17, wherein said determining shape and location of said at least one ROI comprises tapping on a selected location on said means for displaying thereby drawing a predetermined shape around said tapping location.

23. The method of claim 17, wherein said determining shape and location of said at least one ROI comprises tapping on a selected location on said means for displaying; recognizing an organ area in which said selected location is included by image processing; and drawing a predetermined shape around said recognized organ.

24. The method of claim 17, wherein moving said determined shape of said at least one ROI comprises dragging said determined shape to a different location on said means for displaying.

25. The method of claim 17, wherein moving said determined shape of said at least one ROI comprises tapping on a different location on said means for displaying thereby automatically moving said determined shape to said different location on said means for displaying.

26. The method of claim 17, wherein moving said determined shape of said at least one ROI comprises using image processing for recognizing an organ; and automatically moving said determined shape according to movements of said organ on said means for displaying.

27. The method of claim 17, wherein moving said determined shape of said at least one ROI on said means for displaying comprises using at least one of a tracking device and a voice command.

28. The method of claim 27, wherein said tracking device comprises at least one of an eye tracker; and a hand gesture tracking device.

29. The method of claim 17, further comprising at least one of automatically moving a selected ROI on said means for displaying; and automatically changing the size of a selected ROI based on one of: a movement of a patient; a movement of a table, on which said patient is lying; and a movement of a medical device inserted into said patient's body.

30. An imaging system comprising:
   a radiation source and radiation thereby;
   a detector having an input surface;
   a monitor configured to display images detected by said detector;
   a Graphical User Interface (GUI) for determining at least one Region of Interest (ROI) on a displayed image; and
   a collimator comprising means for modulating intensity of said radiation according to said at least one ROI;
   wherein said GUI comprises means for displaying detected images and means for determining shape and location of said at least one ROI; and
   wherein said GUI further comprises means for rotating said determined at least one ROI.

31. A method of controlling a shape of a Region of Interest (ROI) in an imaging system, comprising:
   providing an imaging system comprising:
      a radiation source and radiation thereby;
      a detector having an input surface;
      a Graphical User Interface (GUI) for determining at least one ROI; and
      a collimator comprising means for modulating intensity of said radiation according to said at least one ROI;
   wherein said GUI comprises means for displaying detected images and means for determining shape and location of said at least one ROI;
   using said GUI for displaying detected images and determining shape and location of said at least one ROI; and
   at least one of:
      automatically moving a selected ROI on said means for displaying; and
      automatically changing the size of a selected ROI based on one of:
         a movement of a patient;
         a movement of a table, on which said patient is lying; and
         a movement of a medical device inserted into said patient's body.

* * * * *